(12) United States Patent
Broglie et al.

(10) Patent No.: US 6,376,749 B1
(45) Date of Patent: Apr. 23, 2002

(54) STARCHES VIA MODIFICATION OF EXPRESSION OF STARCH BIOSYNTHETIC ENZYME GENES

(75) Inventors: Karen E. Broglie, Landenberg, PA (US); Natalie L. Hubbard; Theodore M. Klein, both of Wilmington, DE (US); Jonathan E. Lightner, Airville, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/257,894

(22) Filed: Feb. 25, 1999

Related U.S. Application Data

(63) Continuation-in-part of application No. 09/091,052, filed as application No. PCT/US96/19678 on Dec. 12, 1996, now abandoned.
(60) Provisional application No. 60/009,113, filed on Dec. 20, 1995.

(51) Int. Cl.$^7$ ........................ C12N 15/82; C12N 15/29; C12P 19/04; A01H 5/00
(52) U.S. Cl. ........................ 800/284; 800/278; 800/286; 800/287; 800/320.1; 435/101; 435/468
(58) Field of Search ................................ 800/278, 284, 800/286, 287, 320.1; 435/468, 101

(56) References Cited

U.S. PATENT DOCUMENTS

| | | | |
|---|---|---|---|
| 4,945,050 A | 7/1990 | Sanford et al. | 435/172.1 |
| 5,107,065 A | 4/1992 | Shewmaker et al. | 800/205 |
| 5,190,931 A | 3/1993 | Inouye | 435/91 |
| 5,283,323 A | 2/1994 | Brzofsky et al. | 530/387.1 |
| 5,300,145 A | 4/1994 | Fergason et al. | 106/213 |

FOREIGN PATENT DOCUMENTS

| | | | |
|---|---|---|---|
| EP | 0 138 341 | | 4/1985 |
| EP | 0 295 959 | | 12/1988 |
| EP | 0 301 749 | | 2/1989 |
| WO | WO 92/14827 | * | 9/1992 |
| WO | WO 93/11245 | | 6/1993 |
| WO | WO 94/09144 | | 4/1994 |
| WO | WO 94/11516 | | 5/1994 |
| WO | WO 94/11520 | * | 5/1994 |
| WO | 97/22703 | | 6/1997 |

OTHER PUBLICATIONS

Fisher et al. Plant Physiol. 102: 1045–1046, 1993.*
Kossmann et al. Progress Biotechnol. 10: 275–277, 1995.*
Willmitzer et al. Plant Polymeric Carbohydrates, Jan. 1999, 33–39.*
Baba et al. Biochem. Biophys. Res. Commun.: 181(1): 87–94, Nov. 1991.*
Han Ping Guan et al., Plant Phys., vol. 102:1269–1273, 1993, Differentiation of the Properties of the Branching Isozymes from Maize (Zea mays).
Karen D. Hedman et al. Biochem. Genetics, vol. 20:5/6):483–492, 1982, Gene Dosage at the amylose–extender Locus of Maize: Effects on the Levels of Starch Branching Enzymes.
Han Ping Guan et al., Plant Phys., vol. 104:1449–1453, 1994, Expression of Branching Enzyme I of Maize Endosperm in *Escherichia coli*.
Han Ping Guan et al., PNAS, vol. 92:964–967, Feb. 1995, Maize branching enzyme catalyzes synthesis of glycogen––like polysaccharide in glgB–deficient *Escherichia coli*.
Tadashi Baba et al., Biochem. and Biophys. Res. Commun., vol. 181(1):87–94, Nov. 27, 1991, Sequence Conservation of the Catalytic Regions of Amylolytic Enzymes in Maize Branching Enzyme–I.
J.M. Bae et al., Maydica, vol. 35:317–322, 1990, Cloning and Characterization of the Brittle–2 Gene of Maize.
Judy Callis et al., Genes & Dev., vol. 1:1183–1200, 1987, Introns increase gene expression in cultured maize cells.
Gary A. Thompson et al., BioEssays, vol 10(4):108–113, Apr. 1989, Structural Elements Regulating Zein Gene Expression.
J.A.K.W. Kiel et al., J. DNA Sequencing and Mapping, vol. 3:221–232, 1992, The glgB gene from the thermopile *Bacillus caldolyticus* encodes a thermolabile branching enzyme.
Celia J. Brunton et al., Molecular Microbiology, vol. 18(1):89–99, 1995, Tissue–specific glycogen branching isoenzymes in a multicellular prokaryote, *Stremtomyces coelicolor* A3(2).
D.V. Glover et al., 1987, in Corn: Nutritional Quality of Cereal Grains; Genetic and Agronomic Improvement, R.A. Olson and K. J. Frey, eds. American Society of Agronomy, Madison Wisconsin, pp. 183–336.
Lloyd W. Rooney et al., 1987, Chapter 13, Food Uses of Whole Corn and Dry–milled Fractions, in Corn: Chemistry and Technology, pp. 399–429, S. A. Watson and P.E. Ramstead, eds. American Association of Cereal Chemists, Inc., St. Paul, Minnesota.

(List continued on next page.)

*Primary Examiner*—David T. Fox

(57) ABSTRACT

The instant invention discloses utilization of a cDNA clone to construct sense and antisense genes for inhibition of starch branching enzyme enzymatic activity in corn. More specifically, this invention concerns a method of controlling the starch fine structure of starch derived from the grain of corn comprising: (1) preparing a chimeric gene comprising a nucleic acid fragment encoding a starch branching enzyme structural gene or a fragment thereof, operably linked in either sense or antisense orientation on the upstream side to a nucleic acid fragment encoding a promoter that directs gene expression in corn endosperm tissue, and operably linked on the downstream side to a nucleic acid fragment encoding a suitable regulatory sequence for transcriptional termination, and (2) transforming corn with said chimeric gene, wherein expression of said chimeric gene results in alteration of the fine structure of starch derived from the grain of said transformed corn compared to the fine structure of starch derived from corn not possessing said chimeric gene.

13 Claims, 16 Drawing Sheets

OTHER PUBLICATIONS

S. R. Eckhoff, Proceedings of the Fourth Corn Utilization Conference, Jun. 24–26, 1992, St. Louis, MO, printed by the national Corn Growers Association.

Tuschhoff, J.V., (1986) Hydroxypropylated Starches, In Modified Starches: Properties and Uses, O.B. Wurzburg, ed., CRC Press, Boca Raton, FL pp. 89–96.

Jamshid Khoshnoodi et al., FEBS Letters, vol. 332(1/2):132–138, Oct. 1993, Characterization of the 97 and 103 kDA forms of starch branching enzyme from potato tubers.

Jens Kobmann et al., Mol. Gen. Genet., vol. 230:39–44, 1991, Cloning and Expression Analysis of a potato cDNA that encodes branching enzyme: evidence for co–expression of starch biosynthetic genes.

Charles D. Boyer et al., Plant Phys., vol. 67:1141–1145, 1981, Evidence for Independent Genetic Control of the Multiple Forms of Maize Endosperm Branching Enzymes and Starch Synthases.

Yasuhito Takeda et al., Carbohydrate Res., vol. 240:253–263, 1993, Branching of amylose by the branching isoenzymes of maize endosperm.

Dane K. Fisher et al., Plant Phys., vol. 102:1045–1046, 1993, Starch Branching Enzyme II from Maize Endosperm.

Dane K. Fisher et al., Plant Phys., vol. 108:1313–1314, 1995, A cDNA Encoding Starch Branching Enzyme I from Maize Endosperm.

Phillip S. Stinard et al., The Plant Cell, vol. 5:1555–1566, 1993, Genetic Isolation, Cloning, and Analysis of a Mutator–Induced, Dominant Antimorph of the Maize amylose extender1 Locus.

Tadishi Baba et al., Agric. Biol. Chem., vol. 48(7):1763–1775, 1984, Structural Characterization of Amylopectin and Intermediate Material in Amylomaize Starch Granules.

T. Yamada et al., Starch/Starke, vol. 30(5):145–148, 1978, A Novel Type of Corn Starch from a Strain of Maize.

June E. Bourque, Plant Science, vol. 105:125–149, 1995, Antisense strategies for genetic manipulations in plants.

R. B. Flavell, PNAS, vol. 91:3490–3496, Apr. 1994, Inactivation of Gene Expression in Plants as a Consequence of Specific Sequence Duplication.

Susumu Hizukuri, Carbohydrate Res., vol. 147:342–347, 1986, Polymodal distribution of the chain lengths of amylopectins, and its significance.

Paul J. Jenkins et al., Starch/Starke, vol. 45(12):417–420, 1993, A Universal Feature in the Structure of Starch Granules from Different Botanicia Sources.

National Center for Biotechnology Information General Identifier No. 394742, Jan. 21, 1998.

National Center for Biotechnology Information General Identifier No. 619938, Jun. 28, 1996.

National Center for Biotechnology Information General Identifier No. 726489, Jun. 28, 1996.

Joan T. Odell et al., Nature, vol. 313:810–812, Feb. 28, 1985, Identification of DNA Sequences Required for activity of the cauliflower mosaic virus 35S promoter.

Michael E. Fromm et al., Biotechnology, vol. 8:833–839, Sep. 1990, Inheritance and Expression of Chimeric Genes in the Progeny of Transgenic Maize Plants.

T. M. Klein et al., Nature, vol. 327:70–73, Mar. 7, 1987, High–velocity Microprojectiles for Delivering Nucleic Acids into Living Cells.

J. H. Oard et al., Plant Cell Reports, vol. 8:156–160, 1989, Chimeric Gene Expression Using Maize Intron in Cultured Cells of Breadwheat.

Bronwyn R. Frame et al., The Plant Journal, vol. 6(6):941–948, 1994, Production of fertile transgenic maize plants by silicon carbide whisker–mediated transformation.

H.F. Kaeppler et al., Theor. Appln. Genet., vol. 84:560–566, 1992, Silicon Carbide Fiber–Mediated Stable Transformation of Plant Cells.

Michael C. Byrne et al., Plant Cell, Tissue and Organ Culture, vol. 8:3–15, 1987, Strain and Cultivar Specificity in the Agrobacterium–soybean Interaction.

Roger Hull et al., Virology, vol. 86:482–493, 1978, Structure of the Cauliflower Mosaic Virus Genome.

Charles D. Boyer et al., Carbohydrate Res., vol. 61:321–334, 1978, Multiple Forms of (1 to 4)–a–D–Glucan–6–Glycosyl Transferase form Developing *Zea Mays* L. Kerneis.

Julie Anderson Kirihara et al., Gene, vol. 71:359–370, 1988, Isolation and Sequence of a Gene Encoding a Methionine–rich 10–kDa Zein Protein from Maize.

J. A. K. W. Kiel et al., Gene, vol. 89:77–84, 1990, Nucleotide Sequence of the Synechoccus sp. PCC7942 branching Enzyme Gene (glgB): Expression in *Bacillus subtilis*.

L. Herrera–Estrella et al., Nature, vol. 310:115–120, Jul. 12, 1984, Light–Inducible and Chloroplast–Associated Expression of a Chimeric Gene Introduced Intro Nicotiana Tabacum using a Ti plasmid vector.

Giorgio Morelli et al., Nature, vol. 315:200–204, May 16, 1985, A short Conserved Sequence is Involved in the Light-Inducibility of a Gene Encoding Ribulose 1,5–biphosphate Carboxylase Small Subunit of Pea.

Gayle Lamppa et al., Nature, vol. 316:750–752, Aug. 22, 1985, Light–regulated and Organ–specific Expression of a Wheat Cab Gene in Transgenic Tobacco.

Michael E. Fromm et al., Nature, vol. 319:791–793, Feb. 27, 1986, Stable Transformation of Maize After Gene Transfer by Electroporation.

Kenneth R. Leuhrsen et al., Mol. Gen. Gent., vol. 225:81–93, 1991, Intron enhancement of Gene Expression and the Splicing Efficiency of Introns in Maize Cells.

Ingo Potrykus et al., Mol. Gen. Genet., vol. 199:183–188, 1985, Direct Gene Transfer to Cells of a Graminaceaous Monocot.

Preston A. Baecker et al., Journ. of Biol. CHem., vol. 261(19):8738–8743, 1986, Biosynthesis of Bacterial Glycogen.

Horst Lorz et al., Mol. Gen. Genet., vol. 199:178–182, 1985, Gene Transfer to Cereal Cells Mediated by Protplast Transformation.

Vicki J. Thon et al., Journ. of Biol. Chem., vol. 268(10):7509–7513, 1993, Isolation of Human Glycogen Branching Enzyme cDNAs by Screening Complementation in Yeast.

M. David Marks et al., Journ. of Biol. Chem., vol. 260(20):16451–16459, 1985, Nucleotide Sequence Analysis of Zein mRNAs from Maize Endosperm.

Richard Broglie et al., Science, vol. 224:838–843, May 25, 1984, Light–Regulated Expression of a Pea Ribulose–1, 5–Biphosphate Carboxylase Small Subunit Gene in Transformed Plant Cells.

Dane K. Fisher et al., Plant Mol. Biol., vol. 30:97–108, 1996, Two Closely Related cDNAs Encoding Starch Branching Enzyme from Arabidopsis Thaliana.

Claire Marris et al., Plant Mol. Biol., vol. 10:359–366, 1988, The 5' Flanking Region of a Barley B. Hordein Gene Controls Tissue and Developmental Specific CAT Expression in Tobacco Plants.

Susan B. Altenbach et al., Plant Mol. Biol., 13:513–522, 1989, Enhancement of the Methionine Content of Seed Proteins by the Expression of a Chimeric Gene Encoding a Methionine–Rich Protein in Transgenic Plants.

Christoph Maas et al., Plant Mol. Biol., vol. 16:199–207, 1991, The Combination of a Novel Stimulatory Element in the First Exon of the Maize Shrunken–1 Gene with the Following Intron 1 Enhances Reporter Gene Expression up to 100–fold.

Kitisri Sukhapinda et al., Plant Mol. Biol., vol. 8:209–216, 1987, Ri–plasmid as a Helper for Introducing Vector DNA into Alfalfa Plants.

Serik Omirulleh et al., Plant Mol. Biol., vol. 21:415–428, 1993, Activity of a Chimeric Promoter with the Doubled CaMV 35S Enhancer Element in Protoplast–Derived Cells and Transgenic Plants in Maize.

Cheryl Montain Laursen et al., Plant Mol. Biol., vol. 24:51–61, 1994, Production of Fertile Transgenic Maize by Electroporation of Suspension Culture Cells.

Susan B. Altenbach et al., Plant Mol. Biol., vol. 18:235–245, 1992, Accumulation of a Brazil Nut Albumin in Seeds of Transgenic Canola Results in Enhanced Levels of Seed Protein Methionine.

David A. Walters et al., Plant Mol. Biol., vol. 18:189–200, 1992, Transformation and Inheritance of a Hygromycin Phosphotransferase Gene in Maize Plants.

Maud A. W. Hinchee et al., Bio/Technology, vol. 6:915–922, 8.88, Production of Transgenic soybean Plants Using Agrobacterium–Mediated DNA Transfer.

Dennis E. McCabe et al., BioTechnology, vol. 6:923–926, 8/88, Stable Transformation of Soybean (glycine max) by Particle Acceleration.

T.J.V. Higgins, Annu. Rev. Plant Phys., vol. 35:191–221, 1984, Synthesis and Regulation of Major Proteins in Seeds.

N.P. Everett et al., Bio/Technology, vol. 5:1201–1204, Nov. 1987, Genetic Engineering of Sunflower (*Helianthus, Annuus* L.).

D. Facciotti et al., Bio/Technology, vol. 3:241–246, Mar. 1985, Light–Inducible Expression of a Chimeric Gene in Soybean Tissue Transformed with Agrobacterium.

N.S. Yang et al., PNAS, vol. 87:4144–4148, Jun. 1990, Maize Sucrose Synthase–1 Promoter Directs Phloem Cell-Specific Expression of Gus gene in Transgenic Tobacco Plants.

Paul Christou et al., PNAS, vol. 86:7500–7504, Oct. 1989, Inheritance and Expression of Foreign Genes in Transgenic Soybean Plants.

Robert B. Goldberg et al., Cell, vol. 56:149–160, Jan. 27, 1989, Regulation of Gene Expression during Plant Embryogenesis.

D. Gallardo et al., Plant Science, vol. 54:211–218, 1988, Genomic Organization of the 28 kDa Glutelin–2 Gene from Maize.

Mrinai R. Bhave et al., The Plant Cell, vol. 2:581–588, Jun. 1990, Identification and Molecular Characterization of Shrunken–2 cDNA Clones of Maize.

Michael G. Koziel et al., Bio/Technology, vol. 11:194–200, Feb. 1993, Field Performance of Elite Transgenic Maize Plants Expressing and Insecticidal Protein Derived from *Bacillus Thuringiensis*.

V. Colot et al., EMBO Journal, vol. 6(12):3559–3564, 1987, Localization of Sequences in Wheat Endosperm Protein Genes which Confer Tissue–Specific Expression in Tobacco.

Leslie M. Hoffman et al., EMBO Journal, vol. 6(11):3213–3221, 1987, Synthesis and Protein Body Deposition of Maize 15–kd Zein in Transgenic Tobacco Seeds.

Gloria Coruzzi et al., EMBO Journal, vol. 3(8):1671–1679, 1984, Tissue–specific and Light–regulated Expression of a Pean Nuclear Gene Encoding the Small Subunit of Ribulose–1,5–biphosphate Carboxylase.

Marc De Block et al., Plant Phys., vol. 91:694–701, 1989, Transformation of *Brassica napus* and *Brassica oleracea* using *Agrobacterium tumefaciens* and the Expression of the bar and neo Genes in the Transgenic Plants.

Paula P. Chee et al., Plant Phys., vol. 91:1212–1218, 1989, Transformation of Soybean (glycine max) by Infecting Germinating Seeds with *Agrobacterium tumefaciens*.

Ann de Clerq et al., Plant Phys., vol. 94:970–979, 1990, Stable Accumulation of Modified 2S Albumin Seed Storage Proteins with Higher Methionine Contents in Transgenic Plants.

John D. Williamson et al., Plant Phys., vol. 88:1002–1007, 1988, The Synthesis of a 19 Kilodalton Zein Protein in Transgenic Petunia Plants.

C. Daniel Riggs et al., Plant Science, vol. 63:47–57, 1989, Utilization of Luciferase Fusion Genes to Monitor Differential Regulation of Phytomagglutinin and Phaseoline Promoters in Transgenic Tobacco.

William J. Gordon–Kamm et al., The Plant Cell, vol. 2:60–618, Jul. 1990, Transformation of Maize Cells and Regeneration of Fertile Transgenic Plants.

Kathleen D'Halluin et al., The Plant Cell, vol. 4:1495–1505, Dec. 1992, Transgenic Maize Plants by Tissue Electroporation.

Robert Kodrzycki et al., The Plant Cell, vol. 1:105–114, Jan. 1989, The Opaque–2 Mutation of Maize Differentially Reduces Zein Gene Transcription.

Peter Poulsen et al., Plant Phys., vol. 102:1053–1054, 1993, Starch Branching Enzyme cDNA from *Solanum Tuberosum*.

Erica Unger et al., Plant Phys., vol. 96:124, 1991, Identification of Waxy Promoter Elements That Mediate Endosperm–Specific Expression in Maize Suspension Cells.

J.A.K.W. Kiel et al., Mol. Gen. Genet., vol. 230:136–144, 1991, Molecular Cloning and Nucleotide Sequence of the glycogen Branching Enzyme Gene (glgB) from *Bacillus Stearothermophilus* and Expression in *Escherichia coli* and *Bacillus subtillis*.

Rachel A. Burton et al., The Plant Journal, vol. 7(1):3–15, 1995, Starch Branching Enzymes Belonging to Distinct Enzyme Families are Differentially Expressed during Pea Embryo Development.

S.N.I.M. Salehuzzaman et al., Plant Mol. Biol., vol. 20:809–819, 1992, Cloning, Partial Sequencing and Expression of a cDNA Coding for Branching Enzyme in Cassava.

Tsutomu Kawasaki et al., Mol. Gen. Genet., vol. 237:10–16, 1993, Molecular Analysis of the Gene Encoding a Rice Starch Branching Enzyme.

Kouichi Mizuno et al., Journ. of Biol. Chem., vol. 268(25):19064–19091, 1993, Alteration of the Structural Properties of Starch Components by the Lack of an Isoform of Starch Branching Enzyme in Rice Seeds.

Vicki J. Thon et al., Journ. of Biol. Chem., vol. 267(21):15224–15228, 7/25, 1992, Coordinate Regulation of Glycogen Metabolism in the Yeast *Saccharomyces Cerevisiae*.

Ivan L. W. Ingelbrecht et al., The Plant Cell, vol. 1:671–680, Jul. 1989, Different 3'End Regions Strongly Influence the Level of Gene Expression in Plant Cells.

R. DeBlaere et al., Methods in Enzymology, vol. 153:277–292, 1987, Vectors for Cloning in Plant Cells.

* cited by examiner

STARCHES VIA MODIFICATION OF EXPRESSION OF STARCH BIOSYNTHETIC ENZYME GENES

CROSS-REFERENCE TO RELATED APPLICATIONS

This application is a continuation-in-part of application Ser. No. 09/091,052 filed Jun. 10, 1998, now abandoned, which is a 371 of PCT/US96/19678 filed Dec. 12, 1996, which claims priority to provisional application No. 60/009, 113 filed Dec. 20, 1995.

BACKGROUND OF THE INVENTION

Characteristics and Commercial Utility of Starch

Starch is a mixture of two polysaccharides, amylose and amylopectin. Amylose is an unbranched chain of up to several thousand α-D-glucopyranose units linked by α-1,4 glycosidic bonds. Amylopectin is a highly branched molecule made up of up to 50,000 α-D-glucopyranose residues linked by α-1,4 and α-1,6 glycosidic bonds. Approximately 5% of the glycosidic linkages in amylopectin are α-1,6 bonds, which leads to the branched structure of the polymer.

Amylose and amylopectin molecules are organized into granules that are stored in plastids. The starch granules produced by most plants are 15–30% amylose and 70–85% amylopectin. The ratio of amylose to amylopectin and the degree of branching of amylopectin affects the physical and functional properties of the starch. Functional properties, such as viscosity and stability of a gelatinized starch determine the usefulness and hence the value of starches in food and industrial applications. Where a specific functional property is needed, starches obtained from various crops such as corn, rice, or potatoes may meet the functionality requirements. If a starch does not meet a required functional property, if for example it must have stable viscosity under high temperatures and acidic conditions, the functionality can sometimes be achieved by chemically modifying the starch. Various types and degrees of chemical modification are used in the starch industry, and the labeling and use of chemically modified starches must meet government regulations.

Within the starch bearing organs of plants, the proportion of amylose to amylopectin and the degree of branching of amylopectin are under genetic control. For example, plants homozygous recessive for the waxy (wx) gene lack a granule-bound starch synthase enzyme and produce nearly 100% amylopectin. Plants homozygous recessive for the amylose extender (ae) gene can produce starch granules that are up to 90% amylose (see U.S. Pat. No. 5,300,145). The dull gene has been shown to influence the levels of activity of a starch synthase and a starch branching enzyme.

Most cereal crops are handled as commodities, and many of the industrial and animal feed requirements for these crops can be met by common varieties which are widely grown and produced in volume. However, there exists at present a growing market for crops with special end-use properties which are not met by grain of standard composition. Most commonly, specialty corn is differentiated from "normal" corn, also known as field corn, by altered endosperm properties, such as an overall change in the ratio of amylose to amylopectin as in waxy or high amylose corn, an increased accumulation of sugars as in sweet corn, or an alteration in the degree of endosperm hardness as in food grade corn or popcorn; Glover, D. V. and E. T. Mertz, (1987) in Corn: Nutritional Quality of Cereal Grains; Genetic and Agronomic Improvement, R. A. Olson and K. J. Frey, eds. American Society of Agronomy, Madison Wisconsin, pp. 183–336. Rooney, L. W. and S. O. Serna-Saldivar, (1987) Food Uses of Whole Corn and Dry-milled Fractions, in Corn: Chemistry and Technology, S. A. Watson and P. E. Ramstead, eds. American Association of Cereal Chemists, Inc., St. Paul, Minn., pp. 399–429. The current invention offers the buyers of specialty corn a source of starch having properties distinct from waxy starch and offers farmers the opportunity to grow a higher value-added crop than normal or waxy corn.

Purified starch is obtained from plants by a milling process. Corn starch is extracted from kernels through the use of a wet milling process. Wet milling is a multi-step process involving steeping and grinding of the kernels and separation of the starch, protein, oil and fiber fractions. A review of the corn wet milling process is given by S. R. Eckhoff in the Proceedings of the Fourth Corn Utilization Conference, Jun. 24–26, 1992, St. Louis, Mo., printed by the National Corn Growers Association, CIBA-GEIGY Seed Division and the United States Department of Agriculture. Starch is used in numerous food and industrial applications and is the major source of carbohydrates in the human diet. Typically, starch is mixed with water and cooked to form a thickened gel. Three important properties of a starch are the temperature at which it cooks, the viscosity the gel reaches, and the stability of the gel viscosity over time. The physical properties of unmodified starch during heating and cooling limit its usefulness in many applications. As a result, considerable effort and cost is needed to chemically modify starch in order to overcome these limitations of starch and to expand the usefulness of starch in industrial applications.

Some limitations of unmodified starches and properties of modified starches are given in Modified Starches: Properties and Uses, O. B. Wurzburg, ed., (1986) CRC Press Inc., Boca Raton, Fla. Unmodified starches have very limited use in food products because the granules swell and rupture easily, thus forming weak bodied, undesirable gels. Chemical modifications are used to stabilize starch granules thereby making the starch suitable for thousands of food and industrial applications including baby foods, powdered coffee creamer, surgical dusting powders, paper and yarn sizings and adhesives. Common chemical modifications include cross linking in which chemical bonds are introduced to act as stabilizing bridges between starch molecules, and substitution in which substituent groups such as hydroxyethyl, hydroxypropyl or acetyl groups are introduced into starch molecules.

The use of chemically modified starches in the United States is regulated by the Food and Drug Administration (FDA). "Food starch-modified" starches may be used in food but must meet specified treatment limits, and "industrial starch-modified" starches may be used in items such as containers that come in contact with food and must also meet specified treatment requirements; Code of Federal Regulations, Title 21, Chapter 1, Part 172, Food Additives Permitted in Food for Human Consumption, Section 172, 892, Food Starch-Modified, U. S. Government Printing Office, Washington, D. C. 1981; (a) Part 178, Indirect Food Additives, Sect. 178.3520, Industrial Starch-Modified. These regulations limit the degree of chemical modification by defining the maximum amount of chemical reagent that can be used in the modification steps. The levels of by-products in starch resulting from the modification process are also regulated. For example, propylene chlorohydrin residues in hydroxypropyl starch are of special concern; Tuschhoff, J. V., (1986) Hydroxypropylated Starches, In Modified Starches: Properties and Uses, O. B. Wurzburg, ed., CRC Press, Boca Raton, Fla. pp. 89–96.

Alteration of Starch Fine Structure Through Molecular Genetic Manipulation of Starch-Bearing Plants Differences in the degree of starch branching or polymerization are known to result in a change in the physiochemical properties of starch. It has been suggested that starches, tailor-made for specific applications, may be generated by alteration of the branch chain distribution of the amylopectin molecule, the relative proportion of amylose to amylopectin or the degree of polymerization of amylose. However, achieving phenotypic alteration of starch composition has been problematic; while key enzymes in starch biosynthesis have been identified, their exact roles remain uncertain. Thus, correlation of activities of particular enzymes with particular molecular characteristics of starch structure and, in turn, with starch function in food and industrial products has been difficult. Although desirable functional properties that an ideal starch might need can be envisioned, there is only a vague understanding of what the molecular structure of the starch should be to achieve this and little understanding of how particular starch biosynthetic enzymes specifically affect those parameters. For example, the role of individual enzymes in determining the branching patterns and length of branches is as yet unclear and is compounded by the lack of understanding of how branching enzymes and starch synthases interact.

WO 94/09144 discusses the generation of plants with improved ability to synthesize starch at elevated temperatures. This publication proposes that the limiting factor in grain filling at elevated temperature is the lability of certain starch biosynthetic enzymes, particularly starch synthase (SS) and starch branching enzyme (SBE). The introduction of genes encoding enzymes that have a higher optimum temperature for activity or that have a higher tolerance to heating into plants may afford an increase in the amount of starch deposited in the corn kernel. Moreover, it is claimed that this strategy may be used to generate starch of altered fine structure as a result of the introduction of donor genes whose expression may alter the balance of the different starch biosynthetic enzymes. Suggested donor genes include those that encode enzymes that display improved kinetic or allosteric properties relative to the endogenous enzyme or an extra copy of the endogenous gene that would compensate for losses in enzyme activity incurred due to heat lability. As a means to alter starch structure, WO 94/09144 also suggests the use of sense and antisense genes to alter the natural ratios of the different starch synthase and branching enzymes in the recipient plant. This publication discloses the effect of temperature on catalytic activity and enzyme stability for certain starch biosynthetic enzymes, however, no data are presented to subsantiate the proposed molecular strategies.

The results of attempts to inhibit SBE expression in potato using an antisense approach were recently reported by Virgin et al. at the 4th International Congress of Plant molecular Biology (June, 1994) and by Christensen et al. and Kossman et al. at the Plant Polysaccharide Symposium (July, 1994). In all cases, although SBE activity was almost completely abolished, the amylose-to-amylopectin ratio remained unaltered. Both Virgin et al. and Kossman et al. reported no change in amylopectin structure. However, Christensen et al. did report a change in the distribution of branch chains on the amylopectin molecule with an increase in the number of long branches.

The results in potato are unexpected, since only a single starch branching enzyme has been purified and only a single gene has been detected on Southern blots of potato genomic DNA, even under conditions of low stringency (Kooshnoodi, J. et al. (1993) *FEBS Letters* 332:132–138; Kossman, J. et al. (1991) *Mol. Gen. Genet.* 230:39–44). Thus, antisense suppression of the single starch branching enzyme gene in potato, resulting in significant reduction of enzyme levels and a concomitant decrease in starch branching enzyme activity, was expected to result in a measurable, reproducible change in starch composition and starch fine structure. The contrary and inconsistent results reported in the literature suggest that other starch branching enzyme genes that share little homology with the identified gene may also play a role in determining amylopectin structure in potato. Alternatively, branching enzyme activity in potato may be encoded by a single gene, but the protein may be present in such large excess that amylopectin quantities or structure are not affected even when greater than 90% of the enzyme activity is inhibited.

Alteration of starch fine structure in corn is complicated by the fact that three SBE isoforms have been identified. In corn endosperm, the three isoforms that demonstrate starch branching enzyme activity are SBEI, SBEIIa and SBEIIb. In the amylose extender (ae) mutant, SBEIIb activity has been found to be deficient while in the dull (du) mutant, decreased levels of SBEIIa are observed (Boyer, C. D. and Preiss, J. (1981) *Plant Physiol.* 67:1141–1145). Studies of the catalytic properties of the corn starch branching enzymes indicate that the isoforms differ in substrate preference and in the length of glucan chain that is transferred. SBEI activity is higher when amylose serves as the substrate, and longer chains are preferentially transferred. The SBEII isoforms display higher activity with more highly branched substrates such as amylopectin. These enzymes preferentially transfer shorter glucan chains (Guan et al. (1993) *Plant Physiol.* 102:1269–1273; Takeda et al. (1993) *Carbohydrate Res.* 240:253–263).

A corn SBEI cDNA has been cloned and sequenced (Baba et al. (1991) *Biochem. Biophys. Res. Commun.* 181:87–94; Fisher et al. (1995) *Plant Physiol.* 108:1313–1314). In addition, a corn SBEII cDNA clone has been isolated and the nucleotide sequence of the clone has been published (Fisher et al. (1993) *Plant Physiol.* 102:1045–1046). This cDNA clone maps to the ae locus, confirming that this locus encodes the structural gene for corn SBEIIb (Stinard et al. (1993) *Plant Cell* 5:1555–1566).

Starch isolated from the ae mutant is known to differ in structure from that isolated from dent corn (Baba et al. (1984) *Agric. Biol. Chem.* 48:1763–1775). The effect of the ae allele on starch properties has been investigated (Yamada et al. (1978) Starke 30:145–148). Increasing doses of ae in a waxy (wx) background produce an increase in the gelatinization temperature so that for the homozygous mutant, incomplete cooking of the starch is observed, even at 95° C. These authors indicate that the increase in viscosity associated with ae wx starch is highly desirable and suggest a "target" starch with properties intermediate between wx and ae wx. While mutations which influence the levels of corn SBEIIa and SBEIIb are available, mutations in the SBEI structural gene have yet to be identified. The lack of SBEI mutants may indicate that the absence of this branching enzyme isoform is lethal to the plant. Alternatively, a SBEI null mutation may give rise to no observable change in seed phenotype or one that is not readily distinguished from existing starch mutants.

Molecular genetic solutions to the generation of starches from corn with altered fine structures have a decided advantage over more traditional plant breeding approaches. Changes to starch fine structure can be produced by specifically inhibiting expression of one or more of the SBE isoforms by antisense inhibition or cosuppression. An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. Additionally the ability to restrict the expression of the altered starch phenotype to the reproductive tissues of the plant by the use of specific promoters may confer agronomic advantages relative to conventional mutations which will have an effect in all tissues in which the mutant gene is ordinarily expressed. Finally, the variable levels of antisense inhibition or cosuppression that arise from chromosomal position effects could produce a wider range of starch phenotypes than those that result from dosage effects of a mutant allele in corn endosperm.

The complex organization of starch branching enzymes in corn endosperm and the results reported in potato render attempts to manipulate starch fine structure by inhibition of gene expression of one of the known corn isoforms unpredictable. Reported scientific evidence indicates that inhibition of expression of a single starch branching enzyme gene and a measurable reduction of starch branching enzyme activity is not predictive of a corresponding change in starch fine structure. Moreover, antisense technology is inherently uncertain in that it is not obvious or predictable whether the entire gene or whether specific fragments and which fragments of a gene will be most effective in mediating strong antisense inhibition. Some results do indicate that strong expression of the antisense gene is required; however, good expression of the antisense transcript does not necessarily correlate with the observation of and the strength of the antisense phenotype (Bourque, J. (1995) *Plant Sci.* 105:125–149). Although several theories have been advanced to explain the phenomenon of cosuppression (Flavell, R. B. (1994) *Proc. Natl. Acad. Sci.* (USA) 91:3490–3496), it has become apparent that no single mechanism appears sufficient to describe all of the observed results. To date, cosuppression effects have been reported in tobacco, canola, soybean, tomato and Arabidopsis, all of which are dicot plants. No data have been reported that indicates that this phenomenon is operable in monocots.

Notwithstanding the ability to inhibit the expression of SBE genes in corn, a resulting change in starch phenotype remains unpredictable. Although the enzymatic steps are known, the molecular details of starch biosynthesis are not well understood. It is not clear whether the three SBE isoforms contribute equally throughout starch biosynthesis or whether each isoform plays a distinct role in assembling the amylopectin molecule at discrete steps along an obligatory pathway. In consideration of the possible interplay between the starch branching enzymes and the multiple starch synthases that function in glucan chain elongation, it is impossible to make predictions concerning starch structure based upon the catalytic properties of each isoform.

SUMMARY OF THE INVENTION

The instant invention discloses utilization of a cDNA clone to construct sense and antisense genes for inhibition of starch branching enzyme enzymatic activity in corn grain or endosperm. More specifically, this invention concerns a method of controlling the branch chain distribution of the amylopectin, the relative proportion of amylose to amylopectin and the degree of polymerization of amylose components of starch in corn comprising: (1) preparing a chimeric gene comprising a nucleic acid fragment encoding a starch branching enzyme structural gene or a fragment thereof, operably linked in either sense or antisense orientation on the upstream side to a nucleic acid fragment that encodes a promoter that directs gene expression in corn endosperm tissue, and operably linked on the downstream side to a nucleic acid fragment encoding a suitable regulatory sequence for transcriptional termination, and (2) transforming corn with said chimeric gene, wherein expression of said chimeric gene results in alteration of the branch chain distribution of the amylopectin molecular component of starch derived from the grain of said transformed corn compared to the branch chain distribution of the amylopectin molecular component of starch derived from corn not possessing said chimeric gene. This invention also concerns corn varieties prepared by transformation using said method, starch isolated from the grain of a corn variety prepared using said method, and a method of preparing a thickened foodstuff comprising combining a foodstuff, water, and an effective amount of a starch isolated from the grain of a corn variety prepared using the said method, and cooking the resulting composition as necessary to produce said thickened foodstuff.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 presents a restriction map of plasmid pBE240 that contains a cDNA insert comprising 78 bp of 5' untranslated DNA, a 2397 bp open reading frame encoding the corn SBEIIb coding region and 190 bp of 3' untranslated DNA.

Figure 5:
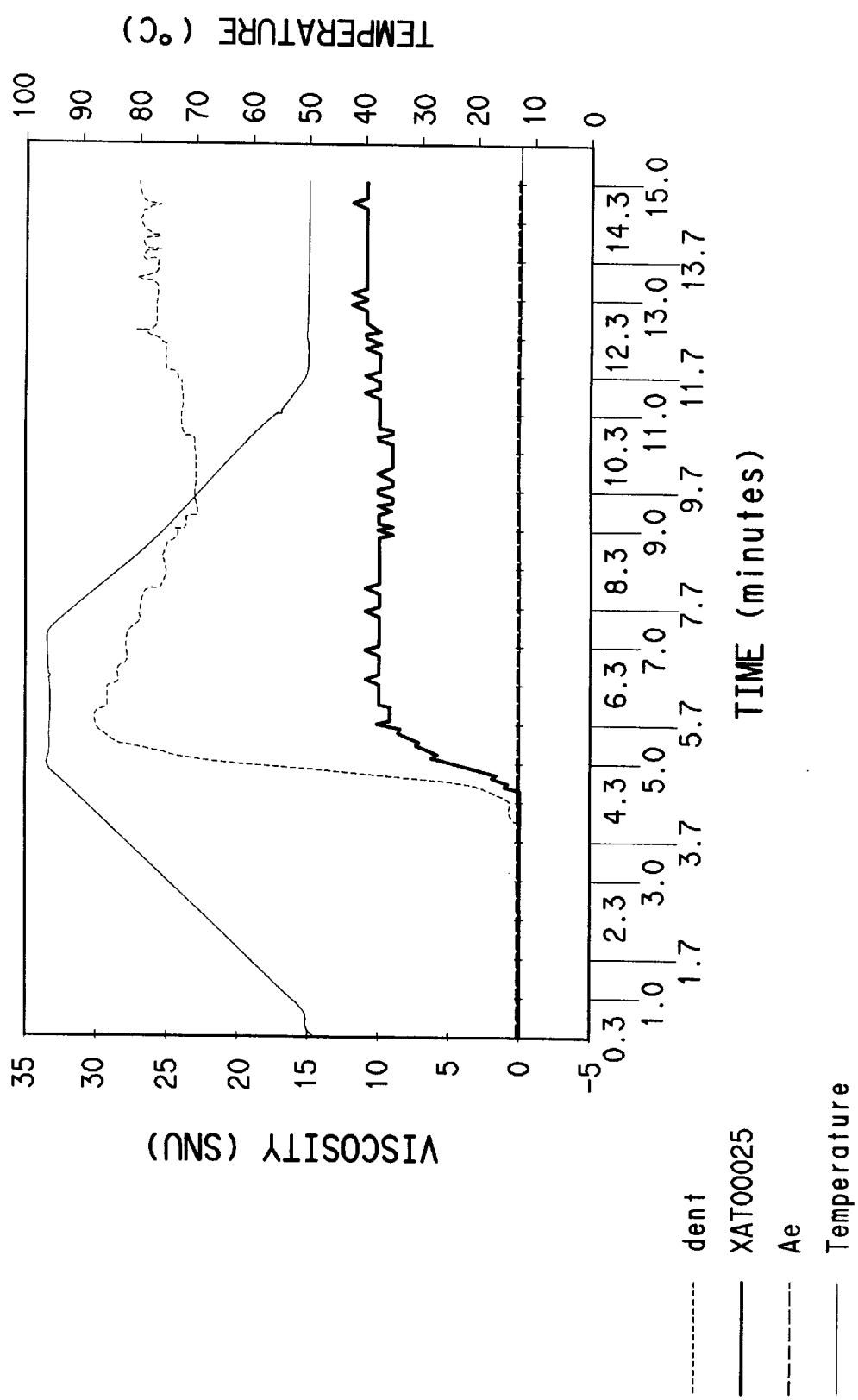

FIG. 5 compares RVA profiles of starch from normal dent corn kernels, kernels homozygous for amylose extender (ae) and starch from kernels homozygous for the pBE44 construct. Viscosity, in stirring number units (SNU), and temperature (degrees Celsius) have been measured and plotted as a function of time (in minutes).

Figure 7:
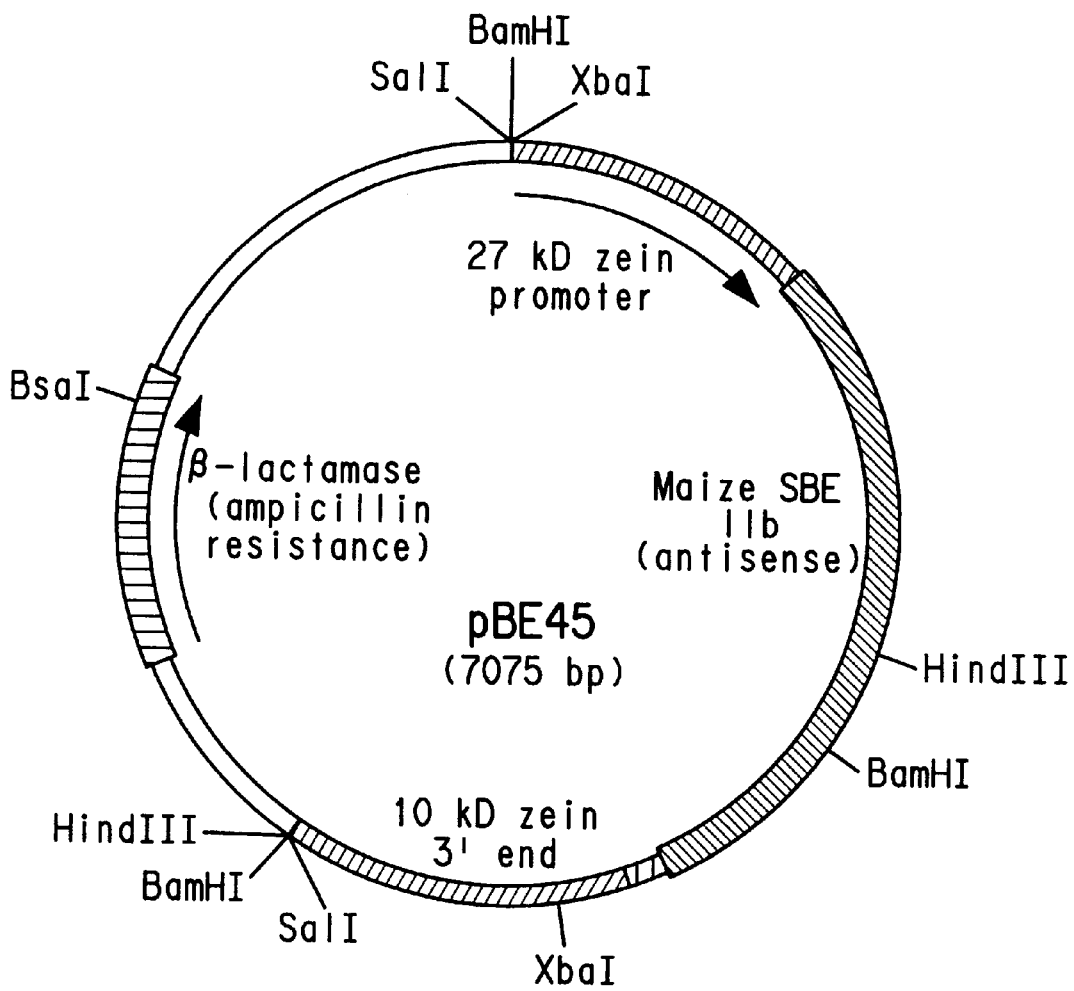

FIG. 7 is a restriction map of plasmid pBE45 comprising a 2165 bp near full length fragment of the insert of pBE240 in antisense orientation with respect to the corn 27 kd zein promoter.

Figure 8:
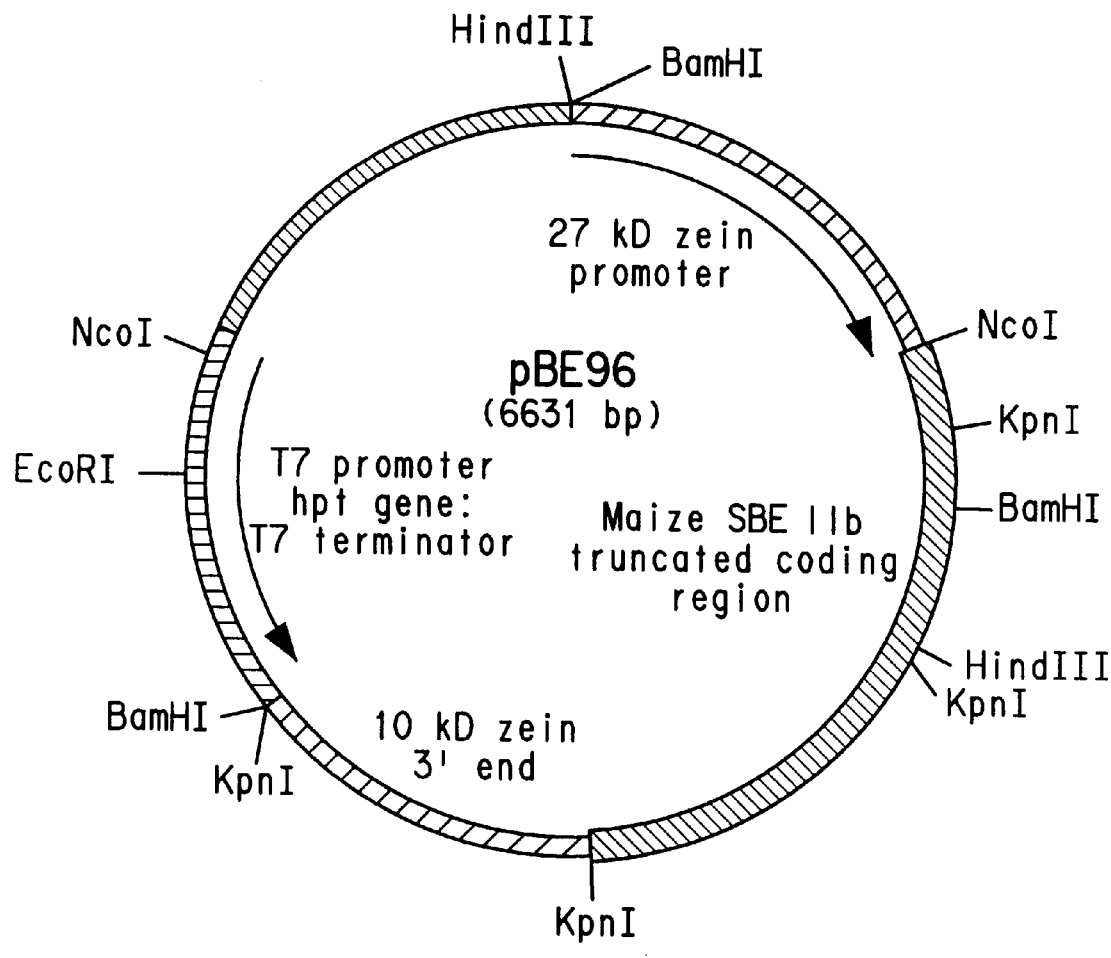

FIG. 8 is a restriction map of plasmid pBE96 comprising a 2087 bp near full length fragment of the insert of pBE240 in sense orientation with respect to the corn 27 kd zein promoter.

Figure 9:
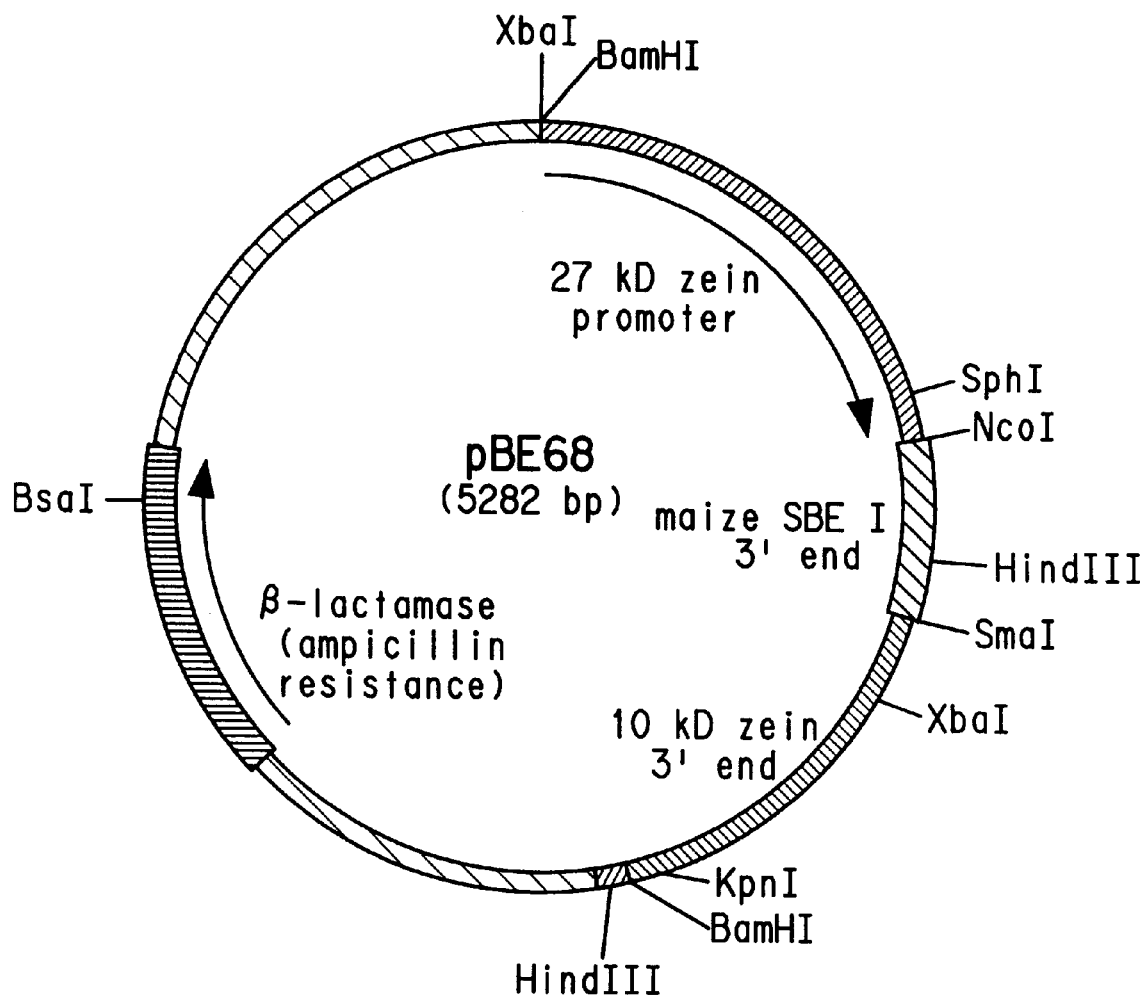

FIG. 9 is a restriction map of plasmid pBE68 comprising a 373 bp fragment representing the 3' end of the corn SBEI cDNA insert in pBE65 (SEQ ID NO:13), joined in antisense orientation to the corn 27 kd zein promoter.

Figure 10:
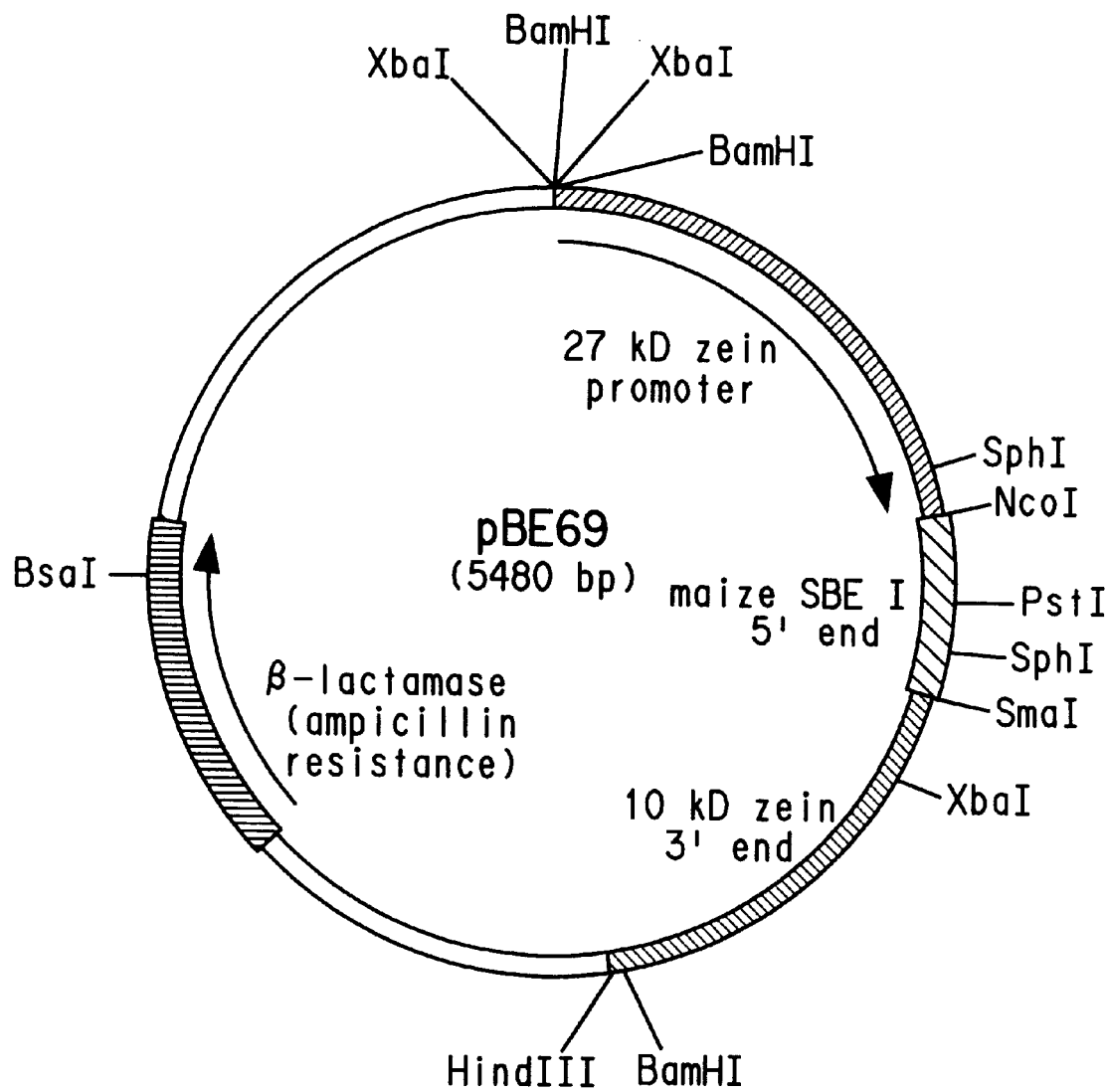

FIG. 10 is a restriction map of plasmid pBE69 comprising a 570 bp fragment representing the 5' end of the corn SBEI cDNA insert in pBE65 (SEQ ID NO: 16), joined in antisense orientation to the corn 27 kd zein promoter.

Figure 11:
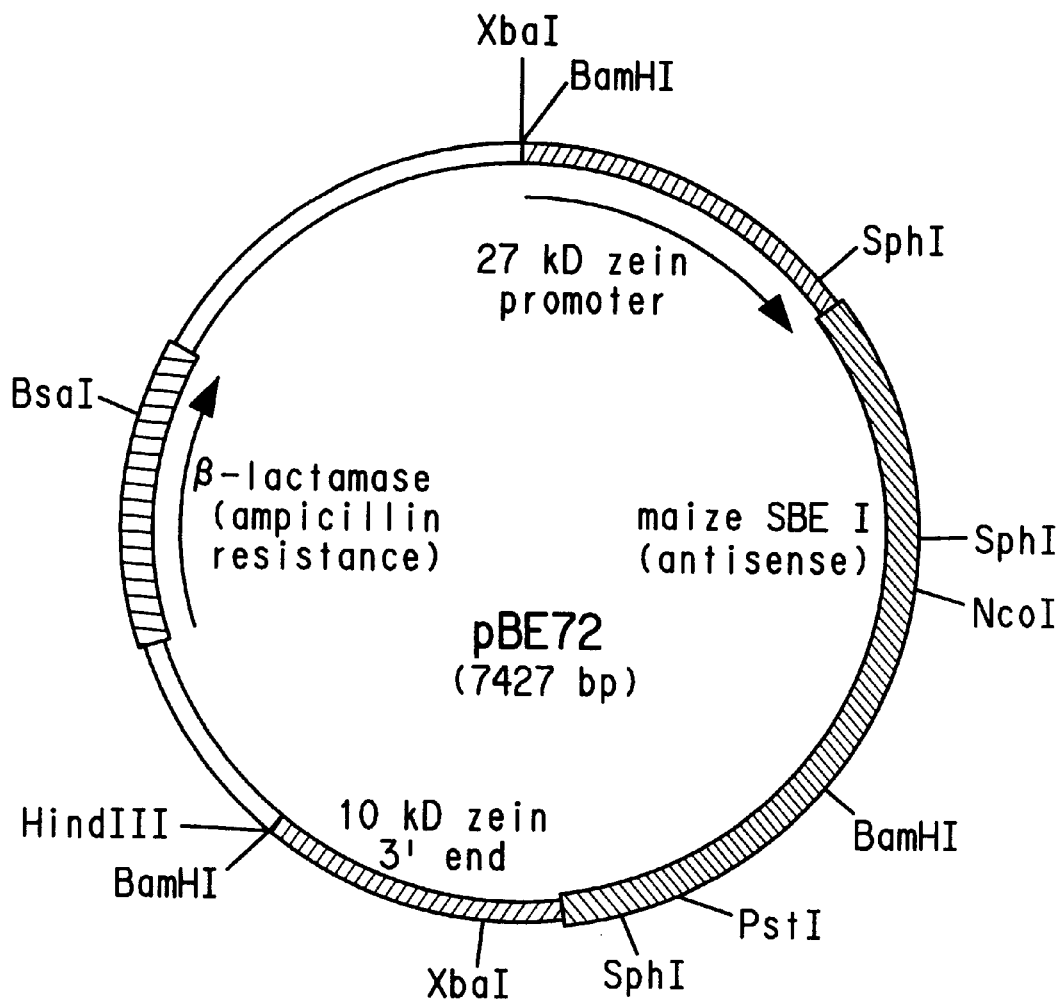

FIG. 11 is a restriction map of plasmid pBE72 comprising a 2487 bp near full length fragment the insert of pBE65 in antisense sense orientation with respect to the corn 27 kd zein promoter.

Figure 12:
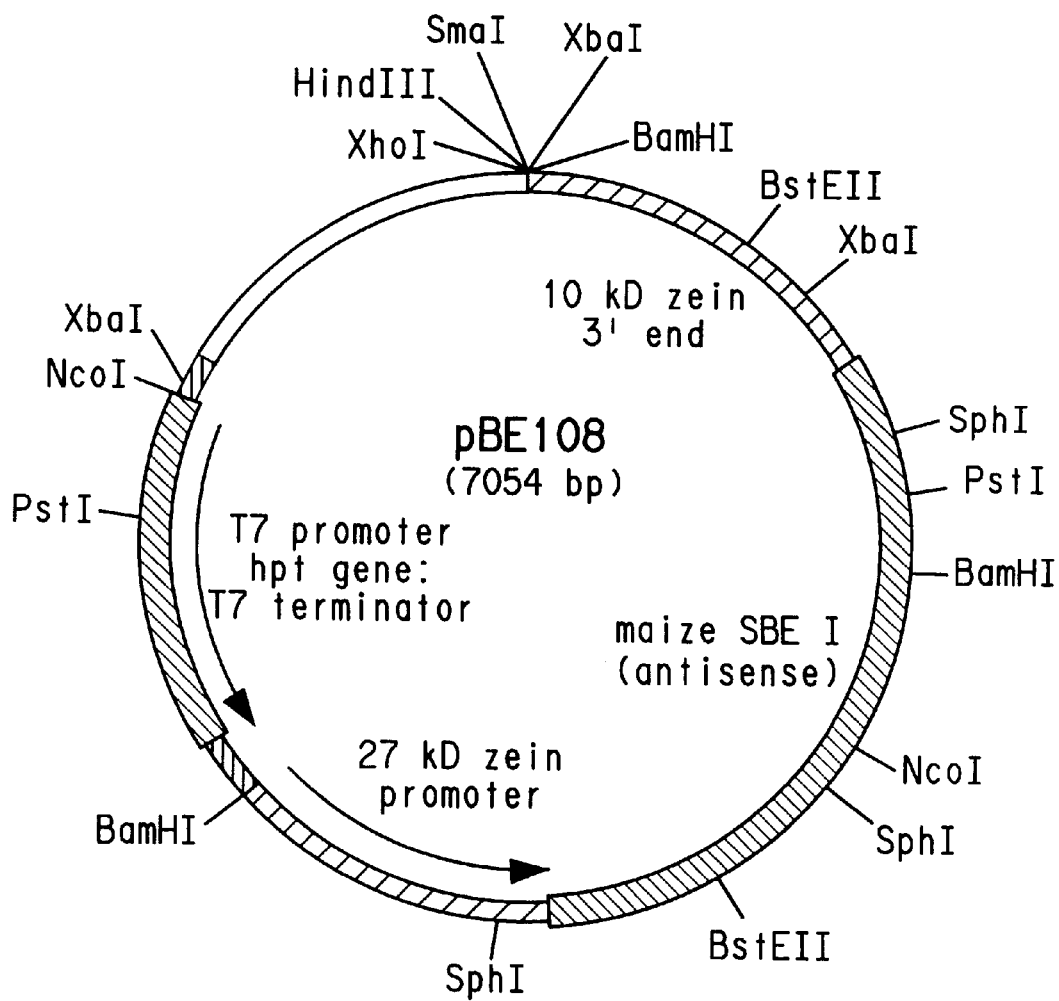

FIG. 12 is a restriction map of plasmid pBE108 comprising a hygromycin resistant variant of pBE72.

Figure 13:
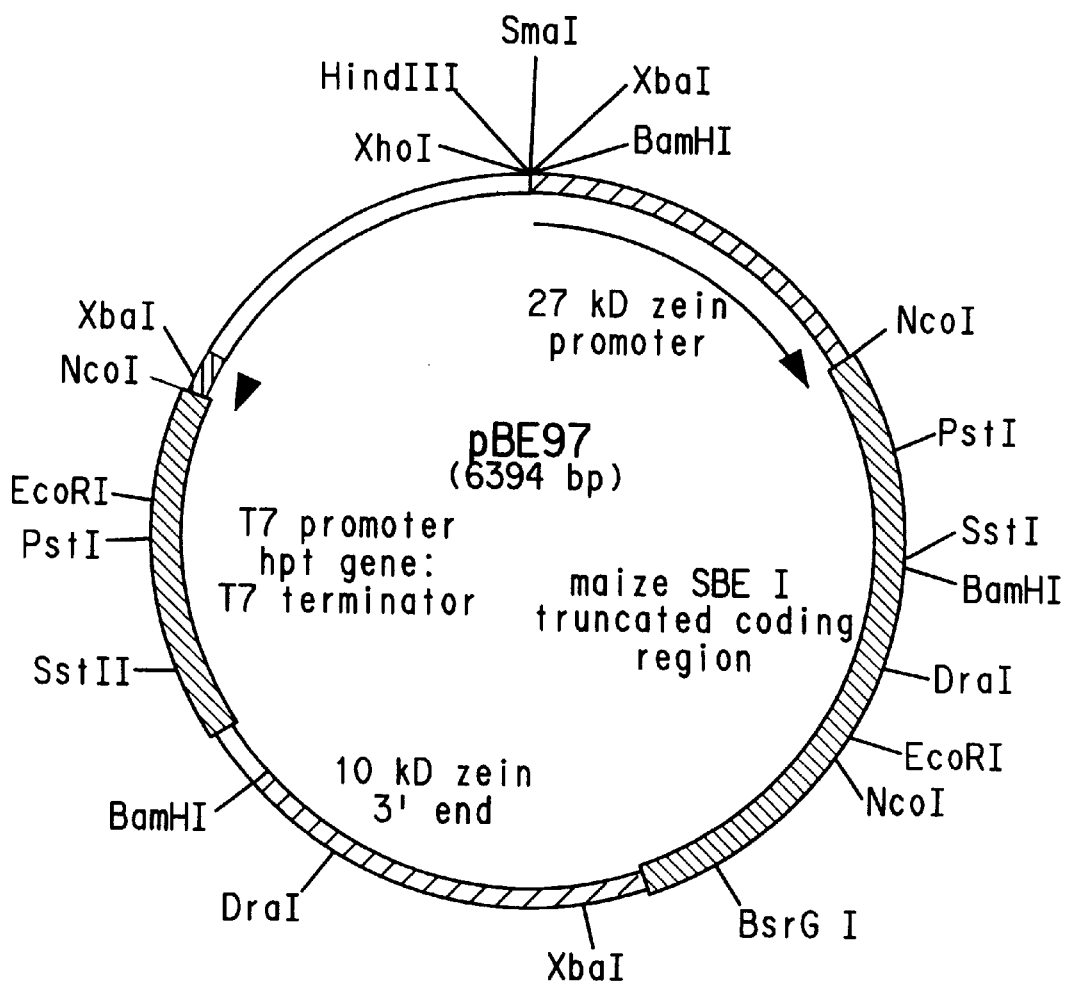

FIG. 13 is a restriction map of plasmid pBE97 comprising a 1865 bp near full length fragment the insert the SBEI cDNA of pBE65 (SEQ ID NO:20) joined in sense orientation to the 27 kD zein promoter.

Figure 14:
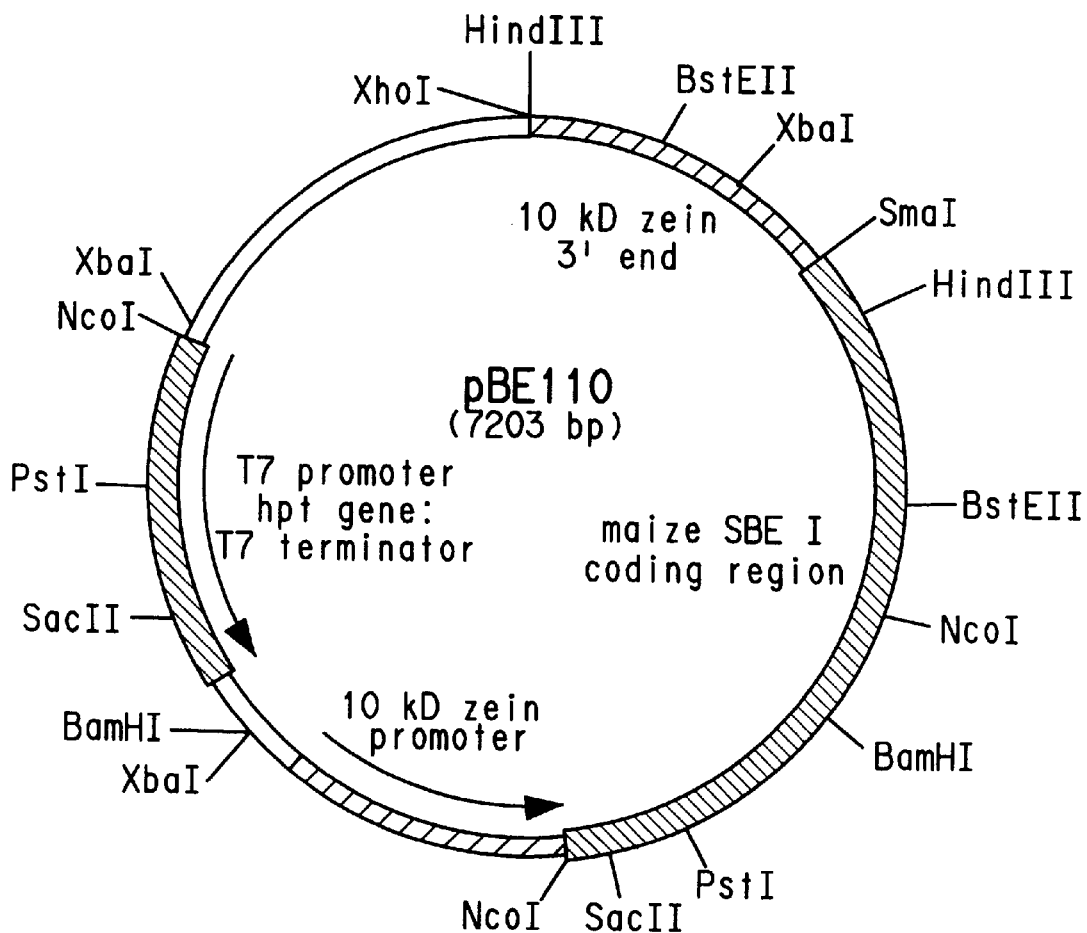

FIG. 14 is a restriction map of plasmid pBE110 comprising a 2565 bp cDNA fragment encoding a full length SBEI joined in sense orientation with respect to the maize 10 kd zein promoter.

Figure 15:
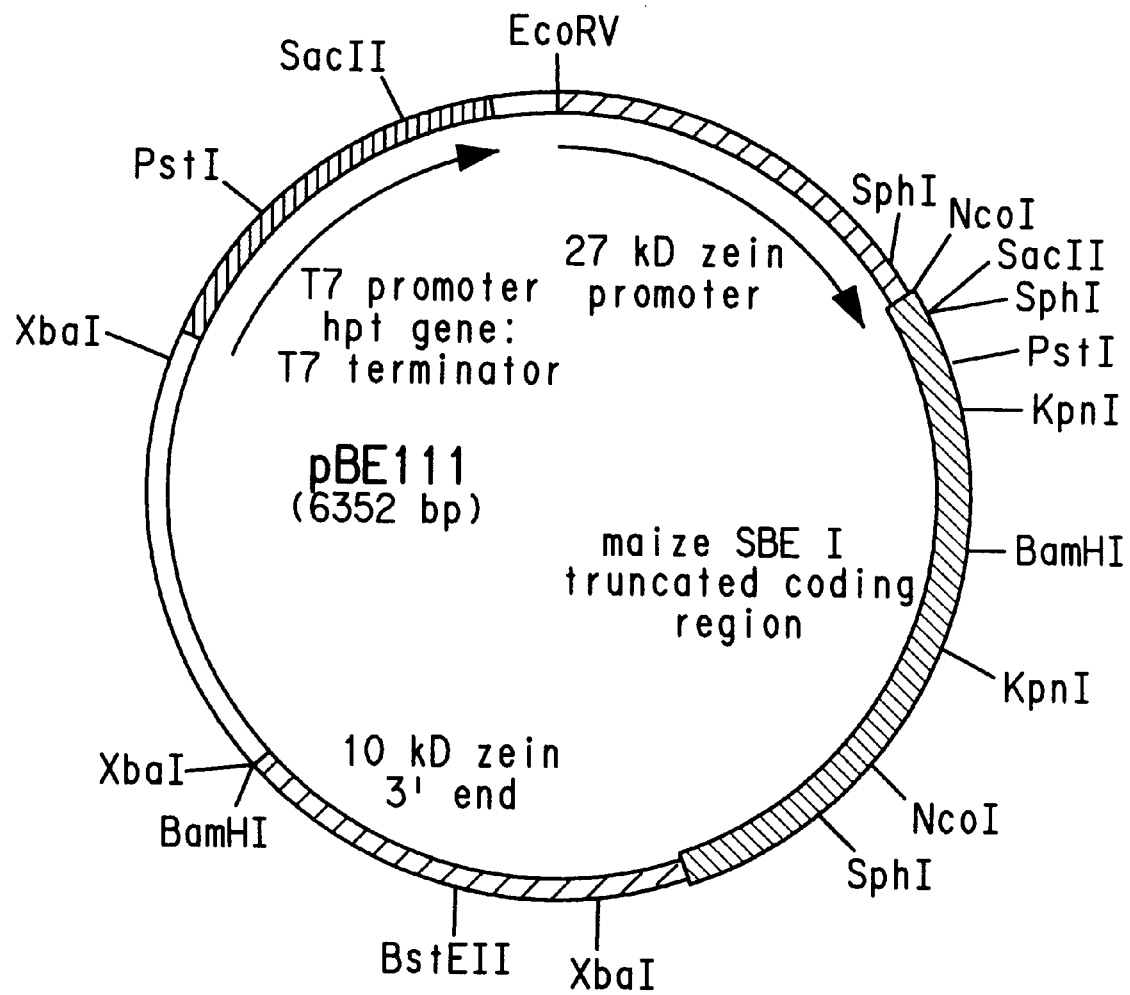

FIG. 15 is a restriction map of plasmid pBE111 comprising a 1810 bp cDNA fragment encoding a truncated SBEI joined in sense orientation with respect to the maize 27 kd zein promoter.

Figure 16:
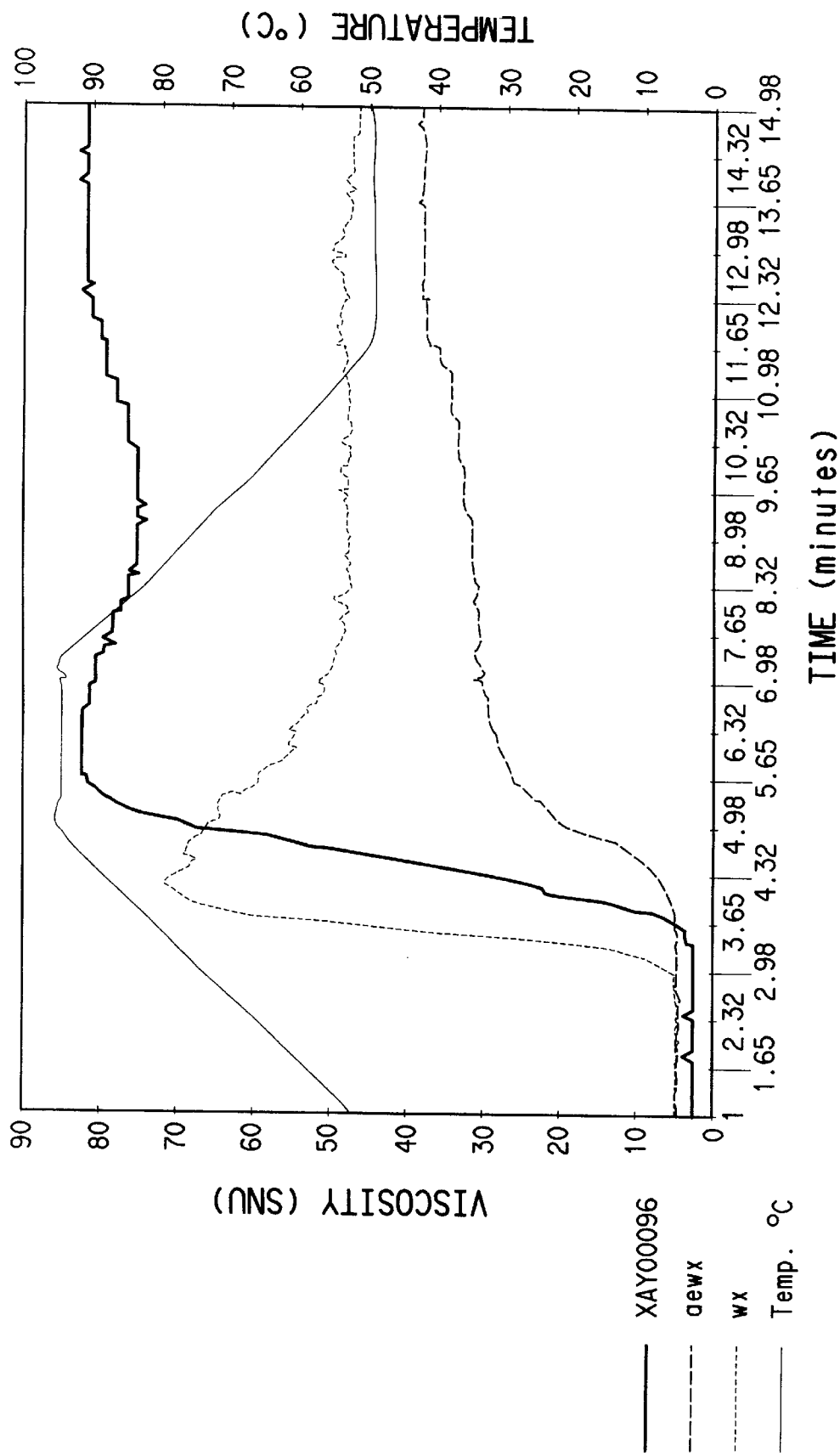

FIG. 16 compares RVA profiles of starch from waxy kernels, kernels homozygous for amylose extender (ae) and waxy and from kernels containing the pBE44 construct plus waxy. Viscosity, in stirring number units (SNU), and temperature (degrees Celsius) have been measured and plotted as a function of time (in minutes).

SEQ ID NO: 1 depicts the nucleotide sequence of the cDNA insert in plasmid pBE240 and the corresponding amino acid sequence of the entire corn SBEIIb enzyme.

SEQ ID NO:2 depicts the nucleotide sequence of the the 414 bp insert of pBE44.

SEQ ID NOS:3 and 4 depict the PCR primers BE41 and BE42 used for preparation of the 414 bp insert of pBE44.

SEQ ID NO:5 depicts the nucleotide sequence of the the 507 bp insert of pBE43.

SEQ ID NOS:6 and 7 depict the PCR primers BE39 and BE40 used for preparation of the 507 bp insert of pBE43.

SEQ ID NO:8 depicts the nucleotide sequence of the the 2165 bp insert of pBE45.

SEQ ID NO:9 depicts the nucleotide sequence of the the 2087 bp insert of pBE96.

SEQ ID NOS:10 and 11 depict the PCR primers BE14 and BE15 used for preparation of the probe used to isolate the 2772 bp insert of pBE65. BE15 (SEQ ID NO:11) was also used for the preparation of the insert in plasmid pBE79.

SEQ ID NO:12 depicts the nucleotide sequence of the the 2772 bp insert of pBE65.

SEQ ID NO:13 depicts the nucleotide sequence of the the 373 bp insert of pBE68.

SEQ ID NOS:14 and 15 depict the PCR primers BE43 and BE52 used for preparation of the 373 bp insert of pBE68.

SEQ ID NO:16 depicts the nucleotide sequence of the the 571 bp insert of pBE69.

SEQ ID NOS:17 and 18 depict the PCR primers BE46 and BE50 used for preparation of the 571 bp insert of pBE69.

SEQ ID NO:19 depicts the nucleotide sequence of the the 2487 bp insert of pBE72.

SEQ ID NO:20 depicts the nucleotide sequence of the the 1865 bp insert of pBE97.

SEQ ID NO:21 depicts the PCR primer BE67 used for preparation of the 805 bp insert of pBE83.

SEQ ID NOS:22 and 23 depict the PCR primers BE101 and BB3 used for preparation of a pBE110.

SEQ ID NO:24 depicts the nucleotide sequence of the the2565 bp insert of pBE110.

SEQ ID NO:25 depicts the nucleotide sequence of the the 1809 bp insert of pBEI111.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are incorporated by reference herein.

DETAILED DESCRIPTION OF THE INVENTION

In the context of this disclosure, a number of terms shall be utilized. As used herein, the term "starch" refers to a polysaccharide consisting of α-D-(1,4) glucan that may contain F@i a variable proportion of α-D-(1,6) branches. As used herein, the term "starch fine structure" refers to the molecular structure of a starch polymer, the presence, abundance and distribution of α-D-(1,6) bonds and the presence, abundance and length of both branched and unbranched α-D-(1,4) glucans in the polymer. Starch fine structure is described by amylopectin branch chain distribution, or by the relative proportion of amylose to amylopectin, or by the degree of polymerization of amylose. Alteration of any of these structural molecular components results in an altered starch fine structure. One, two or all three of these parameters may be altered independently of one another. The term "degree of polymerization" refers to the number of α-D-glucopyranose units in a molecule or designated portion of a molecule such as a branch chain of amylopectin.

As used herein, the term "branch chain distribution" refers to the distribution of α-1,4-linked glucan chains which is detected following isoamylase digestion of amylopectin and subsequent fractionation of the liberated branches by size exclusion chromatography. The branch chains may be classified according to their size and the number of crystalline regions (regions where many of the α-1,6-linkages (i.e., branch points) occur) which they span in the intact molecule. A chains are unbranched and span a single crystalline region. B1 chains also span a single crystalline region but are branched. B2, B3 and B4+ chains are branched and span 2, 3 and 4 or more crystalline regions, respectively (Hizukuri (1986) *Carbohydrate Res.* 147:342–347). The length of the repeating crystalline and amorphous units in the starch granule is quite regular with a repeat distance of 9 nm observed in starch from a wide variety of plant species (Jenkins (1993) Starch/Starke 45:417–420). Thus A and B1 chains are less than 9 nm in length B2 and B3 chains are between 18 and 27 nm in length and B4+ chains are greater than 36 nm.

As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which results in the production of a chemically equivalent amino acid at a given site, are contemplated; thus, a codon for the amino acid alanine, a hydrophobic amino acid, may be substituted by a codon encoding another hydrophobic amino acid residue such as glycine, valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity of the encoded products. Moreover, the skilled artisan recognizes that "essentially similar" sequences encompassed by this invention can also defined by their ability to hybridize, under stringent conditions (0.1X SSC, 0.1% SDS, 65° C.), with the sequences exemplified herein.

"Gene" refers to a nucleic acid fragment that encodes all or a portion of a specific protein, and includes regulatory sequences preceding (5' non-coding) and following (3' non-coding) the coding region. "Native gene" refers to the gene as found in nature with its own regulatory sequences. "Chimeric gene" refers to a gene comprising heterogeneous regulatory and coding sequences. "Endogenous gene" refers to the native gene normally found in its natural location in the genome. A "foreign gene" refers to a gene not normally found in the host organism but that is introduced by gene transfer. "Foreign gene" can also refer to a gene that is normally found in the host organism, but that is reintroduced at a location in the genome where it is not normally found, resulting in one or more additional copies of the coding sequence of an endogenous gene.

"Coding sequence" refers to a DNA sequence that codes for a specific protein and excludes the non-coding sequences.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the "primary transcript" or it may be a RNA sequence derived from posttranscriptional processing of the primary transcript. "Messenger RNA" (mRNA) refers to RNA that can be translated into protein by the cell. "cDNA" refers to a double-stranded DNA, one strand of which is complementary to and derived from mRNA by reverse transcription. "Sense" RNA refers to an RNA transcript that includes all or part of an mRNA. "Antisense RNA" refers to an RNA transcript that is complimentary to all or part of a target primary transcript or mRNA and that blocks the expression of a target gene by interfering with the processing, transport, and/or translation of its primary transcript or mRNA. The complimentarity of an antisense RNA may be with any part of the specific gene transcript, i.e., at the 5' non-coding sequence, 3' non-coding sequence, introns or the coding sequence. In addition, as used herein, anitsense RNA may contain regions of ribozyme sequences that may increase the efficacy of antisense RNA to block gene expression. "Ribozyme" refers to a catalytic RNA and includes sequence-specific endoribonucleases.

As used herein, suitable "regulatory sequences" refer to nucleotide sequences located upstream (5'), within, and/or downstream (3') to a coding sequence, which control the transcription and/or expression of the coding sequences. These regulatory sequences include promoters, translation leader sequences, transcription termination sequences, and polyadenylation sequences. In artificial DNA constructs, regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence which can stimulate promoter activity. It may be an innate element of the promoter or a heterologous element inserted to enhance the level and/or tissue-specificity of a promoter. "Constitutive" promoters refer to those that direct gene expression in substantially all tissues and demonstrate little temporal or developmental regulation. "Organ-specific" or "development-specific" promoters as referred to herein are those that direct gene expression almost exclusively in specific organs, such as leaves or seeds, or at specific developmental stages in an organ, such as in early or late embryogenesis, respectively.

The term "operably linked" refers to nucleic acid sequences on a single nucleic acid molecule which are associated so that the function of one is affected by the other. For example, a promoter is operably linked with a structural gene (i.e., a gene encoding a starch branching enzyme) when it is capable of affecting the expression of that structural gene (i.e., that the structural gene is under the transcriptional control of the promoter).

The term "expression", as used herein, is intended to mean the production of a functional end-product encoded by a gene. More particularly, "expression" refers to the transcription of the sense (mRNA) or the antisense RNA derived from the nucleic acid fragment(s) of the invention that, in conduction with the protein apparatus of the cell, results in altered levels of protein product. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression"

refers to the expression of a gene which is essentially similar to an endogenous gene and results in the supression of expression of both the ectopic and the endogenous gene. "Altered levels" refers to the production of gene product(s) in transgenic organisms in amounts or proportions that differ from that of normal or non-transformed organisms. The skilled artisan will recognize that the phenotypic effects contemplated by this invention, namely alteration of branch chain distribution in corn starch, can be achieved by alteration of the level of gene product(s) produced in transgenic organisms relative to normal or non-transformed organisms, including a reduction in gene expression mediated by antisense suppression or cosuppression, and enhancement of gene expression by overexpression.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Transformation" refers to the transfer of a nucleic acid fragment into the genome of a host organism, resulting in genetically stable inheritance. Host organisms containing the transformed nucleic acid fragments are referred to as "transgenic" organisms.

The term "pasting" refers to an irreversible physical change in starch granules or a suspension of starch granules characterized by swelling and hydration of granules, a rapid increase in viscosity of a suspension, and the formation of a sol from the suspension. This change is also known as cooking or gelatinization. The abbreviation "SNU" refers to the stirring number unit, approximately equal to 10 centipoise, which is a measure of viscosity. For conversion to SI units (pascal seconds), multiply centipoise by 1000, i.e., 1 PaSec=1000cp. Hence, 1 SNU=0.01 PaSec. The term "sol" refers to a fluid colloidal system. The term "viscosity" is a measure of the internal friction of a fluid that can be thought of as the consistency or thickness of a fluid.

This invention concerns the construction of transgenic corn plants wherein the expression of genes encoding enzymes involved in starch branching are modulated to effect a change in the branch chain distribution of the amylopectin, the relative proportion of amylose to amylopectin, and the degree of polymerization of amylose component of starch. Such modification of starch fine structure results in alteration of the physical properties of starch isolated from said transgenic corn plants. This alteration in the starch fine structure will lead to generation of novel starches possessing properties that are beneficial in food and industrial applications.

A number of genes encoding carbohydrate branching enzymes have been isolated and sequenced. These include glycogen branching enzymes from *Saccharomyces cerevisiae* (Thon et al. (1992) *J. Biol. Chem.* 267:15224–15228), *E. coli* (Baecker et al. (1986) *J. Biol. Chem.* 261:8738–8743), *Bacillus stearothermophilus* (Kiel et al. (1991) *Mol Gen. Genet.* 230:136–144), *Bacillus caldolyticus* (Kiel et al. (1992) DNA Seq. 3: 221–232), human (Thon et al. (1993) *J. Biol. Chem.* 268:7509–7513), *Aspergillus nidulans* (Kiel et al. (1990) *Gene* 89:77–84), *Streptomyces coelicolor* (EMBL accession number X73903), *Streptomyces aurofaciens* (Homerova, D. and Kormanec, J. (1994) *Biochem. Biophys. Acta* 1200:334–336) and starch branching enzymes from corn (Baba et al., (1991) *Biochem. Biophys. Res. Commun.* 181:87–94; Fisher et al. (1993) *Plant Physiol.* 102:1045–1046; Fisher et al. (1995) *Plant Physiol.* 108:1313–1314), pea (Burton et al. (1995) *Plant J.* 7:3–15), potato (Poulsen, P. and Kreiberg, J. D. (1993) *Plant Physiol.* 102:1053–1054), cassava (Salehuzzaman et al. (1992) *Plant Mol. Biol.* 20:809–819), rice (Kawasaki et al. (1993) *Mol. Gen. Genet.* 237:10–16; Mizuno et al. (.93) *J. Biol. Chem.* 268:19084–19091) and *Arabidopsis thaliana* (EMBL accession numbers U18817 and U22428). Preferred among these are the corn starch branching enzyme genes. These genes can be isolated by techniques routinely employed by the skilled artisan for isolation of genes when the nucleotide sequence of the desired gene is known, or when the sequence of a homologous gene from another organism is known. Sequence information about the desired gene can be used to prepare oligonucleotide probes for identification and isolation of the entire branching enzyme gene from an appropriate genetic library. This library may be a genomic library, wherein the coding region may be contained on a single DNA fragment or may be contained on several distinct DNA fragments. Moreover, two or more exons encoding the branching enzyme may be separated by one or more introns. Alternatively, the library may be a cDNA library wherein the likelihood of isolating a cDNA clone comprising the entire coding region as one contiguous sequence is greater. In either instance, the appropriate clone (s) can be identified by DNA-DNA hybridization with probes corresponding to one or more portions of the desired genes. Alternatively, oligonucleotide primers can be prepared and employed as PCR primers in order to amplify and subsequently isolate all or part of the branching enzyme coding region from genomic DNA, or from the genomic or cDNA libraries described above.

Several different assays can be used to measure branching enzyme activity. In the phosphorylase stimulation assay (Boyer, C. D. and Preiss, J. (1978) *Carbohydr. Res.* 61:321–334), activity is measured indirectly by following the ability of branching enzymes to stimulate formation of α-D-glucan from glucose-l-phosphate by phosphorylase a. The iodine stain assay is based upon the decrease in the absorbance of a glucan-polyiodide complex which occurs as a result of the branching of amylose or amylopectin (ibid). In the third assay, the branch linkage assay, reduced amylose is utilized as the substrate and enzyme activity is followed by measuring the generation of reducing ends following digestion of the product with isoamylase (Takeda et al. (1993) *Carbohydr. Res.* 240:253–262). Guan and Preiss ((1993) *Plant Physiol.* 102:1269–1273) have used the iodine stain and the branch linkage assay, to differentiate the catalytic properties of the three starch branching enzymes in maize. While SBEI exhibits higher activity in branching amylose, SBEIIa and SBEIIb show higher rates of branching with an amylopectin substrate. The isoforms may be further differentiated on the basis of the length of α-1,4-glucan chain that is transferred: SBEI preferentially transfers longer glucan chains while SBEIIa and SBEIIb show a preference in the transfer of shorter chains. Thus, assays which measure enzyme activity may be used to assign a functional activity to proteins which, on the basis of homology at the amino acid level or hybridization at the DNA level, have been identified as starch or glycogen branching enzymes. They may additionally be used to characterize starch or glycogen branching enzymes which have been subjected to mutagenesis schemes designed to identify or alter amino acid residues which play a role in determining catalytic properties. Furthermore, using the findings of Guan and Preiss (Id.), native or mutagenized enzymes may be classified as SBEI or SBEII-like on the basis of substrate or product preferences.

In order to alter the starch fine structure in corn, a chimeric gene. is constructed wherein expression of the gene encoding the starch branching enzyme is under the control of regulatory elements suitable to expression of the gene 1) in desired plant tissues, 2) at stages of development that provide the maximum desired effect, and 3) at levels of gene expression that result in alteration of starch branching enzyme function such that expression affects a measurable and significant change in starch fine structure.

The expression of foreign genes in plants is well-established (De Blaere et al. (1987) Meth. Enzymol. 143:277–291). Proper level of expression of sense or anti-sense branching enzyme genes in corn may require the use of different chimeric genes utilizing different regulatory elements. Moreover, effective modulation of endogenous branching enzyme gene expression by cosupression or anti-sense supression may require construction of chimeric genes comprising different regions of the branching enzyme sense or antisense sequences. The well-known unpredictability of the cosuppression and antisense techniques indicates that even while using different genetic constructs, multiple plants may have to be screened in order to identify those with the desired phenotype.

Promoters utilized to drive gene expression in transgenic plants can be derived from many sources so long as the chosen promoter(s) have sufficient transcriptional activity to accomplish the invention by expressing translatable mRNA or antisense RNA in the desired host tissue. For example, promoters for expression in a wide array of plant organs include those directing the 19S and 35S transcripts in Cauliflower mosaic virus (Odell et al. (1985) Nature 313:810–812; Hull et al. (1987) Virology 86:482–493), small subunit of ribulose 1,5-bisphosphate carboxylase (Morelli et al. (1985) Nature 315:200–204; Broglie et al. (1984) Science 224:838–843; Hererra-Estrella et al. (1984) Nature 310:115–120; Coruzzi et al. (1984) EMBO J. 3:1671–1679; Faciotti et al. (1985) Bio/Technology 3:241 and chlorophyll a/b binding protein (Lamppa et al. (1986) Nature 316:750–752).

Depending upon the application, it may be desirable to select promoters that are specific for expression in one or more organs of the plant. Examples include the light-inducible promoters of the small subunit of ribulose 1,5-bisphosphate carboxylase, if the expression is desired in photosynthetic organs, or promoters active specifically in seeds.

Preferred promoters are those that allow expression specifically in seeds. This may be especially useful, since seeds are the primary location of long-term starch accumulation. In addition, seed-specific expression may avoid any potential deleterious effects that branching enzyme modulation may have on non-seed organs. Examples of seed-specific promoters include, but are not limited to, the promoters of seed storage proteins. The seed storage proteins are strictly regulated, being expressed almost exclusively in seeds in a highly organ-specific and stage-specific manner (Higgins et al. (1984) Ann. Rev. Plant Physiol. 35:191–221; Goldberg et al. (1989) Cell 56:149–160; Thompson et al. (1989) BioEssays 10:108–113). Moreover, different seed storage proteins may be expressed at different stages of seed development.

There are currently numerous examples for seed-specific expression of seed storage protein genes in transgenic plants. These include genes from monocotyledonous plants such as for barley β-hordein (Marris et al. (1988) Plant Mol. Biol 10:359–366) and wheat glutenin (Colot et al. (1987) EMBO J. 6:3559–3564). Moreover, promoters of seed-specific genes, operably linked to heterologous coding sequences in chimeric gene constructs, also maintain their temporal and spatial expression pattern in transgenic plants. Such examples include linking either the Phaseolin or Arabidopsis 2S albumin promoters to the Brazil nut 2S albumin coding sequence and expressing such combinations in tobacco, Arabidopsis, or Brassica napus (Altenbach et al. (1989) Plant Mol. Biol. 13:513–522; Altenbach et al. (1992) Plant Mol. Biol. 18:235–245; De Clercq et al. (1990) Plant Physiol. 94:970–979), bean lectin and bean β-phaseolin promoters to express luciferase (Riggs et al. (1989) Plant Sci. 63:47–57), and wheat glutenin promoters to express chloramphenicol acetyl transferase (Colot et al. (,87) EMBO J. 6:3559–3564).

Of particular use in the expression of the nucleic acid fragment(s) of the invention will be promoters from several extensively characterized corn seed storage protein genes such as endosperm-specific promoters from the 10 kD zein gene (Kirihara et al. (1988) Gene 71:359–370), the 15 kD zein gene (Hoffinan et al. (1987) EMBO J. 6:3213–3221; Schernthaner et al. (1988) EMBO J. 7:1249–1253; Williamson et al. (1988) Plant Physiol. 88:1002–1007), the 27 kD zein gene (Prat et al. (1987) Gene 52:51–49; Gallardo et al. (1988) Plant Sci. 54:211–281), and the 19 kD zein gene (Marks et al. (1985) J. Biol Chem. 260:16451–16459). The relative transcriptional activities of these promoters in corn have been reported (Kodrzyck et al. (1989) Plant Cell 1:105–114) providing a basis for choosing a promoter for use in chimeric gene constructs for corn. Moreover, promoters that drive the expression of genes encoding enzymes involved in starch biosynthesis may be used in the practice of this invention. These include the 5' regulatory sequences of the sucrose synthase (Yang, N.-S. and Russell, D. (1990) Proc. Natl. Acad. Sci. 87:4144–4148) and the waxy or granule-bound starch synthase I (Unger, et al. (1991) Plant Physiol. 96:124) genes. Promoter elements may be derived from other starch synthase (granule-bound and soluble isoforms) genes when these become available, and from the sh2 (Bhave et al. (1990) Plant Cell 2:581–588) and bt2 (Bae et al. (1990) Maydica 35:317–322) genes whose products constitute the enzyme ADP-glucose pyrophosphorylase. The isolation of genomic clones encoding the starch branching enzyme genes may be accomplished using the corresponding cDNA clones (Baba et al. (1991) Biochem. Biophys. Res. Commun. 181:87–94; Fisher et al. (1993) Plant Physiol. 102:1045–1046) as hybridization probes. These would provide a useful starting point for the isolation of promoter fragments of these genes. For assembly of SBE constructs, the upstream sequences may be donated by the cognate SBEII gene or, alternatively, by the SBEI gene.

It is envisioned that the introduction of enhancers or enhancer-like elements into other promoter constructs will also provide increased levels of primary transcription to accomplish the invention. These would include viral enhancers such as that found in the 35S promoter (Odell et al. (1988) Plant Mol Biol. 10:263–272), enhancers from the opine genes (Fromm et al. (1989) Plant Cell 1:977–984), or enhancers from any other source that result in increased transcription when placed into a promoter operably linked to the nucleic acid fragment of the invention.

Introns isolated from the maize Adh-1 and Bz-1 genes (Callis et al. (1987) Genes Dev. 1:1183–1200), and intron 1 and exon 1 of the maize Shrunken-1 (sh-1) gene (Maas et al. (1991) Plant Mol. Biol. 16:199–207) may also be of use to increase expression of introduced genes. Results with the first intron of the maize alcohol dehydrogenase (Adh-1) gene indicate that when this DNA element is placed within the transcriptional unit of a heterologous gene, mRNA levels can be increased by 6.7-fold over normal levels. Similar levels of intron enhancement have been observed using intron 3 of a maize actin gene (Luehrsen, K. R. and Walbot, V. (1991) *Mol. Gen. Genet.* 225:81–93). Enhancement of gene expression by Adhl intron 6 (Oard et al. (1989) *Plant Cell Rep* 8:156–160) has also been noted. Exon 1 and intron 1 of the maize sh-l gene have been shown to individually increase expression of reporter genes in maize suspension cultures by 10 and 100-fold, respectively. When used in combination, these elements have been shown to produce up to 1000-fold stimulation of reporter gene expression (Maas et al. (1991) *Plant Mol. Biol.* 16:199–207).

Any 3' non-coding region capable of providing a polyadenylation signal and other regulatory sequences that may be required for proper expression can be used to accomplish the invention. This would include the 3' end from any storage protein such as the 3' end of the 10kd, 15kd, 27kd and alpha zein genes, the 3' end of the bean phaseolin gene, the 3' end of the soybean b-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions (for example, see Ingelbrecht et al. (1989) *Plant Cell* 1:671–680).

Various methods of introducing a DNA sequence (i.e., of transforming) into eukaryotic cells of higher plants are available to those skilled in the art (see EPO publications 0 295 959 A2 and 0 138 341 A1). Such methods include high-velocity ballistic bombardment with metal particles coated with the nucleic acid constructs (see Klein et al. (1987) *Nature* (London) 327:70–73, and see U.S. Pat. No. 4,945,050), as well as those based on transformation vectors based on the Ti and Ri plasmids of Agrobacterium spp., particularly the binary type of these vectors. Ti-derived vectors transform a wide variety of higher plants, including monocotyledonous and dicotyledonous plants, such as soybean, cotton and rape (Pacciotti et al. (1985) *Bio/Technology* 3:241; Byrne et al. (1987) *Plant Cell, Tissue and Organ Culture* 8:3; Sukhapinda et al. (1987) *Plant Mol. Biol.* 8:209–216; Lorz et al. (1985) *Mol. Gen. Genet.* 199:178–182; Potrykus et al. (1985) *Mol. Gen. Genet.* 199:183–188).

Other transformation methods are available to those skilled in the art, such as direct uptake of foreign DNA constructs (see EPO publication 0 295 959 A2), and techniques of electroporation (see Fromm et al. (1986) *Nature* (London) 319:791–793). Once transformed, the cells can be regenerated by those skilled in the art. Also relevant are several recently described methods of introducing nucleic acid fragments into commercially important crops, such as rapeseed (see De Block et al. (1989) *Plant Physiol.* 91:694–701), sunflower (Everett et al., (1987) *Bio/Technology* 5:1201–1204), soybean (McCabe et al. (1988) *Bio/Technology* 6:923–926; Hinchee et al. (1988) *Bio/Technology* 6:915–922; Chee et al. (1989) *Plant Physiol.* 91:1212–1218; Christou et al. (1989) *Proc. Natl. Acad. Sci. USA* 86:7500–7504; EPO Publication 0 301 749 A2), and corn (Gordon-Kamm et al. (1990) *Plant Cell* 2:603–618; Fromm et al. (1990) *Bio/Technology* 8:833–839).

One skilled in the art is familiar with still other means for the production of transgenic maize plants including introduction of DNA into protoplasts and regeneration of plants from said protoplasts (Omirulleh et al. (1993) *Plant Mol. Biol.* 21:415–423), electroporation of intact tissues (D'Hulluin et al. (1992) *Plant Cell* 4:1495–1505; Laursen et al. (1994) *Plant Mol. Biol.* 24:51–61), silica carbide mediated fiber transformation of maize 0 cells (Kaeppler et al. (1992) Theor. Appl. *Genet.* 84:560–566; Frame et al. (1994) *Plant J.* 6:941–948). In addition to the method of particle bombardment of maize callus cells described above, one skilled in the art is familiar with particle bombardment of maize scutellar or suspension cultures to yield fertile transgenic plants (Koziel et al. (1993) *Bio/Technology* 11:194–200; Walters et al. (1992) *Plant Mol. Biol.* 18:189–200).

Once transgenic plants are obtained by one of the methods described above, it will be necessary to screen individual transgenics for those that most effectively display the desired phenotype. It is well known to those skilled in the art that individual transgenic plants carrying the same construct may differ in expression levels; this phenomenon is commonly referred to as "position effect". For example, when the construct in question is designed to express higher levels of the gene of interest, individual plants will vary in the amount of the protein produced and thus in enzyme activity; this in turn will effect the phenotype.

The person skilled in the art will know that special considerations are associated with the use of antisense or cosuppresion technologies in order to reduce expression of particular genes. U. S. Pat. Nos. 5,190,931, 5,107,065 and 5,283,323 have taught the feasibility of these techniques, but it is well known that their efficiency is unpredictable. In either case, in order to save time, the person skilled in the art will make multiple genetic constructs containing one or more different parts of the gene to be suppressed, since the art does not teach a method to predict which will be most effective for a particular gene. Furthermore, even the most effective constructs will give an effective suppression phenotype only in a fraction of the individual transgenic lines isolated. For example, WO93/11245 and WO94/11516 teach that when attempting to suppress the expression of fatty acid desaturase genes in canola, actual suppression was obtained in less than 1% of the lines tested. In other species the percentage is somewhat higher, but in no case does the percentage reach 100.

This should not be seen as a limitation on the present invention, but instead as practical matter that is appreciated and anticipated by the person skilled in this art. Accordingly, skilled artisan will develop methods for screening large numbers of transformants. The nature of these screens will generally be chosen on practical grounds, and is not an inherent part of the invention. In the instant case, for example, one can screen by looking for changes in starch phenotype using chromatography to determine relative proportions of amylose to amylopectin, amylopectin branch chain distribution, RVA analysis (as is done in the examples), or other means. One could equally use antibodies specific for the protein encoded by the gene being suppressed, or one could establish assays that specifically measure enzyme activity. A preferred method will be one which allows large numbers of samples to be processed rapidly, since it will be expected that the majority of samples will be negative.

Plants that are identified to have the altered starch fine structure in the grain present unique genetic material which provide advantages over traditional corn lines and known starch mutants. Use of lines with inhibited expression of SBE isoforms in corn breeding provide a dominant trait that can simplify and speed the breeding process. Known starch mutants can be used but they are often recessive and present more complications. Further, the use of antisense or cosuppression to inhibit SBE isoforms leads to variable levels of inhibition due to chromosomal position effects. The resulting variable levels of SBE activities would lead to a wide range of phenotypes that is not possible using traditional mutants which can result in a limited dosage series of a mutant allele in corn endosperm. Additional unique and potentially valuable starch fine structures will result from crossing the newly developed corn lines with inhibited SBE with each other and/or known starch mutants such as wx or ae.

EXAMPLES

The present invention is further defined in the following examples. It will be understood that the examples are given for illustration only and the present invention is not limited to uses described in the examples. The present invention can be used to generate transgenic corn plants whose altered starches may be used for any purpose where its properties are useful such as in, but not limited to, foods, paper, plastics, adhesives, or paint. From the above discussion and the following examples, one skilled in the art can ascertain, and without departing from the spirit and scope thereof, can make various changes and modifications of the invention to adapt it to various usages and conditions. All such modifications are intended to fall within the scope of the intended claims.

Example 1

Figure 1:
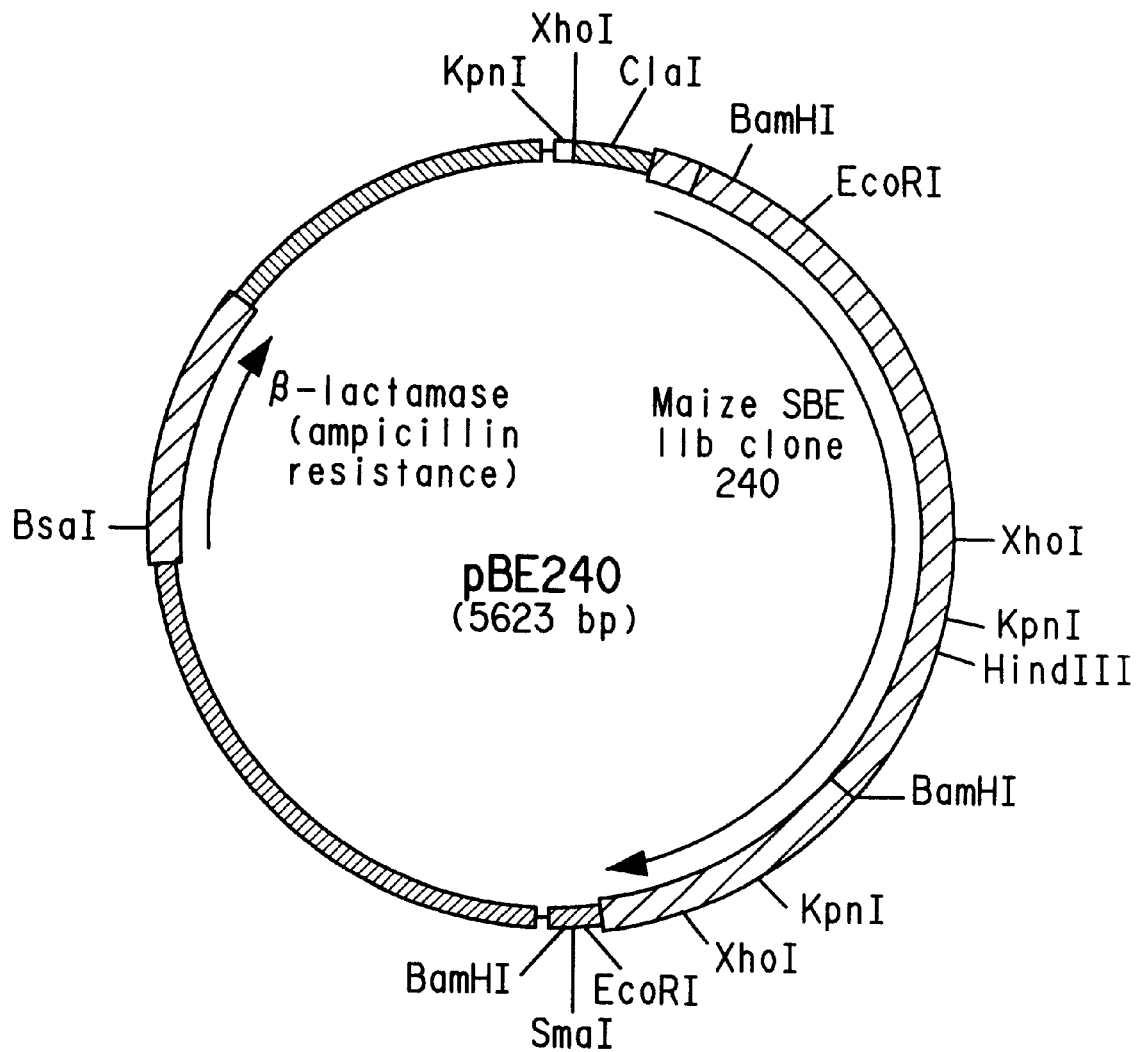

Preparation of Transzenic Corn Expressing a 3' Antisense Transcript of Corn Starch Branching Enzyme IIb The cDNA insert of plasmid clone pBE240 was used as the starting point in the assembly of DNA constructs designed to achieve suppression of SBEIIb expression in transgenic corn plants. The cDNA clone pBE240, encoding corn starch branching enzyme IIb (hereinafter SBEIIb), has been deposited under the terms of the Budapest Treaty at ATCC (American Type Culture Collection, 10801 University Boulevard, Manassas, Va. 20110–2209), and bears the following accession number: ATCC 97365. pBE 240 (FIG. 1) comprises a 2.7 kbp EcoRI-XhoI fragment isolated from a corn cDNA library, inserted into the plasmid vector pbluescript™SK+(Stratagene). The insert (SEQ ID NO:1) consists of 78 bp of 5' untranslated DNA, a 2397 bp open reading frame encoding the corn SBEIIb coding region and 190 bp of 3' untranslated DNA.

Preparation of the Expression Vector Encoding the 3' Antisense Construct

Figure 2:
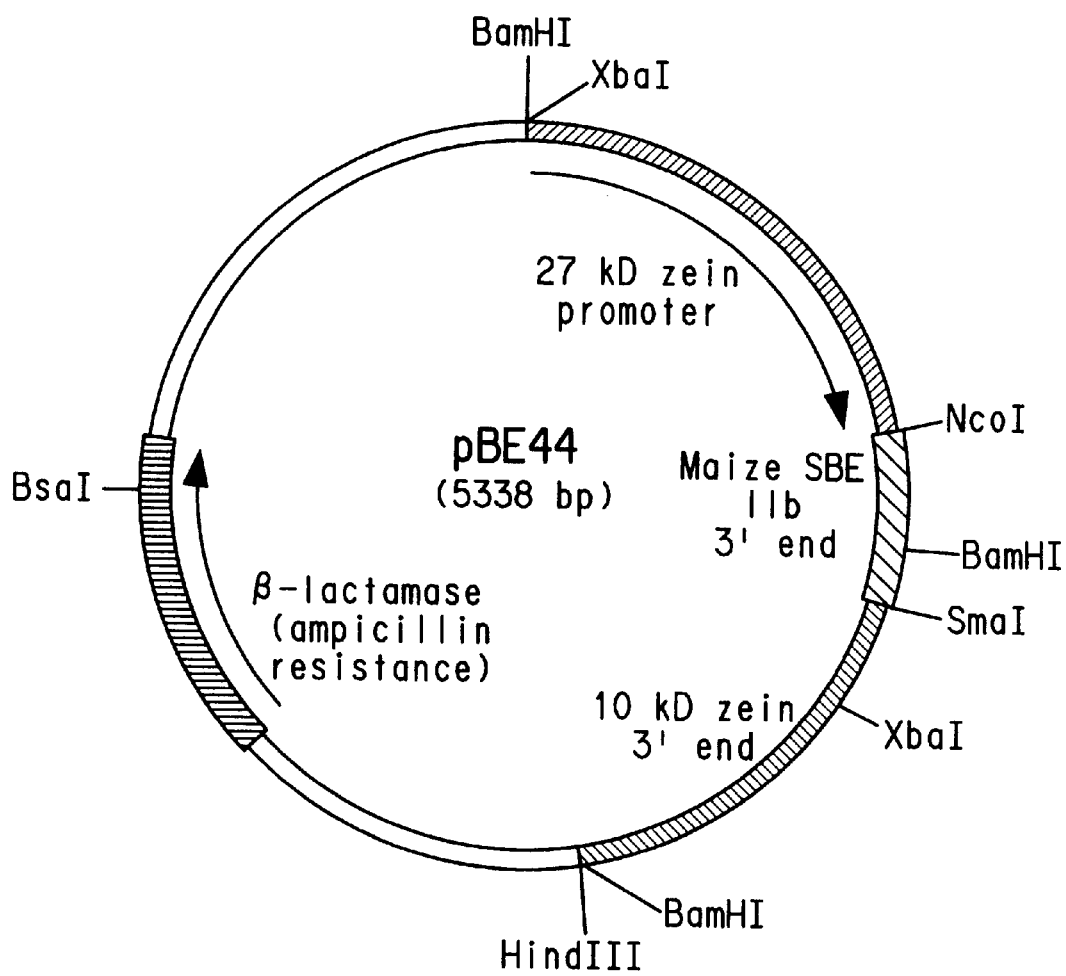
FIG. 2 is a restriction map of plasmid pBE44 comprising a 414 bp 3' fragment of the insert of pBE240 in antisense orientation with respect to the corn 27 kd zein promoter.

The chimeric gene inserted into plasmid construct pBE44 (FIG. 2) comprises a 3' fragment of the SBEIIb cDNA in antisense orientation with respect to the maize 27 kD zein promoter that is located 5' to the SBEIIb fragment, and the 10 kD zein 3' end that is located 3' to the SBEIIb fragment. The SBEIIb fragment of this construct was generated by polymerase chain reaction (PCR) of pBE240 using appropriate oligonucleotide primers.

These primers were synthesized on a Beckman Oligo 1000™ DNA Synthesizer. The 414 bp fragment of pBE44 (SEQ ID NO:2) was generated using the oligonucleotide pair BE41 (SEQ ID NO:3) and BE42 (SEQ ID NO:4):

BE41
    5'-GAATTCCCGGGGTGTTCAACTTCCACTGC-3' (SEQ ID NO:3)

BE42 5'-GAATTCCATGGGACACCTTGAAGGTCTT-3' (SEQ ID NO:4).

Figure 3:
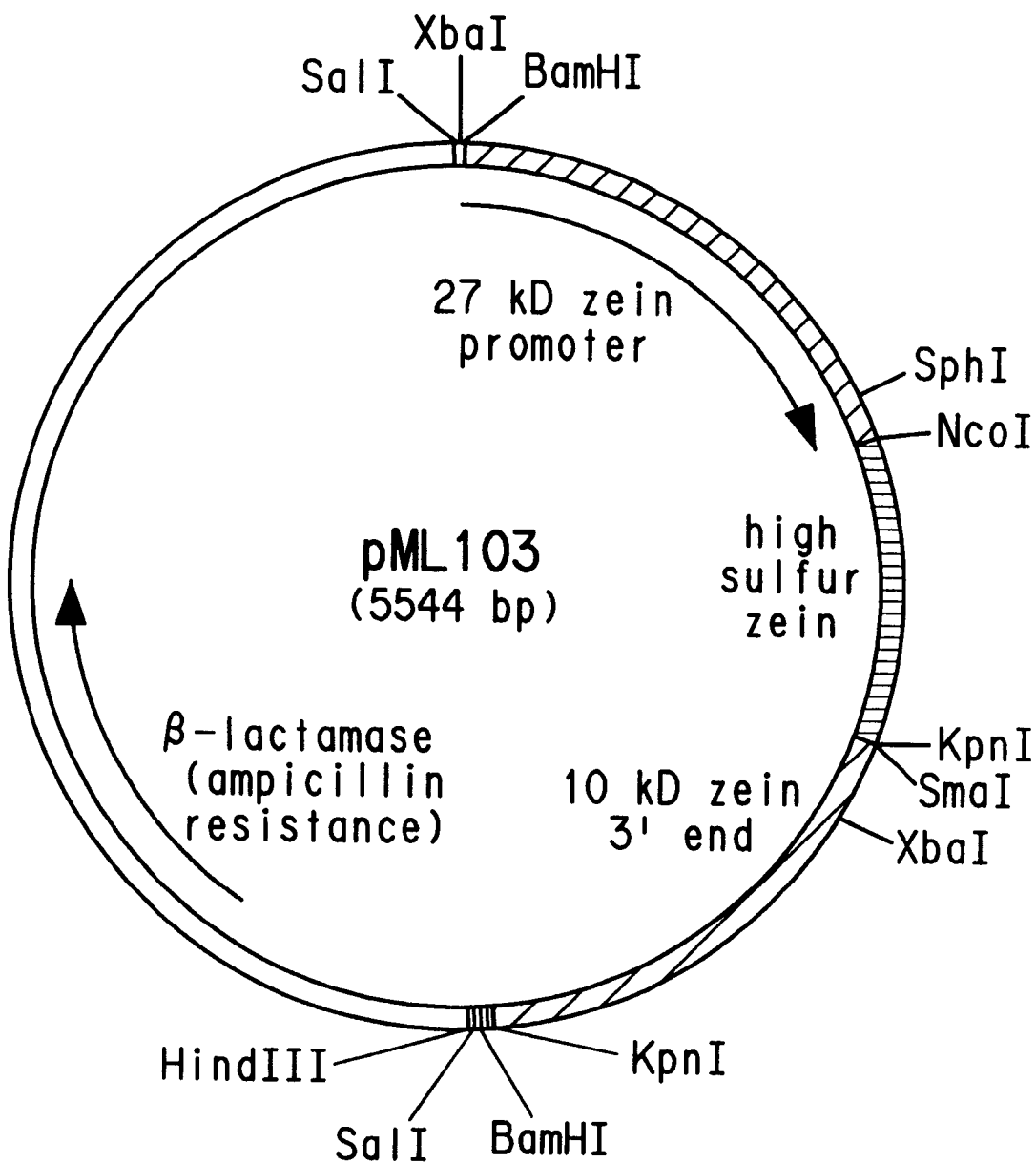
FIG. 3 is a restriction map of plasmid pML103, used as an intermediate cloning vehicle in construction of chimeric genes of the instant invention.

Cloning sites (NcoI or SmaI) were incorporated into the oligonucleotides to provide antisense orientation of the DNA fragments when inserted into the digested vector pML103 as described below. Amplification was performed in a 100 ml volume in a standard PCR mix consisting of 0.4 mM of each oligonucleotide and 0.3 pM of pBE240 in 10 mM Tris-HCl, pH 8.3, 50 mM KCl, 1.5 mM MgCl$_2$, 0.001% w/v gelatin, 200 mM dGTP, 200 mM dATP, 200 mM dTTP, 200 mM dCTP and 0.025 unit Amplitaq™ DNA polymerase. Reactions were carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. The amplified DNA was digested with restriction enzymes NcoI and SmaI and fractionated on a 0.7% low melting point agarose gel in 40 mM Tris-acetate, pH 8.5, 1 mM EDTA. The appropriate band was excised from the gel, melted at 68° C. and combined with a 4.9 kb NcoI-SmaI fragment of the plasmid pML103 (FIG. 3). Plasmid pML103 has been deposited under the terms of the Budapest Treaty at ATCC (American Type Culture Collection, 10801 University Boulevard, Manassas, Va. 20110–2209), and bears the following accession number: ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA were ligated at 15° C. overnight, essentially as described (Sambrook, J., Fritsch, E. F. and Maniatis, T. (1989) Molecular Cloning, Cold Spring Harbor Laboratory Press, New York; hereinafter "Maniatis"). The ligated DNA was used to transform *E. coli* XL1-Blue (Epicurian Coli XL-1 Blue™; Stratagene). Bacterial transformants were screened by restriction enzyme digestion of plasmid DNA and limited nucleotide sequence analysis using the dideoxy chain termination method (Sequenase™ DNA Sequencing Kit; U. S. Biochemical). The resulting plasmid construct, pBE44, comprises a chimeric gene encoding, in the 5' to 3' direction, the maize 27 kD zein promoter, a 3' fragment of the corn SBEIIb cDNA, and the 10 kD zein 3' region.

Larger quantities of pBE44 plasmid DNA were prepared by the alkaline lysis method, followed by purification by CsCl density gradient centrifugation.

Transformation of Corn with the 3' Antisense Construct

Immature corn embryos were dissected from developing caryopses derived from crosses of the inbred corn lines H99 and LH132. The embryos were isolated 10 to 11 days after pollination when they were 1.0 to 1.5 mm long. The embryos were placed with the axis-side facing down and in contact with agarose-solidified N6 medium (Chu et al. (1975), *Sci. Sin. Peking* 18:659–668). The embryos were kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant was cultured on N6 medium and sub-cultured on this medium every 2 to 3 weeks.

Figure 4:
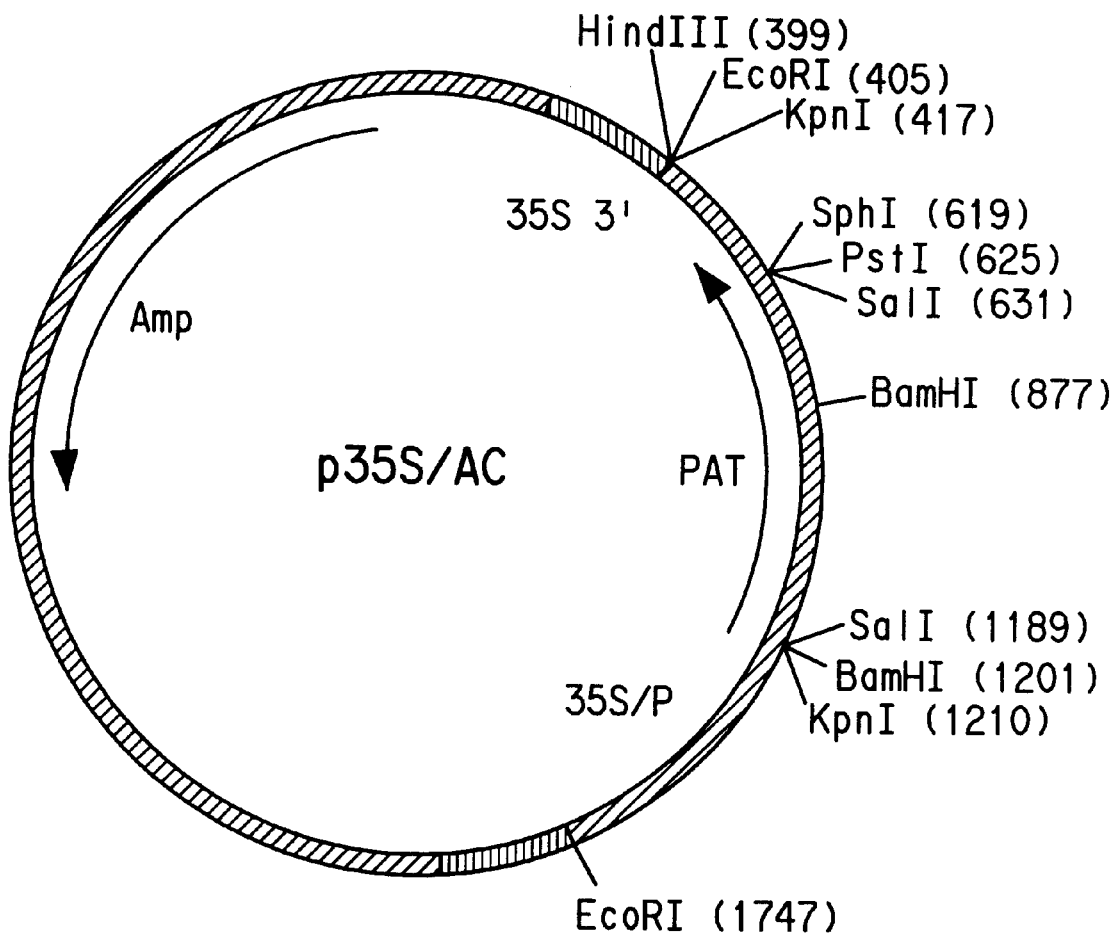
FIG. 4 is a restriction map of plasmid p35/Ac encoding, inter alia, phosphinothricin acetyl trasnsferase. Introduction of this plasmid into plant cells and tissues confers resistance to herbicidal glutamine synthetase inhibitors such as phosphinothricin on the transformed plant cells and tissues.

The plasmid, p35S/Ac (FIG. 4; obtained from Dr. Peter Eckes, Hoechst Ag, Frankfurt, Germany) was used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987), *Nature* 327:70–73) was used to transfer genes to the callus culture cells. Gold particles (1 μm in diameter) were coated with DNA using the following technique. Plasmid DNAs (10 μg of p35S/Ac and 10 μg of pBE44) were added to 50 μl of a suspension of gold particles (60 mg per ml). Calcium chloride (50 μl of a 2.5 M solution) and spermidine free base (20 μl of a 1.0 M solution) were added to the particles. The suspension was vortexed during the addition of these solutions. After 10 minutes, the tubes were briefly centrifuged (5 sec at 15,000 rpm) and the supernatant removed. The particles were resuspended in 200 μl of absolute ethanol, centrifuged again and the supernatant removed. The ethanol rinse was performed again and the particles resuspended in a final volume of 30 μl of ethanol. An aliquot (5 μl) of the DNA-coated gold particles was placed in the center of a Kapton™ flying disc (Bio-Rad Labs). The particles were accelerated into the corn tissue with a Biolistic™ PDS-1000/ He (Bio-Rad Instruments, Hercules Calif.), using a helium pressure of 1000 psi, a gap distance of 0.5 cm and a flying distance of 1.0 cm.

For bombardment, the embryogenic tissue was placed on filter paper over agarose-solidified N6 medium. The tissue was arranged as a thin lawn and covered a circular area of about 5 cm in diameter. The petri dish containing the tissue was placed in the chamber of the PDS-1000/He approximately 8 cm from the stopping screen. The air in the chamber was then evacuated to a vacuum of 28 inches of Hg. The macrocarrier was accelerated with a helium shock wave using a rupture membrane that bursts when the He pressure in the shock tube reaches 1000 psi.

Seven days after bombardment the tissue was transferred to N6 medium that contained glufosinate (2 mg per liter) and lacked casein or proline. The tissue continued to grow slowly on this medium. After an additional 2 weeks the tissue was transferred to fresh N6 medium containing glufosinate. After 6 weeks, areas of about 1 cm in diameter of actively growing callus were identified on some of the plates containing the glufosinate-supplemented medium. These calli continued to grow when sub-cultured on the selective medium.

Plants were regenerated from the transgenic callus by first transferring clusters of tissue to N6 medium supplemented with 0.2 mg per liter of 2,4-D. After two weeks the tissue was transferred to regeneration medium (Fromm et al. (1990) *Bio/Technology* 8:833–839). A total of 9 corn plants were regenerated from a single transformation experiment using the pBE44 construct.

Molecular Analysis of Transgenic Corn Plants Containing the 3' Antisense Construct Total DNA was isolated from leaf tissue of plants regenerated from the transformation experiment using pBE44 essentially as described by Dellaporta et al. (Dellaporta et al. (1983) *Plant Mol. Biol. Rep.* 1 (4:1921). Lyophillized tissue was frozen in liquid nitrogen, ground to a fine powder and suspended in a buffer consisting of 100 mM Tris-HCI, pH 8.0, 50 mM EDTA, 10 mM b-mercaptoethanol and 0.5 M NaCl. Cells were lysed by the addition of SDS to 1% and the DNA precipitated with isopropanol. The dissolved DNA was treated with DNase-free RNase and then re-precipitated with iso-propanol. The isolated DNAs were dissolved in 10 mM Tris-HCl, pH 8.0, 1 mM EDTA and stored at −20° C. until use.

For Southern blot analysis, 5 mg of isolated DNA was digested with restriction enzyme (10 units/mg DNA) in the appropriate buffer for approximately 6 hrs at 37° C. The restricted DNA was loaded onto a 0.8% agarose gel in Tris-borate-EDTA buffer (Maniatis) and electrophoresed at 40 V overnight. Following denaturation and neutralization, the DNA was transferred to an Immobilon™ membrane (Millipore Corporation) using 10× SSC. The Immobilon™ membrane was pre-hybridized at 65° C. in an aqueous buffer system consisting of 6× SSPE, 5× Denhardt's reagent, 0.5% SDS and 100 mg/mL denatured salmon sperm DNA as described (Maniatis). The SBE fragment of pBE44 was labeled by nick translation (BRL Nick Translation Kit) and added to the above buffer supplemented with 5% dextran sulfate at a level of $1-2 \times 10^6$ cpm/ml. Hybridization was allowed to proceed at 65° C. for 18 h. The membrane was sequentially washed with 2× SSC, 0.1% SDS for 15 minutes at room temperature, 1× SSC, 0.1% SDS for 15 minutes at room temperature and 0.1× SSC, 0.5% SDS for 15 minutes at 50° C. Washed membranes were exposed to DuPont Reflection™ film with an intensifying screen at −80° C.

For Northern blot analysis, total RNA was isolated from kernels harvested 20–22 days after pollination (DAP). Approximately 10 kernels per plant were pooled and frozen in liquid nitrogen. The frozen tissue was ground to a fine powder. A mixture of phenol-chloroform-isoamyl alcohol (24:24: 1; 3 ml) was added and the tissue slurry briefly homogenized by hand. 4.5 mL extraction buffer (1 M Tris-HCl, pH 9.0, 1% SDS, 5% β-mercaptoethanol) was mixed in and the suspension was centrifuged (4° C., 7500 rpm, SS-34) to remove debris. The supernatant was extracted with phenol-chloroform-isoamyl alcohol and the nucleic acids collected by ethanol precipitation. RNA was isolated from the dissolved pellet by selective precipitation with 0.2 M LiCl followed by a second precipitation with ethanol. RNA was dissolved in sterile water and stored at −80° C. prior to use. RNA concentration was calculated by measuring the absorption of solutions at 260 nm (assuming that $A_{260}=1$ corresponds to 40 mg/mL).

Total RNA was denatured by reaction with glyoxal and fractionated on a 1% agarose gel in 10 mM sodium phosphate buffer, pH 7.0 (Maniatis). RNA was transferred to a Hybond™ nylon membrane using 20× SSC as the transfer medium and then fixed to the solid support by irradiation in a WV Stratalinker™ (Stratagene). Blots were pre-hybridized at 42° C. for 18 h. in a buffer consisting of 50% formamide, 6× SSPE, 5× Denhardt's, 0.5% SDS, 100 mg/mL denatured salmon sperm DNA. Hybridization was carried out at 42° C. for 18–24 h in the same buffer supplemented with 5% dextran sulfate and containing $1-2 \times 10^6$ cpm/mL denatured, nick translated probe. Blots were washed at room temperature for 15 minutes in 2× SSC, 0.1% SDS, followed by 15 minutes in 1× SSC, 0.1% SDS. This was followed by a third wash for 15 minutes at 50° C. in 0.1× SSC, 0.5% SDS. Washed blots were exposed at −80° C. while still damp to DuPont Reflection™ film with an intensifying screen.

Of the 9 transgenic plant lines that were regenerated from particle bombardments performed with the pBE44 construct, seven of these were identified by Southern blot analysis to contain the trait gene. Northern blots of total RNA isolated from these lines showed variable levels of SBEIIb RNA; in 6 of the analyzed lines, a 500 base transcript was also observed. The size of this hybridizing RNA is consistent with that predicted for the antisense transcript from the chimeric gene of pBE44.

Analysis of Starch from Transformed Corn Plants Containing the 3' Antisense Construct Starch was extracted from single seeds obtained from corn plants transformed with the 3' antisense construct. Seeds were steeped in a solution containing 1.0% lactic acid and 0.3% sodium metabisulfite, pH 3.82, held at 52° C. for 22–24 h. Seeds were drained, rinsed and homogenized individually in 8–9 mL of a solution of 100 mM NaCl. Five mL of toluene were added to each tube and vigorously shaken twice for 6 minutes using a paint mixer, and allowed to settle for 30 minutes. Two mL of 100 mM NaCl was sprayed onto the solution, allowed to settle for 30 minutes, and the protein-toluene layer was aspirated off. The toluene wash step was repeated. Twelve mL water was added and shaken in a paint shaker for 45 seconds. This solution was centrifuged for 10 minutes and the water was removed. The water wash was repeated, followed by a final wash with 12 mL of acetone. After shaking and centrifugation steps, the acetone was drained and allowed to evaporate for 1 h. Starch extracts were incubated in a 40° C. oven overnight.

Extracted starches were enzymatically debranched as follows. Extracted starches (10 mg) from individual seeds were gelatinized in 2 mL water by heating to 115° C. for 0.5 h. Four units of isoamylase (Sigma) in 50 mM NaOAc buffer, pH 4.5, were added to each of the gelatinized starches and placed in a water bath at 45° C. for 2.5 h. Enzyme was inactivated by heating samples to 115° C. for 5 minutes. Each sample was filtered through a 0.45 micron filter, and placed into individual autosampler vials. Samples were held at 45° C. until injection.

Fifty mL of debranched starch sample were injected and run through four columns (3 ×250 Å and 1×500 Å ultrahydrogel™; Waters) arranged in series at 45° C. and eluted with 50 mM NaOAc at a flow rate of 0.7 mL/min. Sampling interval was 65 minutes. A refractive index detector (Waters), integrator/plotter (Spectra-Physics) and computer were used for sample detection, recording of retention times and chromatogram storage, respectively. Retention times of collected samples were compared to retention times of pullulan standards (380K, 100K, 23.7K, 5.8K, 728 and 180 mw).

Spectra-Physics software was used to make any baseline corrections to the chromatogram including subtraction of a blank chromatogram. Spectra-Physics GPC-PC software was used to enter molecular weights and retention times of pullulan standards. The data were imported to Microsoft Excel for parsing and stripping of all data except molecular weight and area percent of the chromatogram. The remaining data were used to determine branch chain distribution of the amylopectin using Jandel Scientific Peakfit software. A series of six Gaussian curves were fit to the amylopectin portion of the chromatograms as described by Ong et al. ((1994) *Carbohydrate Res.* 260:99–117).

Amylopectin is typically described by its distribution of branch chains in the molecule. The amylopectin molecule is comprised of alternating crystalline and amorphous regions. The crystalline region is where many of the branch points ($\alpha$–1,6 linkages) occur, while the amorphous region is an area of little to no branching and few branch chains. The type of chain is designated A or B. A chains are unbranched and span a single crystalline region. B 1 chains also span a single crystalline region but are branched. B2, B3 and B4+ chains are branched and span 2, 3 and 4 or more crystalline regions, respectively (Hizukuri (1986) *Carbohydrate Res.* 147:342–347). The relative area under the six Gaussian curves fit to the amylopectin portion of the chromatograms using Peakfit software was used to determine the area percentage of the A, B1, B2, B3 and B4+ chains. The areas of the first and second peaks were summed to give the relative amount of A and B1 chains, the third and fourth peaks represent the B2 and B3 chains, respectively, and the sum of the fifth and sixth peaks represent the relative area of the B4+ chains. The mass average DP of the A and B1, B2, B3, and B4 chains were 14, 22, 43 and 69 respectively.

Starches from individual RI kernels of plants transformed with pBE44 (the 3' antisense construct for corn SBEIIb) were analyzed using the procedure described above. As known to those skilled in the art, the antisense phenomenon is generally not observed in every individual transgenic line. Therefore, individual kernels from multiple lines were examined and as expected, some, but not all lines possessed kernels demonstrating an altered starch phenotype. Individual kernels from a negative control plant (Transformation Negative Control Line 03376; this line has been through the transformation process but does not carry the antisense gene) were included in each set of assays, and duplicate assays were performed on starches from individual kernels. Table 1 presents the results for individual kernels (kernal Nos. 1 and 7) from a transformed corn line (0693) which did show a phenotype. The data represent the percentage difference of the various branches between kernels of the transformed line and kernels from a negative control (line 03376, which has been through the transformation process but does not contain the antisense gene).

TABLE 1

Percentage Difference of Branch Chain Distribution of Amylopectin from Starch Isolated from Individual Seed from 3' Antisense SBEIIb Transgenic Corn Line (0693) Compared to Starch Isolated from Negative Control Line (03376).

| Starch Source | A + B1 | B2 | B3 | B4+ |
| --- | --- | --- | --- | --- |
| 06931 | 80 | 95 | 104 | 226 |
| 06937 | 91 | 90 | 100 | 194 |

Both the experimental (06931 and 06937) and control (03376) data are the average of duplicate assays of starches isolated from individual kernals. As can be seen, there is an approximately 2-fold increase (226% of control and 194% of control for 06931 and 06937, respectively) in long (B4+) chains, indicating that long chains (B4+) are favored at the expense of shorter chains (A's, B1's and B2's) in starches possessing the antisense gene relative to control starch. The instant transgenic plants thus demonstrate a unique starch branching phenotype compared to non-transgenic control plants. This data indicates that alteration of corn starch branching enzyme activity by suppressing expression of the corresponding genes encoding starch branching enzymes results in an altered starch phenotype.

R1 kernels from the pBE44 line, 0693, were planted and R2 grain was produced. Individual R2 kernels were analyzed using the same procedure as described above for analysis of R1 kernels. Individual kernels from a negative control line (04659, which has been through the transformation process but does not carry the antisense gene) were included in this set of assays. Table 2 presents the results for R2 kernels. The data represent the percentage difference of the various branches between R2 kernels and kernels from the negative control.

TABLE 2

Percentage Difference of Branch Chain Distribution of Amylopectin From Starch Isolated From Individual R2 Seed From 3' Antisense SBEIIb Transgenic Corn Line (05985) Compared to Starch Isolated From Negative Control Line (04659).

| Starch Source | A + B1 | B2 | B3 | B4+ |
|---|---|---|---|---|
| 059852 | 69 | 91 | 132 | 476 |
| 0598510 | 71 | 92 | 129 | 455 |

As can be seen, long chains (B3 and B4+) are favored at the expense of shorter chains (A's, B1's and B2's) in the amylopectin derived from R2 kernels possessing the antisense gene relative to control starch (04659). The instant transgenic plant thus demonstrates a unique starch branching phenotype compared to non-transgenic control plants. This data also indicates that the phenotype observed in the R2 seed is stronger than that of the R1 seed (Table 1) which may be due to segregation.

R4 grain (line XAY00681) was produced, harvested and starch was extracted. For starch branch chain distribution and determination of amylose content, starch digestion was modified from that in previous examples slightly as follows. Seven mg of each starch sample was added to a screw cap test tube with 1.1 mL of water. The tubes were heated to 120° C. for 30 minutes and then placed in a water bath at 45° C. Debranching solution was made by diluting 50 µL of isoamlyase (5×10$^6$ units/mL, Sigma) per mL of sodium acetate buffer (50 mM, pH 4.5). 40 µL of debranching solution was added to each starch sample and incubated for 3 h at 45° C. Reactions were stopped by heating to 110° C. for 5 minutes. Debranched starch samples were lyophilized and redisolved in DMSO for analysis by gel permeation chromatography (GPC). One hundred µL of debranched starch was injected and run through 2 columns (Polymer Labs, Mixed Bed-C)) in series at 1 00° C. and eluted with DMSO at a flow rate of 1.0 mL/min. Sampling interval was 25 minutes. A refractive index detector (Waters) was used with a computer running Chemstation Software (version A.02.05, Hewlett Packard) for detection and data collection and storage, respectively. Retention times of pullulan standards (380K, 100K, 23.7K, 5.8K, 728 and 180 mw) were used to define molecular weight ranges for the debranched starch samples. The proportion of the total starch was determined for 24 ranges of degree of polymerization (DP) spanning both the amylose and amylopectin portions of the chromatogram. For purposes of comparison to data reported above, the percentage area in appropriate DP ranges was summed to give values for A and B 1 chains, B2, B3 and B4+chains of the amylopectin portion of the chromatogram. The portion of the total area above DP 150 was used to determined amylose content.

Starch from line XAY00681 (R4) and dent starch (control) were debranched and analyzed. The results are shown in Tables 3 and 4 below:

TABLE 3

The percentage of total chromatographic area within given degree of polymerization (DP) ranges for starch derived from R4 grain containing the 3' antisense transcript of corn SBEIIb and normal dent starch (control). Averages (n = 12) and standard errors of the mean (SE) are reported.

| | Dent Starch | | XAY00681 | |
|---|---|---|---|---|
| DP range | Average | SE | Average | SE |
| >5k | 5.45 | 0.14 | 5.59 | 0.63 |
| 3–5k | 2.62 | 0.05 | 3.15 | 0.06 |
| 1.8–3k | 3.03 | 0.04 | 3.89 | 0.09 |
| 1.2–1.8k | 2.49 | 0.05 | 3.54 | 0.10 |
| 0.9–1.2k | 1.92 | 0.04 | 2.67 | 0.06 |
| 600–900 | 2.86 | 0.03 | 3.91 | 0.09 |
| 400–600 | 2.78 | 0.05 | 3.83 | 0.08 |
| 250–400 | 2.83 | 0.05 | 3.83 | SE |
| 150–250 | 2.43 | 0.04 | 3.50 | 0.09 |
| 90–150 | 2.38 | 0.04 | 3.50 | 0.09 |
| 60–90 | 4.04 | 0.08 | 6.10 | 0.07 |
| 48–60 | 4.08 | 0.07 | 4.81 | 0.04 |
| 40–48 | 3.95 | 0.09 | 3.96 | 0.05 |
| 32–40 | 4.52 | 0.13 | 4.45 | 0.05 |
| 28–32 | 3.45 | 0.12 | 2.89 | 0.04 |
| 24–28 | 3.69 | 0.17 | 3.37 | 0.06 |
| 21–24 | 4.72 | 0.18 | 3.74 | 0.05 |
| 18–21 | 6.01 | 0.03 | 4.83 | 0.10 |
| 15–18 | 8.42 | 0.05 | 6.18 | 0.12 |
| 13–15 | 7.24 | 0.21 | 5.34 | 0.11 |
| 11–15 | 6.64 | 0.17 | 4.49 | 0.10 |
| 9–11 | 6.20 | 0.08 | 4.54 | 0.11 |
| 7–9 | 4.48 | 0.06 | 3.40 | 0.07 |
| 5–7 | 3.67 | 0.07 | 2.91 | 0.05 |

TABLE 4

Percentage Difference of Branch Chain Distribution of Amylopectin (expressed as A + B1, B2, B3 and B4+) and Amylose Content (% of Total Starch) from Starch Isolated from R4 Grain containing the 3' Antisense Transcript of Corn SBEIIb (XAY00681) as Compared to Control (Dent). DP range is indicated.

| A + B1 (5–15) | B2 (15–32) | B3 (32–60) | B4+ (60–150) | Amylose (>150) |
|---|---|---|---|---|
| 83.3 | 89.0 | 117.4 | 184.5 | 128.4 |

As can be seen in Tables 3 and 4, the relative amount of amylose increased as did the proportion of longer branches on amylopectin in starch which contained the 3' antisense transcript of corn SBE IIb compared to a dent control.

Functional Analysis of Starch from Lines Homozygous for the 3' Antisense Construct Kernels of plants of a line (XAT00025), homozygous for the pBE44 construct, were isolated from the progeny of line 05985 in order to obtain sufficient quantities of starch for functionality testing. Starch was extracted from dry mature kernels from line XAT00025, dent, and ae corn. For each line 15 g of kernels were weighed into a 50 mL Erlenmeyer flask and steeped in 50 mL of steep solution (same as above) for 18 h at 52° C. The kernels were drained and rinsed with water. The kernels were then homogenized using a 20 mm Polytron probe (Kinematica GmbH; Kriens-Luzern, Switzerland) in 50 mL of cold 50 mM NaCl. The homogenate was filtered through a 72 micron mesh screen. The filtrate was brought up to a total volume of 400 mL with 50 mM NaCl and an equal volume of toluene was added. The mixture was stirred with a magnetic stir bar for 1 h at sufficient speed to completely emulsify the two phases. The emulsion was allowed to separate overnight in a covered beaker. The upper toluene layer was aspirated from the beaker and discarded. The starch slurry remaining in the bottom of the beaker was resuspended, poured into a 250 mL centrifuge bottle and centrifuged 15 minutes at 25,000 RCF. The supernatent was discarded and the starch was washed sequentially with water and acetone by shaking and centrifuging as above. After the acetone wash and centrifugation the acetone was decanted and the starch allowed to dry overnight in a fume hood at room temperature.

A Rapid Visco Analyzer (Newport Scientific; Sydney, Australia) with high sensitivity option and Thermocline software was used for pasting curve analysis. For each line, 1.50 g of starch was weighed into the sample cup and 25 mL of phosphate/citrate buffer (pH 6.50) containing 1% NaCl was added. Pasting curve analysis was performed using the following temperature profile: Idle temperature 50° C., hold at 50° C. for 0.5 minutes, linear heating to 95° C. for 2.5 minutes, linear cooling to 50° C. over 4 minutes, hold at 50° C. for four minutes.

Results of the Rapid Visco Analyzer pasting analysis are shown in FIG. 5. It can be seen that the starch produced by line XAT00025 differs in its pasting properties both from normal dent starch and from a line homozygous for the ae mutation. This result demonstrates that the alteration of starch fine structure produced by suppressing expression of a starch branching enzyme can create a starch of novel functionality.

Example 2

Figure 6:
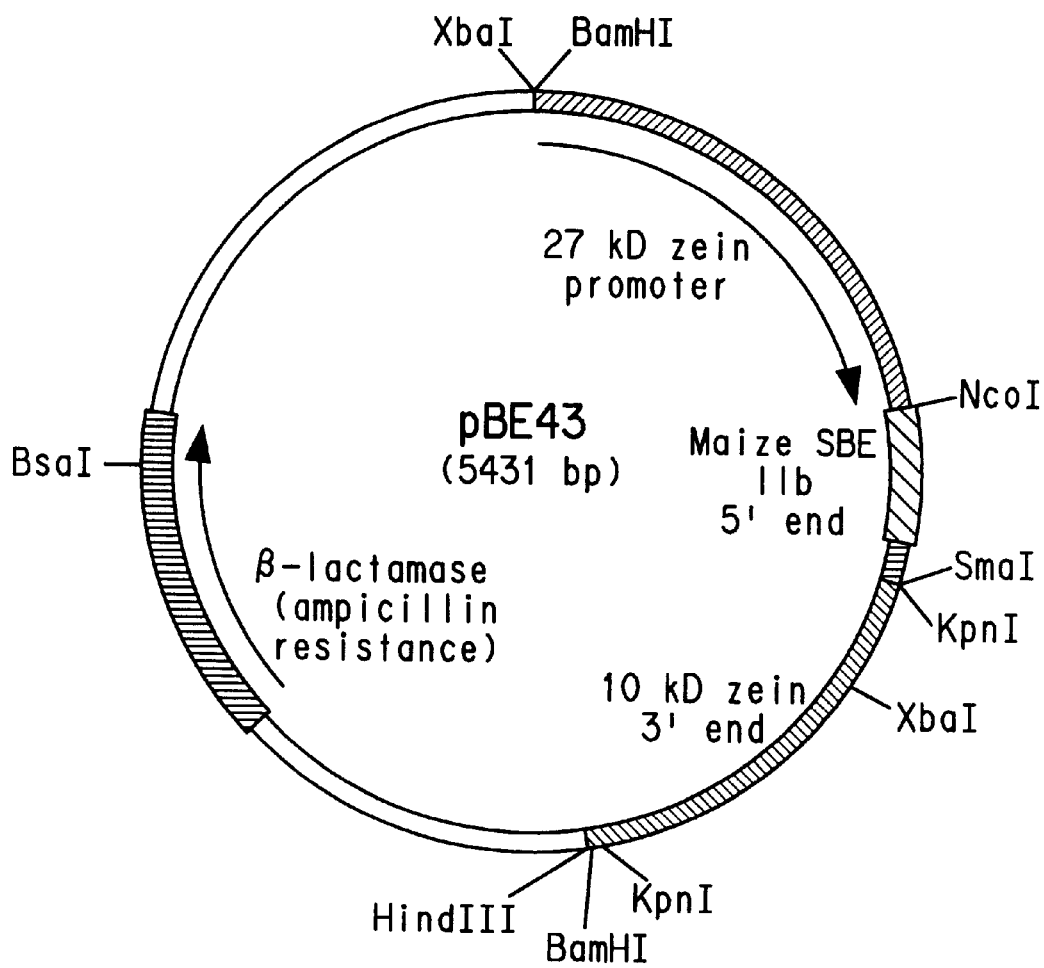

Preparation of Transgenic Corn Expressing a 5' Antisense Transcript of Corn Starch Branching Enzyme IIb Preparation of the Expression Vector Encoding the 5' Antisense Construct The chimeric gene inserted into plasmid construct pBE43 (FIG. 6) comprises a 5= fragment of the SBEIIb cDNA in antisense orientation with respect to the maize 27 kD zein promoter, located 5' to the SBEIIb fragment, and the 10 kD zein 3' end, located 3' to the SBEIIb fragment. The SBEIIb fragment of this construct was generated by polymerase chain reaction (PCR) of pBE240 using appropriate oligonucleotide primers. These primers were synthesized on a Beckman Oligo 1000™ DNA Synthesizer. The 507 bp fragment of pBE43 (SEQ ID NO:5) was synthesized using the oligonucleotide pair BE39 (SEQ ID NO:6) and BE40 (SEQ ID NO:7):

BE39 5'-GAATTCCCGGGACCCGGATTTCGCTCTT-3' (SEQ ID NO:6)

BE40 5'-GAATTCCATGGTCTATAGAGGCTGTACCG-3' (SEQ ID NO:7).

Cloning sites (NcoI or SmaI) were incorporated into the oligonucleotides to provide antisense orientation of the DNA fragments when inserted into the digested vector pML103 as described below. Amplification was performed in a 100 ml volume in a standard PCR mix consisting of 0.4 mM of each oligonucleotide and 0.3 pM of pBE240 in 10 mM Tris-HCl, pH 8.3, 50 mM KCl, 1.5 mM MgCl$_2$, 0.001% w/v gelatin, 200 mM dGTP, 200 mM DATP, 200 mM dTTP, 200 mM dCTP and 0.025 unit Amplitaq™ DNA polymerase. Reactions were carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. The amplified DNA was digested with restriction enzymes NcoI and SmaI and fractionated on a 0.7% low melting point agarose gel in 40 mM Tris-acetate, pH 8.5, 1 mM EDTA. The appropriate band was excised from the gel, melted at 68° C. and combined with a 4.9 kb NcoI-SmaI fragment of the plasmid pML103 (FIG. 3). The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA was ligated at 15° C. overnight, essentially as described (Maniatis). The ligated DNA was used to transform E. coli XL 1-Blue (Epicurian Coli XL-1 Blue'; Stratagene™). Bacterial transformants were screened by restriction enzyme digestion of plasmid DNA and limited nucleotide sequence analysis using the dideoxy chain termination method (Sequenase™ DNA Sequencing Kit; U. S. Biochemical). The resulting plasmid construct, pBE43, comprises a chimeric gene encoding in the 5' to 3' direction, the maize 27 kD zein promoter, a 5' fragment of the corn SBEIIb gene in antisense orientation, and the 10 kD zein 3' region.

Larger quantities of pBE43 plasmid DNA were prepared by the alkaline lysis method, followed by purification by CsCl density gradient centrifugation.

Transformation of Corn with the 5' Antisense Construct

The 5' antisense construct (pBE43) was introduced into embryogenic corn tissue by the particle bombardment method essentially as described in Example 1. Seven days after bombardment the tissue was transferred to N6 medium that contained glufosinate (2 mg per liter) and lacked casein or proline. The tissue continued to grow slowly on this medium. After an additional 2 weeks the tissue was transferred to fresh N6 medium containing glufosinate. After 6 weeks, areas of about 1 cm in diameter of actively growing callus were identified on some of the plates containing the glufosinate-supplemented medium. These calli continued to grow when sub-cultured on the selective medium.

Plants were regenerated from the transgenic callus by first transferring clusters of tissue to N6 medium supplemented with 0.2 mg per liter of 2,4-D. After two weeks the tissue was transferred to regeneration medium (Fronun et al. (1990) Bio/Technology 8:833–839). Ninety-nine transgenic plant lines were generated from 2 separate particle bombardment experiments performed with the DNA construct pBE43.

Molecular Analysis of Transformed Corn Plants Containing the 5' Antisense Construct Southern blot and Northern blot analyses of DNA and RNA from corn plants transformed with the 5' antisense construct (pBE43) were performed as described in Example 1. For Southerns, the DNA probe was prepared as described in Example 1. Of the ninety-nine transgenic plant lines that were generated from particle bombardment experiments, twenty-eight were subjected to Southern blot analysis using a 666 bp EcoRI-BamHI fragment of the SBEIIb cDNA as a hybridization probe. Twenty lines carrying the trait gene were identified. The pattern of hybridizing bands ranged from fairly simple to rather complex, consistent with duplication and rearrangement of the construct DNA upon to integration into the corn genome.

Total RNA was isolated from 35 pBE43-transformed plant lines. The RNA was denatured, fractionated by gel electrophoresis, blotted onto nylon membranes and hybridized to a probe encompassing the complete SBEIIb cDNA or a 5' portion of it. The level of SBEIIb RNA was found to vary considerably from line to line but in no case was a complete absence of RNA found. This result is not unexpected given that the RNA was prepared from a segregating population of seed. In addition to the 2.7 kb SBEIIb RNA, a smaller RNA species was observed in some of the analyzed plant lines. The intensity of this band was found to vary with 8 lines showing moderate to weak signals and 4 lines showing strong signals. The size of this RNA band, approximately 600 bases, matches that expected from the antisense transcript derived from the chimeric gene.

This identity was confirmed by hybridizing Northern blots to strand specific riboprobes. For generation of single stranded RNA probes, the SBEIIb DNA fragment of construct pBE43 was subcloned into a modified pBLUE-SCRIPT SK+vector which contains an NcoI site in place of the XbaI site in the polylinker. For synthesis of the sense (RNA identical) strand, the plasmid was first linearized by digestion with NcoI and transcription carried out by T7 RNA polymerase in the presence of ($\alpha$-$^{32}$P),UTP using an RNA Transcription Kit (Stratagene). For synthesis of the antisense RNA probe, the plasmid was linearized by digestion with EcoRI, followed by transcription catalyzed by T3 RNA polymerase. Pre-hybridization of Northern blots was accomplished at 60° C. in 50% formamide, 6x SSPE, 1 × Denhardt's solution and I 00 mg/ml yeast t-RNA. Hybridization was carried out in the same buffer supplemented with 5% dextran sulfate and containing $1 \times 10^6$ cpm/ml of RNA probe for approximately 18 hrs at 60° C. Blots were washed for 15 minutes at room temperature in 2× SSPE, 30 minutes at 70° C. in 1× SSPE, 0.1% SDS followed by 30 minutes at 70° C. in 0. 1× SSPE, 0.5% SDS. Washed blots were exposed at −80° C. while still damp to Dupont Reflection' film with an intensifying screen. The probe corresponding to the antisense RNA strand detected only the endogenous SBEIIb RNA while the sense probe detected only the 600 base RNA species. This result is consistent with the identity of the 600 base RNA of the antisense transcript of pBE43.

Analysis of Starch from Transformed Corn Plants Containing the 5' Antisense Construct Starches from individual R1 kernels of plants transformed with pBE43 (the 5' antisense construct for corn SBEIIb) were extracted and analyzed using the procedure described in Example 1. As known to those skilled in the art, the antisense or cosuppression phenomenon is generally not observed in every individual transgenic line. Therefore, individual kernels from multiple lines were examined. No alterations in starch branch chain distribution were observed for the transgenic lines that were screened. It is believed that the number of lines tested was too small to insure finding a plant where an effective antisense event occurred. As described above, the number of plants that must be screened can be unpredictable and large. It is assumed that if a sufficiently large number of individuals were examined such an event would be detected. It may be that this particular configuration is less efficient for suppressing expression of this gene; it is for this reason that multiple constructs were prepared and tested.

Example 3

Preparation of Transgenic Corn Expressing a Near Full Length Antisense Transcript of Corn Starch Branching Enzyme IIb Preparation of the Expression Vector Encoding the Near Full Length Antisense Construct The construct pBE45 is similar to pBE43 and pBE44 except that the SBEIIb fragment is 2.16 kb and contains the entire 5' untranslated region as well as 2.08 kb of the coding region (SEQ ID NO:8). pBE240 was first digested with EcoRI and then subjected to an end filling reaction with the Klenow fragment of DNA polymerase I (Maniatis). The blunt-ended DNA was fractionated on a low melting point agarose gel and the excised band combined with a 4.9 kb NcoI-SmaI fragment of the plasmid pML103 (FIG. 3). The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA were ligated at 15° C. overnight, essentially as described (Maniatis). The ligated DNA was used to transform E. coli XL1-Blue (Epicurian Coli XL-1 Blue™; Stratagene). Bacterial transformants were screened for the presence of and the orientation of the added DNA by restriction enzyme digestion with KpnI and limited nucleotide sequence analysis using the dideoxy chain termination method (Sequenase™ DNA Sequencing Kit; U.S. Biochemical). According to this analysis, in pBE45, the SBEIIb fragment is present in inverse orientation relative to the 27 kD zein promoter. The resulting plasmid construct, pBE45, comprises a chimeric gene encoding, in the 5' to 3' direction, the maize 27 kD zein promoter, the near full length fragment of corn SBEIIb in antisense orientation, and the 10 kD zein 3' region (FIG. 7).

Larger quantities of pBE45 plasmid DNA were prepared by the alkaline lysis method, followed by purification by CsCl density gradient centrifugation.

Transformation of Corn with the Near Full Length Antisense Construct

The near fall length antisense construct (pBE45) was introduced into embryogenic corn tissue by the particle bombardment method essentially as described in Example 1. Seven days after bombardment, the tissue was transferred to N6 medium that contained glufosinate (2 mg per liter) and lacked casein or proline. The tissue continued to grow slowly on this medium. After an additional 2 weeks the tissue was transferred to fresh N6 medium containing glufosinate. After 6 weeks, areas of about 1 cm in diameter of actively growing callus were identified on some of the plates containing the glufosinate-supplemented medium. These calli continued to grow when sub-cultured on the selective medium.

Plants were regenerated from the transgenic callus by first transferring clusters of tissue to N6 medium supplemented with 0.2 mg per liter of 2,4-D. After two weeks the tissue was transferred to regeneration medium (Fromm et al. (1990) Bio/Technology 8:833–839). Ten transgenic plant lines were generated from a single particle bombardment experiment performed with the DNA construct pBE45.

Molecular Analysis of Transformed Corn Plants Containing the Near Full Length Antisense Construct Southern blot and Northern blot analyses of DNA and RNA from corn plants transformed with the near full length antisense construct (pBE45) were performed essentially as described in Example 1. For Southerns, the DNA probe, an EcoRI-BamHI 5' fragment of pBE240, was prepared essentially as described in Example 1. Of the 10 transgenic plant lines that were generated, 5 tested positive for the presence of the introduced trait gene.

Northern blots of total RNA revealed only a single band when probed with the EcoRI-BamFH 5' fragment of the SBEIIb cDNA. Since the SBEIIb RNA and the pBE45 antisense transcript are similar in size, 2.7 and 2.4 kb respectively, it seemed possible that the two species might not be adequately resolved during agarose gel electrophoresis. For this reason, Northern blots were also hybridized to strand specific RNA probes, essentially as described in Example 1. However, while the antisense strand detected the endogenous SBEIIb mRNA, no signal was evident when the sense strand probe was employed.

Analysis of Starch from Transformed Corn Plants Containing the Near Full Length Antisense Construct Starches from individual R1 kernels of plants transformed with pBE45 (the near fall length antisense construct for corn SBEIIb) were analyzed using the procedure described in Example 1. As known to those skilled in the art, the antisense phenomenon is generally not observed in every individual transgenic line. Therefore, individual kernels from multiple lines were examined and as expected, some, but not all lines possessed kernels demonstrating an altered starch phenotype. Table 5 presents the results for kernels from a transformed corn line which did show a phenotype. The data represent the percentage difference of the various branches between kernels of the transformed line and kernels from a negative control (line 03376, which has been through the transformation process but does not contain the antisense gene).

TABLE 5

Percentage Difference of Branch Chain Distribution of Amylopectin from Starch Isolated from Individual Seed from near Full Length Antisense SBEIIb Transgenic Corn Line (9228) Compared to Starch Isolated from Negative Control Line (03376).

| Starch Source | A + B1 | B2 | B3 | B4+ |
| --- | --- | --- | --- | --- |
| 92283 | 92 | 97 | 81 | 192 |

As can be seen, long chains (B4+) are favored at the expense of shorter chains (A's and B1's, B2's and B3's) in the starch derived from the corn plant possessing the antisense gene relative to control starch (03376). The instant transgenic plant thus demonstrates a unique starch branching phenotype compared to non-transgenic control plants. This data indicates that alteration of corn starch branching enzyme activity by suppressing expression of the corresponding genes encoding starch branching enzymes results in an altered starch phenotype.

Example 4

Preparation of Transzenic Corn Expressing a Near Full Length Sense Transcript of Corn Starch Branching Enzyme IIb Preparation of the Expression Vector Encoding the Near Full Length Sense Construct Plasmid pBE96 comprises a 2.09 kb fragment of the SBEIIb cDNA (SEQ ID NO:9) joined in the sense orientation to the 27 kD zein promoter and the 10 kD zein 3' end (FIG. 8). The SBEIIb fragment commences at the initiating ATG codon of the coding region and terminates 312 bp 5' of the translation termination codon. pBE240 was subjected to site specific mutagenesis (Sculptor™ Mutagenesis Kit, Amersham) to generate an NcoI site at the ATG start site. The mutagenized plasmid was first digested with EcoRI and then rendered blunt-ended by reaction with Klenow. The DNA fragment was liberated by digestion with NcoI, fractionated by electrophoresis on a low melting point agarose gel, and ligated to the NcoI-SmaI fragment of pML103 as described above. Transformants in E. coli XL1-Blue were tested for the presence of the SBEIIb fragment by restriction enzyme digestion with NcoI and HindIII followed by nucleotide sequence determination. From this analysis, pBE71 was identified. pBE71 was digested with PvuII to release the full chimeric gene (27 kD zein promoter-truncated SBEIIb-10 kD zein 3' end) and this fragment was cloned into the vector pKS17. pKS17 contains the hygromycin B phosphotransferase gene which confers resistance to the antibiotic hygromycin. pKS17 was assembled by the addition of a T7promoter -HPT-T7 terminator chimeric gene to a multicopy vector from which the b-lactamase gene had been deleted. The resultant plasmid containing the 27 kD zein-truncated SBEIIb-10 kD zein insert in pKS17 is termed pBE96.

Example 5

Preparation of Transgenic Corn Expressing Antisense Transcripts of Corn Starch Branching Enzyme I A corn SBEI DNA fragment was generated from the published sequence of the SBEI cDNA (Baba et al. (1991) Biochem. Biophys. Res. Commun. 181:87–94) by the polymerase chain reaction (PCR) using primers BE14 (SEQ ID NO:10) and BEI5 (SEQ ID NO:11):

BE14
5'-AAGCTTGAATTCTGCTCGGTGATGAGACAC-3' (SEQ ID NO:10)

BE15
5'-AAGCTTGAATTCCTTGGAGGTGATGGCTAC-3' (SEQ ID NO:11)

BE14 and BE15 were combined with lambda DNA prepared from plate lysates of a 12 DAP corn cDNA library in lambda ZapII (Stratagene) in a standard PCR reaction mix consisting of 0.4 mM of each oligonucleotide and 0.8 mg of template DNA in 10 mM Tris-HCl, pH 8.3, 50 mM KCl, 1.5 mM $MgCl_2$, 0.001% w/v gelatin, 200 mM dGTP, 200 mM dATP, 200 mM dTTP, 200 mM dCTP and 0.025 unit Amplitaq™ DNA polymerase in a 100 $\mu$l volume. The 875 bp PCR fragment was digested with the restriction enzyme AccI to release a 325 bp fragment (encompassing nucleotides 2290–2610 of the published sequence) that was then used as a hybridization probe to screen the 12 DAP corn cDNA library for full length SBEI clones. One of the isolated clones, designated pBE65, contained a 2772 bp EcoRI insert (SEQ ID NO:12). Nucleotides 165 to 2772 of this clone were found to be more than 99% identical to the sequence of the maize SBEI cDNA clone published by Baba et al. ((1991) Biochem. Biophys. Res. Commun. 181:87–94). However, the 5' terminal 164 bp of the insert did not agree with the published sequence. To resolve this discrepancy, we attempted to amplify this region of the gene by PCR using corn total DNA as the template. A 571 bp 5' fragment was isolated, sequenced and found to be identical to the cDNA over nucleotides 49 to 188. pBE65 was then used as a starting point in the generation of sense and antisense SBEI constructs including pBE68 and pBE97 described below. In the time since these constructs were made and introduced into corn, a second SBEI sequence became available (Fisher et al. (1995) Plant Physiol. 108:1313–1314). The 5' terminal 165 bp of pBE65 showed poor agreement with this sequence as it did with the previous SBEI sequence. As a result of subsequent experiments, it is now concluded that pBE65 contains a 165 bp 5' terminal segment that is not related to SBEI but which presumably arose as an artifact during the cloning of corn cDNA. This region is followed by 2607 bp of SBEI cDNA which encodes 42 amino acids of the SBEI transit peptide, the 760 amino acids of the mature SBEI protein and contains 194 bp of 3' untranslated DNA. The plasmid pBE65 has been deposited under the terms of the Budapest Treaty at the ATCC (American Type Tissue Culture Collection, 10801 University Boulevard, Manassas, Va. 20110–2209) and bears the following accession number: 97817.

Preparation of Expression Vectors Encoding SBEI Antisense Constructs

Since it was not known which portions of the cDNA sequence would be most effective in mediating suppression of SBEI expression, three constructs bearing different SBEI fragments in antisense orientation were made. The chimeric gene of plasmid pBE68 (FIG. 9) comprises a 3' fragment of the SBEI cDNA in antisense orientation with respect to the maize 27 kD zein promoter that is located 5' to the SBEI fragment, and the 10 kD zein 3' end that is located 3' to the SBEI fragment. The 373 bp SBEI fragment of this construct (SEQ ID NO:13) was obtained by PCR of pBE65 using the oligonucleotide primer pair BE43 (SEQ ID NO:14) and BE52 (SEQ ID NO:15):

BE43 5'-GAATTCCCGGGCCGAACTCGTTCAAAG-3' (SEQ ID NO:14)

BE52 5'-GAATTCCATGGCGGTGATGAGACACCAGTC-3' (SEQ ID NO:15)

The chimeric gene of pBE69 (FIG. 10) is analogous to that of pBE68 except that the SBEI fragment consists of a 5' portion of the SBEI cDNA. The 571 bp fragment of this construct (SEQ ID NO:16) was obtained by amplification of pBE65 using the primer pair BE46 (SEQ ID NO:17) and BE50 (SEQ ID NO:18):

BE46 5'-GAATTCCATGGCCATCTTATGGTTTGCACC-3' (SEQ ID NO:17)

BE50 5'-GAATTCCCGGGCATAGCATAGATATGACGGC-3' (SEQ ID NO:18)

Cloning sites (NcoI and SmaI) were incorporated into the above oligonucleotides to provide antisense orientation of the DNA fragments when inserted into the vector pML103 described in Example 1. Amplification was performed in a 100 ml volume in a standard PCR reaction mix as defined in Example 1. Reactions were carried out in a Perkin-Elmer Cetus Thermocycler™ for 30 cycles comprising 1 minute at 95° C., 2 minutes at 55° C. and 3 minutes at 72° C., with a final 7 minute extension at 72° C. after the last cycle. Amplified DNAs were digested with the restriction enzymes NcoI and SmaI and fractionated on a 0.7% low melting point agarose gel in 40 mM Tris-acetate, pH8.5, 1 mM EDTA. The bands corresponding to the 3' and 5' fragments of the SBEI cDNA were excised from the gel, melted at 68° C. and each was combined with the 4.9 kb NcoI-SmaI fragment of plasmid pML103 (FIG. 3) described in Example 1. Vector and insert DNAs were ligated at 15° C. overnight, essentially as described in Maniatis. The chimeric gene of construct pBE72 (FIG. 11) consists of a 2.49 kb SBEI fragment in antisense orientation with respect to the maize 27 kD zein promoter that is located 5' to the SBEI fragment and the 10 kD zein 3' end that is located 3' to the SBEI fragment. The SBEI fragment of pBE72 (SEQ ID NO:19) was obtained by restriction enzyme digestion of pBE65 with EcoRI and HindIII followed by reaction with the Klenow fragment of *E. coli* DNA polymerase. The blunt-ended fragment was ligated to the Klenow-treated 4.9 kb NcoI-SmaI fragment of pML103 essentially as described in Maniatis.

The ligated DNAs were used to transform *E. coli* XL1-Blue (Epicurean Coli XL-1 Blue™; Stratagene). Bacterial transformants were initially screened by restriction enzyme digestion of plasmid DNA. For pBE68 and pBE69 transformants, the presence of the insert was detected by combined digestion with NcoI and SmaI. For pBE72 transformants, digestion of the DNA with SalI was used to confirm the presence of insert DNA and to determine the orientation of the SBEI fragment relative to the 27 kD zein promoter. Identified transformants were further characterized by limited nucleotide sequence analysis using the dideoxy chain termination method (Sequenase™ DNA Sequencing Kit; U.S. Biochemical).

The chimeric gene of pBE72 was subsequently introduced into the vector pKS17, described in Example 4. The 27 kD zein-SBEI-10 kD zein DNA fragment of pBE72 was liberated by partial digestion with BamHI and cloned into the BamHI site of pKS 17 to give a hygromycin resistant equivalent of pBE72 termed pBE108 (FIG. 12).

Transformation of Corn with the SBEI Antisense Constructs

In separate experiments, each SBEI antisense construct was introduced into embryogenic corn tissue by the particle bombardment method essentially as described in Example 1. Seven days after bombardment, the tissue was transferred to N6 medium that contained glufosinate (2 mg per liter) and lacked casein or proline. The tissue continued to grow slowly on this medium. After an additional 2 weeks, the tissue was transferred to fresh N6 medium containing glufosinate. After 6 weeks, areas of about 1 cm in diameter of actively growing callus were identified on some of the plates containing the glufosinate supplemented medium. These calli continued to grow when sub-cultured on the selective medium.

Plants were regenerated from the transgenic callus by first transferring clusters of tissue to N6 medium supplemented with 0.2 mg per liter of 2,4-D. After two weeks, the tissue was transferred to regeneration medium (Fromm et al. (1990) *Bio/Technology* 8:833–839). Nine transgenic plant lines were regenerated from particle bombardment experiments performed with the DNA construct pBE68, 20 transgenic lines were regenerated from particle bombardments performed with the DNA construct pBE69 and 9 transgenic lines were regenerated from particle bombardment experiments performed with the DNA construct pBE72.

Molecular Analysis of Transgenic Corn Plants Containing the SBEI Antisense Constructs Total DNA was isolated from leaf tissue of transgenic plants essentially as described in Example 1. For Southern blot analysis of pBE68, pBE69 and pBE72 transformants, 10 mg of isolated DNA was digested with the restriction enzyme XbaI at 37° C. for 6 hrs in the buffer supplied by the manufacturer. The restricted DNAs were electrophoresed at 40 volts overnight on a 0.8% agarose gel in Tris-phosphate-EDTA buffer (Maniatis) and transferred to Immobilon™ membranes. The blots were pre-hybridized, hybridized with nick translated pBE65 insert, and washed as described in Example 1.

Total RNA was isolated from developing (20–22 DAP) kernels of transgenic plants and Northern blots were prepared as described in Example 1. Blots were probed with nick translated pBE65 insert DNA and subsequently washed according to the regimen outlined in Example 1.

Of the 9 transgenic plant lines that were regenerated from particle bombardments with the pBE68 construct, 5 were identified by Southern blot analysis to contain the trait gene. Northern blot analysis showed variable levels of the 2.7 kb SBEI mRNA in 4 of the Southern positive lines. In addition, 2 of these lines contained a 400 base transcript that presumably corresponds to the antisense RNA specified by the chimeric gene of pBE68. Of the 20 transgenic plant lines that were generated from bombardments with pBE69, 8 were found to contain pBE69 DNA. RNA isolated from two of the pBE69 transgenic plant lines showed the presence of the 600 base antisense transcript. Of the 9 available pBE72 transgenic plant lines, 6 were found by Southern blot analysis to be positive for the presence of the trait gene.

Analysis of Starch from Transformed Corn Plants Containing the 3' and 5' SBE1 Antisense Constructs Starches from individual kernels of plants transformed with pBE68 (the 3' antisense construct for corn SBE1) and pBE69 (the 5' antisense construct for corn SBE1) were extracted using the procedure described in Example 1. As known to those skilled in the art, the antisense phenomenon is generally not observed in every individual transgenic line. Therefore, individual kernels from multiple lines were examined and as expected, some, but not all lines possessed kernels demonstrating an altered phenotype. Starch digestion was modified from that in previous examples slightly as follows. 7.0 mg of each starch sample was added to a screw cap test tube with 1.1 mL of water. The tubes were heated to 120° C. for 30 minutes and then placed in a water bath at 45° C. Debranching solution was made by diluting 50 µL of isoamlyase (5×10⁶ units/mL, Sigma) per mL of sodium acetate buffer (50 mM, pH 4.5). Forty µL of debranching solution was added to each starch sample and incubated for 3 hours at 45° C. Reactions were stopped by heating to 110° C. for 5 minutes. Debranched starch samples were lyophilized and redissolved in DMSO for analysis by gel permeation chromatography (GPC). One hundred µL of debranched starch was injected and run through 2 columns (Polymer Labs, Mixed Bed-C)) in series at 100° C. and eluted with DMSO at a flow rate of 1.0 mL/min. Sampling interval was 25 minutes. A refractive index detector (Waters) was used with a computer running Chemstation Software (version A.02.05, Hewlett Packard) for detection and data collection and storage, respectively. Retention times of pullulan standards (380K, 100K, 23.7K, 5.8K, 728 and 180 mw) were used to define molecular weight ranges for the debranched starch samples. The proportion of the total starch was determined for 24 ranges of degree of polymerization (DP) spanning both the amylose and amylopectin portions of the chromatogram. For purposes of comparison to data reported above the percentage area in appropriate DP ranges was summed to give values for A and B1 chains, B2, B3 and B4+ chains of the amylopectin portion of the chromatogram. The proportion of the total area above DP 150 was used to determine amylose content.

Starch was prepared from twelve individual R4 kernels from a line (XAY01414) positive for the pBE69 construct, debranched and analyzed as described above and compared to twelve individual kernels from untransformed corn. Tables 6 and 7 show the average and standard error for line XAY01414 and the untransformed control.

TABLE 6

The percentage of Total Chromatographic Area within Given Degree of Polymerization (DP) Ranges for Starch Derived from R4 Kernels Containing the 5' Antisense Transcript of Corn SBEI (XAY01414) and Dent Starch (control). Averages of 12 individual seed and standard errors of the mean (SE) are reported.

|  | Dent Starch | | XAY00681 | |
| --- | --- | --- | --- | --- |
| DP range | Average | SE | Average | SE |
| >5k | 5.45 | 0.14 | 5.92 | 0.14 |
| 3–5k | 2.62 | 0.05 | 2.58 | 0.04 |
| 1.8–3k | 3.03 | 0.04 | 2.95 | 0.08 |
| 1.2–1.8k | 2.49 | 0.05 | 2.66 | 0.03 |
| 0.9–1.2k | 1.92 | 0.04 | 2.01 | 0.04 |
| 600–900 | 2.86 | 0.03 | 2.94 | 0.06 |
| 400–600 | 2.78 | 0.05 | 3.07 | 0.04 |
| 250–400 | 2.83 | 0.05 | 3.23 | 0.04 |
| 150–250 | 2.43 | 0.04 | 2.97 | 0.05 |
| 90–150 | 2.38 | 0.04 | 3.61 | 0.06 |
| 60–90 | 4.04 | 0.08 | 5.72 | 0.15 |
| 48–60 | 4.08 | 0.07 | 4.94 | 0.10 |
| 40–48 | 3.95 | 0.09 | 4.86 | 0.04 |
| 32–40 | 4.52 | 0.13 | 5.59 | 0.14 |
| 28–32 | 3.45 | 0.12 | 3.58 | 0.17 |
| 24–28 | 3.69 | 0.17 | 4.40 | 0.08 |
| 21–24 | 4.72 | 0.18 | 4.06 | 0.18 |
| 18–21 | 6.01 | 0.03 | 5.64 | 0.23 |
| 15–18 | 8.42 | 0.05 | 6.17 | 0.16 |
| 13–15 | 7.24 | 0.21 | 5.92 | 0.28 |
| 11–15 | 6.64 | 0.17 | 5.33 | 0.15 |
| 9–11 | 6.20 | 0.08 | 4.71 | 0.13 |
| 7–9 | 4.48 | 0.06 | 3.58 | 0.09 |
| 5–7 | 3.67 | 0.07 | 3.44 | 0.06 |

TABLE 7

Percentage Difference of Branch Chain Distribution of Amylopectin (expressed as A + B1, B2, B3 and B4+) and Amylose Content (% of Total Starch) from Starch Isolated from R4 Kernels Containing the 5' Antisense Transcript of Corn SBEI (XAY01414) as Compared to Control (Dent). DP range is indicated.

| A + B1 (5–15) | B2 (15–32) | B3 (32–60) | B4+ (60–150) | Amylose (>150) |
| --- | --- | --- | --- | --- |
| 83.5 | 93.1 | 126.0 | 149.4 | 107.3 |

The transformant has alterations in both the amylose and amylopectin fractions of the starch. The overall amylose content is increased somewhat in the XAY01414 line. The amylopectin structure is also altered in that the longer chains (B3 and B4+) are increased relative to the dent control and the shorter chains are less abundant than in the dent starch.

Starch was prepared from twelve individual R4 kernels from a line (XAY00013) positive for the pBE68 construct and analyzed as described above. Tables 8 and 9 show the results of this analysis.

TABLE 8

The percentage of Total Chromatographic Area within Given Degree of Polymerization (DP) Ranges for Starch Derived from R4 Kernels Containing the 3' Antisense Transcript of Corn SBEI (XAY00013) and Dent Starch (control). Averages of 12 individual seed and standard errors of the mean (SE) are reported.

| DP range | Dent Starch | | XAY00681 | |
| --- | --- | --- | --- | --- |
| | Average | SE | Average | SE |
| >5k | 5.45 | 0.14 | 6.13 | 0.39 |
| 3–5k | 2.62 | 0.05 | 2.46 | 0.06 |
| 1.8–3k | 3.03 | 0.04 | 2.92 | 0.05 |
| 1.2–1.8k | 2.49 | 0.05 | 2.51 | 0.06 |
| 0.9–1.2k | 1.92 | 0.04 | 2.02 | 0.04 |
| 600–900 | 2.86 | 0.03 | 2.93 | 0.05 |
| 400–600 | 2.78 | 0.05 | 3.02 | 0.06 |
| 250–400 | 2.83 | 0.05 | 3.19 | 0.05 |
| 150–250 | 2.43 | 0.04 | 2.83 | 0.06 |
| 90–150 | 2.38 | 0.04 | 3.15 | 0.07 |
| 60–90 | 4.04 | 0.08 | 5.33 | 0.10 |
| 48–60 | 4.08 | 0.07 | 4.77 | 0.13 |
| 40–48 | 3.95 | 0.09 | 4.73 | 0.16 |
| 32–40 | 4.52 | 0.13 | 5.62 | 0.18 |
| 28–32 | 3.45 | 0.12 | 3.99 | 0.16 |
| 24–28 | 3.69 | 0.17 | 3.97 | 0.19 |
| 21–24 | 4.72 | 0.18 | 4.67 | 0.18 |
| 18–21 | 6.01 | 0.03 | 5.40 | 0.12 |
| 15–18 | 8.42 | 0.05 | 6.64 | 0.16 |
| 13–15 | 7.24 | 0.21 | 5.73 | 0.22 |
| 11–15 | 6.64 | 0.17 | 5.23 | 0.11 |
| 9–11 | 6.20 | 0.08 | 5.27 | 0.10 |
| 7–9 | 4.48 | 0.06 | 4.08 | 0.09 |
| 5–7 | 3.67 | 0.07 | 3.31 | 0.10 |

TABLE 9

Percentage Difference of Branch Chain Distribution of Amylopectin (expressed as A + B1, B2, B3 and B4+) and Amylose Content (% of Total Starch) from Starch Isolated from R4 Kernels Containing the 3' Antisense Transcript of Corn SBEI (XAY00013) as Compared to Control (Dent). DP range is indicated.

| A + B1 (5–15) | B2 (15–32) | B3 (32–60) | B4+ (60–150) | Amylose (>150) |
| --- | --- | --- | --- | --- |
| 85.6 | 95.9 | 123.1 | 135.1 | 10.60 |

Like the XAY01414 line, the line transformed with the pBE68 construct has alterations in both the amylose and amylopectin fractions of the starch. Amylose content is increased relative to the control and longer chains (B4+and B3) are increased in the amylopectin. The majority of the increase in amylose content is due to an increase in the Amylose of DP greater than 5000.

The instant transgenic plants thus demonstrate a unique starch branching pattern compared to the control plants. This data indicates that alteration of corn starch branching enzyme activity by suppressing expression of the corresponding genes encoding starch branching enzymes results in an altered starch phenotype.

Example 6

Preparation of Transgenic Corn Expressing Sense Transcripts of Corn Starch Branching Enzyme I
Preparation of the Expression Vector Encoding the Near Full Length Sense Construct Plasmid pBE97 comprises a 1.87 kb fragment of the SBEI cDNA of pBE65 (SEQ ID NO:20) joined in the sense orientation to the 27 kD zein promoter and the 10 kD zein 3' end (FIG. 13). The SBEI fragment encompasses nucleotides 55 through 1919 of the cDNA clone pBE65 and thus contains 117 bp of unknown sequence preceding the remaining 1748 bp of SBEI coding region DNA. This DNA fragment was generated by PCR-mediated site specific mutagenesis to introduce an NcoI site at nucleotide position 53 of the pBE65 sequence. The appropriate nucleotide primers were combined with pBE65 template DNA in a standard PCR reaction defined in Example 1. The PCR fragment that was generated contains a ClaI site followed by an NcoI site and terminates at nucleotide 612 of the pBE65 sequence. This DNA fragment was digested with ClaI and PstI and exchanged with the corresponding region in pBE65 to give pBE79. pBE79 was digested with BstEII and rendered blunt-ended by reaction with the Klenow fragment of DNA polymerase (Maniatis). The DNA fragment was liberated by partial digestion with NcoI, fractionated by electrophoresis on a low melting point agarose gel, and ligated to the NcoI-SmaI fragment of pML1 03 described in Example 1. Transformants in *E. coli* XL-Blue were screened for the presence of the SBEI fragment by restriction enzyme digestion with NcoI and BamHI. From this analysis, pBE88 was identified. pBE88 was subjected to partial digestion with BamHI and the 3.87 kb fragment containing the 27 kD zein-truncated SBEI-10 kD zein chimeric gene was isolated by electrophoresis on a 0.7% low melting point agarose gel (Maniatis). The DNA fragment was cloned into BaiHi digested vector pKS 17 described in Example 4. The resultant plasmid containing the 27 kD zein-truncated SBEI-10 kD zein insert in pKS 17 is termed pBE97.

Two additional sense constructs of maize SBEI were made: pBE110 and pBE111. The full length and truncated sense fragments of these constructs were generated by removal of the artifactual 5' sequences of pBE65 and replacement with the correct 5' terminal sequences of the SBEI coding region. In order to generate a full length sense construct, the plasmid pBE79 described above was modified to incorporate a SmaI restriction site following nt 2674 of the insert sequence of pBE65. To accomplish this, a 805 bp 3' fragment of SBEI cDNA was obtained by PCR using the oligonucleotide pair BE15 (SEQ ID NO:11) and BE67 (SEQ ID NO:21):

BE15
5'-AAGCTTGAATTCCTTGGAGGTGATGGCTAC-3' (SEQ ID NO: 11)
BE67
5'-CGCGGATCCCGGGTTCCAAGGGCGCCAGCGG-3' (SEQ ID NO: 21)

and pBE65 as the template DNA in a standard PCR reaction mixture as defined in Example 1. The PCR product was digested with the restriction enzymes BstEII and SmaI and the digestion product cloned into BstEII and SmaI digested pBE79 to give pBE83. The SBEI coding region fragment of pBE83 was subcloned into the vector pCC6 in two steps: first as an NcoI-SmaI fragment representing the 3' end and then as an NcoI fragment representing the 5' end of the coding region fragment. The vector pCC6 contains a 924 bp EcoRI-NcoI promoter fragment of the maize 10 kD zein gene followed by a 453 bp NcoI-SmaI fragment bearing the 10 kD zein coding region and a 944 bp 3' segment of the 10 kD zein gene in the cloning vector pTZ 18R (Pharmacia). The pCC6 derivative which contains the NcoI-SmaI SBEI fragment is designated pBE85. pBE85 was subjected to partial digestion with PvuII and the 4.7 kb 10 kD zein-SBEI-10 kD zein fragment was inserted into PvuII digested pKS17 (Example 4). The resultant construct designated pBE98, contains 110 bp of unidentified sequence at the 5' end of SBEI cDNA segment. The correct 5' sequence of the SBEI cDNA was obtained by PCR using oligonucleotides BE101 (SEQ ID NO:22) and BB3 (SEQ ID NO:23):

BE101
5'-AACTGCAGAAGGATCCCATGGTGTGCCTC GTGTCGCCC-3' (SEQ ID NO:22)

BB3 5'-GGATGCTTAAATGTGTACC-3' (SEQ ID NO:23)

and lambda DNA prepared from plate lysates of a 19 DAP corn endosperm cDNA library (Stratagene) as the template. The 748 bp PCR product was digested with NcoI and SstI to yield a 673 bp fragment. This DNA segment was exchanged with the corresponding region in pBE98 to give pBE110. The construct pBE110 is 7203 bp in length and consists of a 2565 bp segment of SBEI cDNA (SEQ ID NO:24) that includes the entire 823 amino acids of the SBEI coding region and 96 bp of 3' untranslated DNA (FIG. 14). The SBEI DNA fragment is preceded by the promoter region of the maize 10 kD zein gene and is followed by the 3' end of the maize 10 kD zein gene.

The truncated sense SBEI construct pBE111 was generated by assembling a shortened SBEI coding region fragment in the vector pBC24. pBC24 is a pSK+ derivative in which the XbaI site has been blunted by reaction with the Klenow fragment of DNA polymerase and ligated to NcoI linkers. pBC24 thus lacks the XbaI site and contains a unique NcoI site in the polylinker region. The 5' SBEI fragment described above was digested with the restriction enzymes NcoI and BamHI and the 694 bp fragment was cloned into NcoI-BamHI digested pBC24. This intermediate was then digested with BamHI and SmaI and ligated to the 1874 bp BamHI-SmaI fragment of pBE83 to yield pBE112. pBE112 was digested with BstEII, reacted with Klenow and then subjected to partial digestion with NcoI. The liberated 1809 bp fragment was cloned into NcoI-partial SmaI digested pBT752. The vector, pBT752 is a derivative of pKS17 described in Example 4 which contains a 27 kD zein-maize high sulfur zein-IO kD zein chimeric gene and lacks the NcoI site at the translational start site of the hygromycin phosphotransferase gene. Analytical digests of the resultant transformants in NovaBlue (Novagen) cells revealed that the 10 kD zein 3' end was removed as a SmaI fragment during the cloning procedure. This 963 bp SmaI segment was thus isolated from pBT752 and inserted into a blunted HindIII site that is located just downstream from BstEII/SmaI junction in the intermediate plasmid, pBE110.5. Transformants were screened by digestion with DraI in order to determine the orientation of the 3' end fragment relative to the chimeric SBEI gene. From this analysis, pBE111 was identified. pBE111 contains an 1809 bp fragment of the SBEI cDNA (SEQ ID NO:25) which is preceded by the 27 kD zein promoter and is followed by the 10 kD zein 3' end (FIG. 15).

Example 7

Use of Transgenic Corn Expressing Antisense Transcripts of Corn Starch Branching Enzyme IIb in Combination with the Waxy Mutant A corn line carrying the 3' antisense transcript of corn starch branching enzyme IIb (pBE 44) was crossed with the well characterized corn starch mutant, waxy (wx). Individual segregants homozygous for the waxy mutation were identified in the progeny of this cross. Kernels from line XAY00096 (homozygous wx) carrying the 3' antisense construct were selected. Starch was extracted from these kernels and subjected to Rapid Visco Analyzer pasting analysis as described in Example 1. Waxy (wx) and the homozygous double mutant, amylose extender waxy (ae wx), are shown for comparative purposes. A unique functionality was observed for line XAY00096 in FIG. 16. As can be seen from FIG. 16, the pasting properties of the XAY00096 starch increased the pasting temperature as compared to waxy, but was lower than that of the homozygous ae wx. Viscosity was much higher than that of ae wx and was retained even after cooling, unlike wx which loses viscosity during pasting. This novel starch thus leads to unique pasting properties that are distinct than those observed in waxy alone, in the SBEIIb null mutation (ae) in the combination of these two mutants (ae wx), or in transgenic line alone. The instant invention thus demonstrates the ability to produce starch with unique functionality by combining transgenic lines with known starch mutants.

Example 8

Use of Transgenic Corn Expressing Antisense Transcripts of Corn Starch Branching Enzyme I in Combinations with the Amylose-Extender (ae) Mutant A corn line carrying the 5' antisense transcript of corn starch branching enzyme I (pBE 69) was crossed with the well characterized corn starch mutant, amylose-extender (ae). F1 individuals from this cross were grown to maturity and selfed to produce F2 seeds segregating for all possible combinations of the ae mutation and the SBE I antisense event. Forty-eight single kernels were milled to produce single seed starch as described previously. Single seed starches were enzymatically debranched as described above. Debranched starches were lyophilized and redisolved in DMSO for analysis by gel permeation chromatography (GPC). Ten lL of debranched starch was injected on a Waters 2690 Separations Module, and run through 3 columns (Polymer Labs, Mini-Mixed Bed-C)) in series at 100° C. and eluted with DMSO at a flow rate of 0.35 mL/min. Sampling interval was 35 minutes. A refractive index detector (Waters) was used with a computer running Waters Millennium Chromatography Manager System (version 2.15.1, Waters Corp.) for detection and data collection and storage, respectively. Retention times of pullulan standards (Standard 1: 380K, 100K, 23.7K, 5.8K, 728 and 180 mw, Standard 2: 853K, 186K, 48K, and 12.2K) were used to establish a linear calibration and to define molecular weight distributions in the Millennium Software for the debranched starch samples.

While high amylose segregants occurred at the expected ¼ frequency for the recessive ae mutation, ¼ of these high amylose segregants had a more extreme phenotype (higher amylose and long chain amylopectin content) than the typical ae segregants. In Table 10 the proportion of the total starch was determined for 24 ranges of degree of polymerization (DP) spanning both the amylose and amylopectin portions of the chromatogram of representative normal, ae, and extreme segregants from the F2 ear.

TABLE 10

Proportion of total starch in various DP ranges. Debranched Starches from extreme, ae, and normal segregants on the F2 ear are shown

| DP range | Extreme Segregant | Typical ae Segregant | Normal Segregant |
| --- | --- | --- | --- |
| >5k | 3.11% | 2.56% | 3.09% |
| 3–5k | 4.36% | 3.47% | 2.93% |
| 1.8–3k | 5.66% | 4.55% | 3.13% |
| 1.2–1.8k | 5.45% | 4.42% | 2.60% |
| 0.9–1.2k | 4.34% | 3.53% | 1.88% |
| 600–900 | 6.78% | 5.50% | 2.75% |
| 400–600 | 6.77% | 5.41% | 2.56% |
| 250–400 | 7.97% | 6.23% | 2.77% |
| 150–250 | 7.25% | 5.73% | 2.16% |
| 90–150 | 7.22% | 6.64% | 2.31% |
| 60–90 | 5.84% | 6.52% | 3.40% |
| 48–60 | 3.53% | 4.33% | 3.11% |
| 40–48 | 2.92% | 3.69% | 3.10% |
| 32–40 | 3.34% | 4.26% | 4.08% |
| 28–32 | 2.21% | 2.82% | 3.06% |
| 24–28 | 2.43% | 3.15% | 3.84% |
| 21–24 | 2.00% | 2.65% | 3.63% |
| 18–21 | 2.47% | 3.34% | 5.13% |
| 15–18 | 2.92% | 4.01% | 7.01% |
| 13–15 | 2.40% | 3.31% | 6.49% |
| 11–15 | 2.45% | 3.35% | 7.15% |
| 9–11 | 2.53% | 3.40% | 7.70% |
| 7–9 | 2.90% | 3.68% | 8.41% |
| 5–7 | 3.17% | 3.45% | 7.73% |

For purposes of comparison to data reported above the percentage area in appropriate DP ranges was summed to give values for A and B1 chains, B2, B3 and B4+ chains of the amylopectin portion of the chromatogram. The proportion of the total area above DP 150 was used to determine amylose content.

TABLE 11

Percentage Difference of Branch Chain Distribution of Amylopectin (expressed as A + B1, B2, B3 and B4+) and Amylose Content (% of Total Starch) from Starch Isolated from F2 Kernels Containing the 5' Antisense Transcript of Corn SBEI and the ae mutation compared to normal segregants on the same ear. DP range is indicated in parentheses

|  | A + B1 (5–15) | B2 (15–32) | B3 (32–60) | B4+ (60–150) | Amylose (>150) |
| --- | --- | --- | --- | --- | --- |
| Extreme Segregant | 56.5 | 83.6 | 150.0 | 360.7 | 216.6 |
| Typical ae Segregant | 59.6 | 91.5 | 155.2 | 299.8 | 173.5 |

As can be seen in Tables 10 and 11, the combination of the 5' Anti-Sense construct for SBEI with the ae mutation results in an F2 ear segregating high-amylose kernels with a starch structure that is higher in amylose and long chain amylopectin branches than is typical of the ae mutation alone. The instant invention thus demonstrates that down regulating the SBEI gene in the presence of the ae mutation provides a method for further increasing amylose content in ae mutant starches.

```
                          SEQUENCE LISTING (1) GENERAL INFORMATION:

(iii) NUMBER OF SEQUENCES:  25

(2) INFORMATION FOR SEQ ID NO:1:

(i) SEQUENCE CHARACTERISTICS:
         (A) LENGTH:  2665 base pairs
         (B) TYPE:  nucleic acid
         (C) STRANDEDNESS:  single
         (D) TOPOLOGY:  linear (ii) MOLECULE TYPE:  DNA (genomic)

(ix) FEATURE:
         (A) NAME/KEY:  CDS
         (B) LOCATION:  79..2476

(xi) SEQUENCE DESCRIPTION:  SEQ ID NO:1:
```

-continued

```
ACCCGGATTT CGCTCTTGCG GTCGCTGGGG TTTTAGCATT GGCTGATCAG TTCGATCCGA         60

TCCGGCTGCG AAGGCGAG ATG GCG TTC CGG GTT TCT GGG GCG GTG CTC GGT         111
                    Met Ala Phe Arg Val Ser Gly Ala Val Leu Gly
                     1           5                      10

GGG GCC GTA AGG GCT CCC CGA CTC ACC GGC GGC GGG GAG GGT AGT CTA         159
Gly Ala Val Arg Ala Pro Arg Leu Thr Gly Gly Gly Glu Gly Ser Leu
            15                  20                  25

GTC TTC CGG CAC ACC GGC CTC TTC TTA ACT CGG GGT GCT CGA GTT GGA         207
Val Phe Arg His Thr Gly Leu Phe Leu Thr Arg Gly Ala Arg Val Gly
                30                  35                  40

TGT TCG GGG ACG CAC GGG GCC ATG CGC GCG GCG GCG GCC AGG AAG             255
Cys Ser Gly Thr His Gly Ala Met Arg Ala Ala Ala Ala Arg Lys
        45                  50                  55

GCG GTC ATG GTT CCT GAG GGC GAG AAT GAT GGC CTC GCA TCA AGG GCT         303
Ala Val Met Val Pro Glu Gly Glu Asn Asp Gly Leu Ala Ser Arg Ala
 60              65                  70                  75

GAC TCG GCT CAA TTC CAG TCG GAT GAA CTG GAG GTA CCA GAC ATT TCT         351
Asp Ser Ala Gln Phe Gln Ser Asp Glu Leu Glu Val Pro Asp Ile Ser
                 80                  85                  90

GAA GAG ACA ACG TGC GGT GCT GGT GTG GCT GAT GCT CAA GCC TTG AAC         399
Glu Glu Thr Thr Cys Gly Ala Gly Val Ala Asp Ala Gln Ala Leu Asn
             95                 100                 105

AGA GTT CGA GTG GTC CCC CCA CCA AGC GAT GGA CAA AAA ATA TTC CAG         447
Arg Val Arg Val Val Pro Pro Pro Ser Asp Gly Gln Lys Ile Phe Gln
        110                 115                 120

ATT GAC CCC ATG TTG CAA GGC TAT AAG TAC CAT CTT GAG TAT CGG TAC         495
Ile Asp Pro Met Leu Gln Gly Tyr Lys Tyr His Leu Glu Tyr Arg Tyr
    125                 130                 135

AGC CTC TAT AGA AGA ATC CGT TCA GAC ATT GAT GAA CAT GAA GGA GGC         543
Ser Leu Tyr Arg Arg Ile Arg Ser Asp Ile Asp Glu His Glu Gly Gly
140                 145                 150                 155

TTG GAA GCC TTC TCC CGT AGT TAT GAG AAG TTT GGA TTT AAT GCC AGC         591
Leu Glu Ala Phe Ser Arg Ser Tyr Glu Lys Phe Gly Phe Asn Ala Ser
                160                 165                 170

GCG GAA GGT ATC ACA TAT CGA GAA TGG GCT CCT GGA GCA TTT TCT GCA         639
Ala Glu Gly Ile Thr Tyr Arg Glu Trp Ala Pro Gly Ala Phe Ser Ala
            175                 180                 185

GCA TTG GTG GGT GAC TTC AAC AAC TGG GAT CCA AAT GCA GAT CGT ATG         687
Ala Leu Val Gly Asp Phe Asn Asn Trp Asp Pro Asn Ala Asp Arg Met
        190                 195                 200

AGC AAA AAT GAG TTT GGT GTT TGG GAA ATT TTT CTG CCT AAC AAT GCA         735
Ser Lys Asn Glu Phe Gly Val Trp Glu Ile Phe Leu Pro Asn Asn Ala
    205                 210                 215

GAT GGT ACA TCA CCT ATT CCT CAT GGA TCT CGT GTA AAG GTG AGA ATG         783
Asp Gly Thr Ser Pro Ile Pro His Gly Ser Arg Val Lys Val Arg Met
220                 225                 230                 235

GAT ACT CCA TCA GGG ATA AAG GAT TCA ATT CCA GCC TGG ATC AAG TAC         831
Asp Thr Pro Ser Gly Ile Lys Asp Ser Ile Pro Ala Trp Ile Lys Tyr
                240                 245                 250

TCA GTG CAG GCC CCA GGA GAA ATA CCA TAT GAT GGG ATT TAT TAT GAT         879
Ser Val Gln Ala Pro Gly Glu Ile Pro Tyr Asp Gly Ile Tyr Tyr Asp
            255                 260                 265

CCT CCT GAA GAG GTA AAG TAT GTG TTC AGG CAT GCG CAA CCT AAA CGA         927
Pro Pro Glu Glu Val Lys Tyr Val Phe Arg His Ala Gln Pro Lys Arg
        270                 275                 280

CCA AAA TCA TTG CGG ATA TAT GAA ACA CAT GTC GGA ATG AGT AGC CCG         975
Pro Lys Ser Leu Arg Ile Tyr Glu Thr His Val Gly Met Ser Ser Pro
    285                 290                 295
```

```
GAA CCG AAG ATA AAC ACA TAT GTA AAC TTT AGG GAT GAA GTC CTC CCA     1023
Glu Pro Lys Ile Asn Thr Tyr Val Asn Phe Arg Asp Glu Val Leu Pro
300                 305                 310                 315

AGA ATA AAA AAA CTT GGA TAC AAT GCA GTG CAA ATA ATG GCA ATC CAA     1071
Arg Ile Lys Lys Leu Gly Tyr Asn Ala Val Gln Ile Met Ala Ile Gln
        320                 325                 330

GAG CAC TCA TAT TAT GGA AGC TTT GGA TAC CAT GTA ACT AAT TTT TTT     1119
Glu His Ser Tyr Tyr Gly Ser Phe Gly Tyr His Val Thr Asn Phe Phe
                335                 340                 345

GCG CCA AGT AGT CGT TTT GGT ACC CCA GAA GAT TTG AAG TCT TTG ATT     1167
Ala Pro Ser Ser Arg Phe Gly Thr Pro Glu Asp Leu Lys Ser Leu Ile
            350                 355                 360

GAT AGA GCA CAT GAG CTT GGT TTG CTA GTT CTC ATG GAT GTG GTT CAT     1215
Asp Arg Ala His Glu Leu Gly Leu Leu Val Leu Met Asp Val Val His
365                 370                 375

AGT CAT GCG TCA AGT AAT ACT CTG GAT GGG TTG AAT GGT TTT GAT GGT     1263
Ser His Ala Ser Ser Asn Thr Leu Asp Gly Leu Asn Gly Phe Asp Gly
380                 385                 390                 395

ACA GAT ACA CAT TAC TTT CAC AGT GGT CCA CGT GGC CAT CAC TGG ATG     1311
Thr Asp Thr His Tyr Phe His Ser Gly Pro Arg Gly His His Trp Met
                400                 405                 410

TGG GAT TCT CGC CTA TTT AAC TAT GGG AAC TGG GAA GTT TTA AGA TTT     1359
Trp Asp Ser Arg Leu Phe Asn Tyr Gly Asn Trp Glu Val Leu Arg Phe
            415                 420                 425

CTT CTC TCC AAT GCT AGA TGG TGG CTC GAG GAA TAT AAG TTT GAT GGT     1407
Leu Leu Ser Asn Ala Arg Trp Trp Leu Glu Glu Tyr Lys Phe Asp Gly
            430                 435                 440

TTC CGT TTT GAT GGT GTG ACC TCC ATG ATG TAC ACT CAC CAC GGA TTA     1455
Phe Arg Phe Asp Gly Val Thr Ser Met Met Tyr Thr His His Gly Leu
        445                 450                 455

CAA GTA ACA TTT ACG GGG AAC TTC AAT GAG TAT TTT GGC TTT GCC ACC     1503
Gln Val Thr Phe Thr Gly Asn Phe Asn Glu Tyr Phe Gly Phe Ala Thr
460                 465                 470                 475

GAT GTA GAT GCA GTG GTT TAC TTG ATG CTG GTA AAT GAT CTA ATT CAT     1551
Asp Val Asp Ala Val Val Tyr Leu Met Leu Val Asn Asp Leu Ile His
                480                 485                 490

GGA CTT TAT CCT GAG GCT GTA ACC ATT GGT GAA GAT GTT AGT GGA ATG     1599
Gly Leu Tyr Pro Glu Ala Val Thr Ile Gly Glu Asp Val Ser Gly Met
            495                 500                 505

CCT ACA TTT GCC CTT CCT GTT CAC GAT GGT GGG GTA GGT TTT GAC TAT     1647
Pro Thr Phe Ala Leu Pro Val His Asp Gly Gly Val Gly Phe Asp Tyr
            510                 515                 520

CGG ATG CAT ATG GCT GTG GCT GAC AAA TGG ATT GAC CTT CTC AAG CAA     1695
Arg Met His Met Ala Val Ala Asp Lys Trp Ile Asp Leu Leu Lys Gln
525                 530                 535

AGT GAT GAA ACT TGG AAG ATG GGT GAT ATT GTG CAC ACA CTG ACA AAT     1743
Ser Asp Glu Thr Trp Lys Met Gly Asp Ile Val His Thr Leu Thr Asn
540                 545                 550                 555

AGG AGG TGG TTA GAG AAG TGT GTA ACT TAT GCT GAA AGT CAT GAT CAA     1791
Arg Arg Trp Leu Glu Lys Cys Val Thr Tyr Ala Glu Ser His Asp Gln
                560                 565                 570

GCA TTA GTC GGC GAC AAG ACT ATT GCG TTT TGG TTG ATG GAC AAG GAT     1839
Ala Leu Val Gly Asp Lys Thr Ile Ala Phe Trp Leu Met Asp Lys Asp
            575                 580                 585

ATG TAT GAT TTC ATG GCC CTC GAT AGA CCT TCA ACT CCT ACC ATT GAT     1887
Met Tyr Asp Phe Met Ala Leu Asp Arg Pro Ser Thr Pro Thr Ile Asp
            590                 595                 600

CGT GGG ATA GCA TTA CAT AAG ATG ATT AGA CTT ATC ACA ATG GGT TTA     1935
Arg Gly Ile Ala Leu His Lys Met Ile Arg Leu Ile Thr Met Gly Leu
605                 610                 615
```

-continued

```
GGA GGA GAG GGC TAT CTT AAT TTC ATG GGA AAT GAG TTT GGA CAT CCT      1983
Gly Gly Glu Gly Tyr Leu Asn Phe Met Gly Asn Glu Phe Gly His Pro
620                 625                 630                 635

GAA TGG ATA GAT TTT CCA AGA GGT CCG CAA AGA CTT CCA AGT GGT AAG      2031
Glu Trp Ile Asp Phe Pro Arg Gly Pro Gln Arg Leu Pro Ser Gly Lys
                640                 645                 650

TTT ATT CCA GGG AAT AAC AAC AGT TAT GAC AAA TGT CGT CGA AGA TTT      2079
Phe Ile Pro Gly Asn Asn Asn Ser Tyr Asp Lys Cys Arg Arg Arg Phe
            655                 660                 665

GAC CTG GGT GAT GCA GAC TAT CTT AGG TAT CAT GGT ATG CAA GAG TTT      2127
Asp Leu Gly Asp Ala Asp Tyr Leu Arg Tyr His Gly Met Gln Glu Phe
        670                 675                 680

GAT CAG GCA ATG CAA CAT CTT GAG CAA AAA TAT GAA TTC ATG ACA TCT      2175
Asp Gln Ala Met Gln His Leu Glu Gln Lys Tyr Glu Phe Met Thr Ser
    685                 690                 695

GAT CAC CAG TAT ATT TCC CGG AAA CAT GAG GAG GAT AAG GTG ATT GTG      2223
Asp His Gln Tyr Ile Ser Arg Lys His Glu Glu Asp Lys Val Ile Val
700                 705                 710                 715

TTC GAA AAG GGA GAT TTG GTA TTT GTG TTC AAC TTC CAC TGC AAC AAC      2271
Phe Glu Lys Gly Asp Leu Val Phe Val Phe Asn Phe His Cys Asn Asn
                720                 725                 730

AGC TAT TTT GAC TAC CGT ATT GGT TGT CGA AAG CCT GGG GTG TAT AAG      2319
Ser Tyr Phe Asp Tyr Arg Ile Gly Cys Arg Lys Pro Gly Val Tyr Lys
            735                 740                 745

GTG GTC TTG GAC TCC GAC GCT GGA CTA TTT GGT GGA TTT AGC AGG ATC      2367
Val Val Leu Asp Ser Asp Ala Gly Leu Phe Gly Gly Phe Ser Arg Ile
        750                 755                 760

CAT CAC GCA GCC GAG CAC TTC ACC GCC GAC TGT TCG CAT GAT AAT AGG      2415
His His Ala Ala Glu His Phe Thr Ala Asp Cys Ser His Asp Asn Arg
    765                 770                 775

CCA TAT TCA TCC TCG GTT TAT ACA CCA AGC AGA ACA TGT GTC GTC TAT      2463
Pro Tyr Ser Ser Ser Val Tyr Thr Pro Ser Arg Thr Cys Val Val Tyr
780                 785                 790                 795

GCT CCA GTG GAG T GATAGCGGGG TACTCGTTGC TGCGCGGCAT GTGTGGGCT         2516
Ala Pro Val Glu

GTCGATGTGA GGAAAAACCT TCTTCCAAAA CCGGCAGATG CATGCATGCA TGCTACAATA    2576

AGGTTCTGAT ACTTTAATCG ATGCTGGAAA GCCCATGCAT CTCGCTGCGT TGTCCTCTCT    2636

ATATATATAA GACCTTCAAG GTGTCAATT                                       2665

(2) INFORMATION FOR SEQ ID NO:2:

(i) SEQUENCE CHARACTERISTICS:
          (A) LENGTH:  414 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:2:

GACACCTTGA AGGTCTTATA TATATAGAGA GGACAACGCA GCGAGATGCA TGGGCTTTCC     60

AGCATCGATT AAAGTATCAG AACCTTATTG TAGCATGCAT GCATGCATCT GCCGGTTTTG    120

GAAGAAGGTT TTTCCTCACA TCGACAGCCC ACACATGCC GCGCAGCAAC GAGTACCCCG    180

CTATCACTCC ACTGGAGCAT AGACGACACA TGTTCTGCTT GGTGTATAAA CCGAGGATGA    240

ATATGGCCTA TTATCATGCG AACAGTCGGC GGTGAAGTGC TCGGCTGCGT GATGGATCCT    300

GCTAAATCCA CCAAATAGTC CAGCGTCGGA GTCCAAGACC ACCTTATACA CCCCAGGCTT    360
```

```
TCGACAACCA ATACGGTAGT CAAAATAGCT GTTGTTGCAG TGGAAGTTGA ACAC          414
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GAATTCCCGG GGTGTTCAAC TTCCACTGC                                     29
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GAATTCCATG GGACACCTTG AAGGTCTT                                      28
```

(2) INFORMATION FOR SEQ ID NO:5:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TCTATAGAGG CTGTACCGAT ACTCAAGATG GTACTTATAG CCTTGCAACA TGGGGTCAAT    60
CTGGAATATT TTTTGTCCAT CGCTTGGTGG GGGGACCACT CGAACTCTGT TCAAGGCTTG   120
AGCATCAGCC ACACCAGCAC CGCACGTTGT CTCTTCAGAA ATGTCTGGTA CCTCCAGTTC   180
ATCCGACTGG AATTGAGCCG AGTCAGCCCT TGATGCGAGG CCATCATTCT CGCCCTCAGG   240
AACCATGACC GCCTTCCTGG CCGCGGCCGC CGCGCGCATG GCCCCGTGCG TCCCCGAACA   300
TCCAACTCGA GCACCCCGAG TTAAGAAGAG GCCGGTGTGC CGGAAGACTA GACTACCCTC   360
CCCGCCGCCG GTGAGTCGGG GAGCCCTTAC GGCCCCACCG AGCACCGCCC CAGAAACCCG   420
GAACGCCATC TCGCCTTCGC AGCCGGATCG GATCGAACTG ATCAGCCAAT GCTAAAACCC   480
CAGCGACCGC AAGAGCGAAA TCCGGGT                                      507
```

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GAATTCCCGG GACCCGGATT TCGCTCTT                                      28
```

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GAATTCCATG GTCTATAGAG GCTGTACCG                                  29
```

(2) INFORMATION FOR SEQ ID NO:8:

(i) SEQUENCE CHARACTERISTICS:
        (A) LENGTH: 2165 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
AATTCATATT TTTGCTCAAG ATGTTGCATT GCCTGATCAA ACTCTTGCAT ACCATGATAC    60
CTAAGATAGT CTGCATCACC CAGGTCAAAT CTTCGACGAC ATTTGTCATA ACTGTTGTTA   120
TTCCCTGGAA TAAACTTACC ACTTGGAAGT CTTTGCGGAC CTCTTGGAAA ATCTATCCAT   180
TCAGGATGTC CAAACTCATT TCCCATGAAA TTAAGATAGC CCTCTCCTCC TAAACCCATT   240
GTGATAAGTC TAATCATCTT ATGTAATGCT ATCCCACGAT CAATGGTAGG AGTTGAAGGT   300
CTATCGAGGG CCATGAAATC ATACATATCC TTGTCCATCA ACCAAAACGC AATAGTCTTG   360
TCGCCGACTA ATGCTTGATC ATGACTTTCA GCATAAGTTA CACACTTCTC TAACCACCTC   420
CTATTTGTCA GTGTGTGCAC AATATCACCC ATCTTCCAAG TTTCATCACT TTGCTTGAGA   480
AGGTCAATCC ATTTGTCAGC CACAGCCATA TGCATCCGAT AGTCAAAACC TACCCCACCA   540
TCGTGAACAG GAAGGGCAAA TGTAGGCATT CCACTAACAT CTTCACCAAT GGTTACAGCC   600
TCAGGATAAA GTCCATGAAT TAGATCATTT ACCAGCATCA AGTAAACCAC TGCATCTACA   660
TCGGTGGCAA AGCCAAAATA CTCATTGAAG TTCCCCGTAA ATGTTACTTG TAATCCGTGG   720
TGAGTGTACA TCATGGAGGT CACACCATCA AAACGGAAAC CATCAAACTT ATATTCCTCG   780
AGCCACCATC TAGCATTGGA GAGAAGAAAT CTTAAAACTT CCCAGTTCCC ATAGTTAAAT   840
AGGCGAGAAT CCCACATCCA GTGATGGCCA CGTGGACCAC TGTGAAAGTA ATGTGTATCT   900
GTACCATCAA AACCATTCAA CCCATCCAGA GTATTACTTG ACGCATGACT ATGAACCACA   960
TCCATGAGAA CTAGCAAACC AAGCTCATGT GCTCTATCAA TCAAAGACTT CAAATCTTCT  1020
GGGGTACCAA AACGACTACT TGGCGCAAAA AAATTAGTTA CATGGTATCC AAAGCTTCCA  1080
TAATATGAGT GCTCTTGGAT TGCCATTATT TGCACTGCAT TGTATCCAAG TTTTTTTATT  1140
CTTGGGAGGA CTTCATCCCT AAAGTTTACA TATGTGTTTA TCTTCGGTTC CGGGCTACTC  1200
ATTCCGACAT GTGTTTCATA TATCCGCAAT GATTTTGGTC GTTTAGGTTG CGCATGCCTG  1260
AACACATACT TTACCTCTTC AGGAGGATCA TAATAAATCC CATCATATGG TATTTCTCCT  1320
GGGGCCTGCA CTGAGTACTT GATCCAGGCT GGAATTGAAT CCTTTATCCC TGATGGAGTA  1380
TCCATTCTCA CCTTTACACG AGATCCATGA GGAATAGGTG ATGTACCATC TGCATTGTTA  1440
GGCAGAAAAA TTTCCCAAAC ACCAAACTCA TTTTTGCTCA TACGATCTGC ATTTGGATCC  1500
CAGTTGTTGA CGTCACCCAC CAATGCTGCA GAAAATGCTC CAGGAGCCCA TTCTCGATAT  1560
```

-continued

```
GTGATACCTT CCGCGCTGGC ATTAAATCCA AACTTCTCAT AACTACGGGA GAAGGCTTCC      1620

AAGCCTCCTT CATGTTCATC AATGTCTGAA CGGATTCTTC TATAGAGGCT GTACCGATAC      1680

TCAAGATGGT ACTTATAGCC TTGCAACATG GGGTCAATCT GGAATATTTT TTGTCCATCG      1740

CTTGGTGGGG GGACCACTCG AACTCTGTTC AAGGCTTGAG CATCAGCCAC ACCAGCACCG      1800

CACGTTGTCT CTTCAGAAAT GTCTGGTACC TCCAGTTCAT CCGACTGGAA TTGAGCCGAG      1860

TCAGCCCTTG ATGCGAGGCC ATCATTCTCG CCCTCAGGAA CCATGACCGC CTTCCTGGCC      1920

GCGGCCGCCG CGCGCATGGC CCCGTGCGTC CCCGAACATC CAACTCGAGC ACCCCGAGTT      1980

AAGAAGAGGC CGGTGTGCCG GAAGACTAGA CTACCCTCCC CGCCGCCGGT GAGTCGGGGA      2040

GCCCTTACGG CCCCACCGAG CACCGCCCCA GAAACCCGGA ACGCCATCTC GCCTTCGCAG      2100

CCGGATCGGA TCGAACTGAT CAGCCAATGC TAAAACCCCA GCGACCGCAA GAGCGAAATC      2160

CGGGT                                                                 2165
```

(2) INFORMATION FOR SEQ ID NO:9:

(i) SEQUENCE CHARACTERISTICS:
        (A) LENGTH: 2087 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATGGCGTTCC GGGTTTCTGG GGCGGTGCTC GGTGGGGCCG TAAGGGCTCC CCGACTCACC        60

GGCGGCGGGG AGGGTAGTCT AGTCTTCCGG CACACCGGCC TCTTCTTAAC TCGGGGTGCT       120

CGAGTTGGAT GTTCGGGGAC GCACGGGGCC ATGCGCGCGG CGGCCGCGGC CAGGAAGGCG       180

GTCATGGTTC CTGAGGGCGA GAATGATGGC CTCGCATCAA GGGCTGACTC GGCTCAATTC       240

CAGTCGGATG AACTGGAGGT ACCAGACATT TCTGAAGAGA CAACGTGCGG TGCTGGTGTG       300

GCTGATGCTC AAGCCTTGAA CAGAGTTCGA GTGGTCCCCC CACCAAGCGA TGGACAAAAA       360

ATATTCCAGA TTGACCCCAT GTTGCAAGGC TATAAGTACC ATCTTGAGTA TCGGTACAGC       420

CTCTATAGAA GAATCCGTTC AGACATTGAT GAACATGAAG GAGGCTTGGA AGCCTTCTCC       480

CGTAGTTATG AGAAGTTTGG ATTTAATGCC AGCGCGGAAG GTATCACATA TCGAGAATGG       540

GCTCCTGGAG CATTTTCTGC AGCATTGGTG GGTGACTTCA ACAACTGGGA TCCAAATGCA       600

GATCGTATGA GCAAAAATGA GTTTGGTGTT TGGGAAATTT TTCTGCCTAA CAATGCAGAT       660

GGTACATCAC CTATTCCTCA TGGATCTCGT GTAAAGGTGA GAATGGATAC TCCATCAGGG       720

ATAAAGGATT CAATTCCAGC CTGGATCAAG TACTCAGTGC AGGCCCCAGG AGAAATACCA       780

TATGATGGGA TTTATTATGA TCCTCCTGAA GAGGTAAAGT ATGTGTTCAG GCATGCGCAA       840

CCTAAACGAC CAAAATCATT GCGGATATAT GAAACACATG TCGGAATGAG TAGCCCGGAA       900

CCGAAGATAA ACACATATGT AAACTTTAGG GATGAAGTCC TCCCAAGAAT AAAAAAACTT       960

GGATACAATG CAGTGCAAAT AATGGCAATC CAAGAGCACT CATATTATGG AAGCTTTGGA      1020

TACCATGTAA CTAATTTTTT TGCGCCAAGT AGTCGTTTTG GTACCCCAGA AGATTTGAAG      1080

TCTTTGATTG ATAGAGCACA TGAGCTTGGT TTGCTAGTTC TCATGGATGT GGTTCATAGT      1140

CATGCGTCAA GTAATACTCT GGATGGGTTG AATGGTTTTG ATGGTACAGA TACACATTAC      1200

TTTCACAGTG GTCCACGTGG CCATCACTGG ATGTGGGATT CTCGCCTATT TAACTATGGG      1260

AACTGGGAAG TTTTAAGATT TCTTCTCTCC AATGCTAGAT GGTGGCTCGA GGAATATAAG      1320
```

```
TTTGATGGTT TCCGTTTTGA TGGTGTGACC TCCATGATGT ACACTCACCA CGGATTACAA    1380

GTAACATTTA CGGGGAACTT CAATGAGTAT TTTGGCTTTG CCACCGATGT AGATGCAGTG    1440

GTTTACTTGA TGCTGGTAAA TGATCTAATT CATGGACTTT ATCCTGAGGC TGTAACCATT    1500

GGTGAAGATG TTAGTGGAAT GCCTACATTT GCCCTTCCTG TTCACGATGG TGGGGTAGGT    1560

TTTGACTATC GGATGCATAT GGCTGTGGCT GACAAATGGA TTGACCTTCT CAAGCAAAGT    1620

GATGAAACTT GGAAGATGGG TGATATTGTG CACACACTGA CAAATAGGAG GTGGTTAGAG    1680

AAGTGTGTAA CTTATGCTGA AAGTCATGAT CAAGCATTAG TCGGCGACAA GACTATTGCG    1740

TTTTGGTTGA TGGACAAGGA TATGTATGAT TTCATGGCCC TCGATAGACC TTCAACTCCT    1800

ACCATTGATC GTGGGATAGC ATTACATAAG ATGATTAGAC TTATCACAAT GGGTTTAGGA    1860

GGAGAGGGCT ATCTTAATTT CATGGGAAAT GAGTTTGGAC ATCCTGAATG GATAGATTTT    1920

CCAAGAGGTC CGCAAAGACT TCCAAGTGGT AAGTTTATTC CAGGGAATAA CAACAGTTAT    1980

GACAAATGTC GTCGAAGATT TGACCTGGGT GATGCAGACT ATCTTAGGTA TCATGGTATG    2040

CAAGAGTTTG ATCAGGCAAT GCAACATCTT GAGCAAAAAT ATGAATT                  2087

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AAGCTTGAAT TCTGCTCGGT GATGAGACAC                                       30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AAGCTTGAAT TCCTTGGAGG TGATGGCTAC                                       30

(2) INFORMATION FOR SEQ ID NO:12:

(i) SEQUENCE CHARACTERISTICS:
        (A) LENGTH: 2772 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..2580

(xi) SEQUENCE DESCRIPTION: SEQ ID NO:12:

TGCTGATCGA GTGAGGGAAT TCAGCAGCAG CAGCAGCAGG TAGCATAG CAT AGA TAT       57
                                                    His Arg Tyr
                                                      1

GAC GGC GGC GGA GGT GGA GGC CGC CAA GGA CAT CGC CGA GGA GAA GGC       105
Asp Gly Gly Gly Gly Gly Gly Arg Gln Gly His Arg Arg Gly Glu Gly
```

```
                5                        10                        15
CGT CGT GCC GTT GCC ACC GTC GCC CGC CAA GCC GGC CGA CGA CGA CTC           153
Arg Arg Ala Val Ala Thr Val Ala Arg Gln Ala Gly Arg Arg Arg Leu
 20                      25                      30                  35

CAA GGC CAT CGT CGC TCT TGC TCG CAT GCT GAT CGG GCG GCA CCG CCG           201
Gln Gly His Arg Arg Ser Cys Ser His Ala Asp Arg Ala Ala Pro Pro
                         40                      45                  50

GGG ATC GCG GGT GGC GGC AAT GTG CGC CTG AGT GTG TTG TCT GTC CAG           249
Gly Ile Ala Gly Gly Gly Asn Val Arg Leu Ser Val Leu Ser Val Gln
                 55                      60                      65

TGC AAG GCT CGC CGG TCA GGG GTG CGG AAG GTC AAG AGC AAA TTC GCC           297
Cys Lys Ala Arg Arg Ser Gly Val Arg Lys Val Lys Ser Lys Phe Ala
         70                      75                      80

ACT GCA GCT ACT GTG CAA GAA GAT AAA ACT ATG GCA ACT GCC AAA GGC           345
Thr Ala Ala Thr Val Gln Glu Asp Lys Thr Met Ala Thr Ala Lys Gly
     85                      90                      95

GAT GTC GAC CAT CTC CCC ATA TAC GAC CTG GAC CCC AAG CTG GAG ATA           393
Asp Val Asp His Leu Pro Ile Tyr Asp Leu Asp Pro Lys Leu Glu Ile
100                     105                     110                 115

TTC AAG GAC CAT TTC AGG TAC CGG ATG AAA AGA TTC CTA GAG CAG AAA           441
Phe Lys Asp His Phe Arg Tyr Arg Met Lys Arg Phe Leu Glu Gln Lys
                        120                     125                 130

GGA TCA ATT GAA GAA AAT GAG GGA AGT CTT GAA TCT TTT TCT AAA GGC           489
Gly Ser Ile Glu Glu Asn Glu Gly Ser Leu Glu Ser Phe Ser Lys Gly
                135                     140                     145

TAT TTG AAA TTT GGG ATT AAT ACA AAT GAG GAT GGA ACT GTA TAT CGT           537
Tyr Leu Lys Phe Gly Ile Asn Thr Asn Glu Asp Gly Thr Val Tyr Arg
        150                     155                     160

GAA TGG GCA CCT GCT GCG CAG GAG GCA GAG CTT ATT GGT GAC TTC AAT           585
Glu Trp Ala Pro Ala Ala Gln Glu Ala Glu Leu Ile Gly Asp Phe Asn
165                     170                     175

GAC TGG AAT GGT GCA AAC CAT AAG ATG GAG AAG GAT AAA TTT GGT GTT           633
Asp Trp Asn Gly Ala Asn His Lys Met Glu Lys Asp Lys Phe Gly Val
180                     185                     190                 195

TGG TCG ATC AAA ATT GAC CAT GTC AAA GGG AAA CCT GCC ATC CCT CAC           681
Trp Ser Ile Lys Ile Asp His Val Lys Gly Lys Pro Ala Ile Pro His
                200                     205                     210

AAT TCC AAG GTT AAA TTT CGC TTT CTA CAT GGT GGA GTA TGG GTT GAT           729
Asn Ser Lys Val Lys Phe Arg Phe Leu His Gly Gly Val Trp Val Asp
                215                     220                     225

CGT ATT CCA GCA TTG ATT CGT TAT GCG ACT GTT GAT GCC TCT AAA TTT           777
Arg Ile Pro Ala Leu Ile Arg Tyr Ala Thr Val Asp Ala Ser Lys Phe
        230                     235                     240

GGA GCT CCC TAT GAT GGT GTT CAT TGG GAT CCT CCT GCT TCT GAA AGG           825
Gly Ala Pro Tyr Asp Gly Val His Trp Asp Pro Pro Ala Ser Glu Arg
        245                     250                     255

TAC ACA TTT AAG CAT CCT CGG CCT TCA AAG CCT GCT GCT CCA CGT ATC           873
Tyr Thr Phe Lys His Pro Arg Pro Ser Lys Pro Ala Ala Pro Arg Ile
260                     265                     270                 275

TAT GAA GCC CAT GTA GGT ATG AGT GGT GAA AAG CCA GCA GTA AGC ACA           921
Tyr Glu Ala His Val Gly Met Ser Gly Glu Lys Pro Ala Val Ser Thr
                        280                     285                 290

TAT AGG GAA TTT GCA GAC AAT GTG TTG CCA CGC ATA CGA GCA AAT AAC           969
Tyr Arg Glu Phe Ala Asp Asn Val Leu Pro Arg Ile Arg Ala Asn Asn
                295                     300                     305

TAC AAC ACA GTT CAG TTG ATG GCA GTT ATG GAG CAT TCG TAC TAT GCT          1017
Tyr Asn Thr Val Gln Leu Met Ala Val Met Glu His Ser Tyr Tyr Ala
        310                     315                     320

TCT TTC GGG TAC CAT GTG ACA AAT TTC TTT GCG GTT AGC AGC AGA TCA          1065
```

```
Ser Phe Gly Tyr His Val Thr Asn Phe Phe Ala Val Ser Ser Arg Ser
    325                 330                 335

GGC ACA CCA GAG GAC CTC AAA TAT CTT GTT GAT AAG GCA CAC AGT TTG        1113
Gly Thr Pro Glu Asp Leu Lys Tyr Leu Val Asp Lys Ala His Ser Leu
340                 345                 350                 355

GGT TTG CGA GTT CTG ATG GAT GTT GTC CAT AGC CAT GCA AGT AAT AAT        1161
Gly Leu Arg Val Leu Met Asp Val Val His Ser His Ala Ser Asn Asn
                360                 365                 370

GTC ACA GAT GGT TTA AAT GGC TAT GAT GTT GGA CAA AGC ACC CAA GAG        1209
Val Thr Asp Gly Leu Asn Gly Tyr Asp Val Gly Gln Ser Thr Gln Glu
            375                 380                 385

TCC TAT TTT CAT GCG GGA GAT AGA GGT TAT CAT AAA CTT TGG GAT AGT        1257
Ser Tyr Phe His Ala Gly Asp Arg Gly Tyr His Lys Leu Trp Asp Ser
        390                 395                 400

CGG CTG TTC AAC TAT GCT AAC TGG GAG GTA TTA AGG TTT CTT CTT TCT        1305
Arg Leu Phe Asn Tyr Ala Asn Trp Glu Val Leu Arg Phe Leu Leu Ser
    405                 410                 415

AAC CTG AGA TAT TGG TTG GAT GAA TTC ATG TTT GAT GGC TTC CGA TTT        1353
Asn Leu Arg Tyr Trp Leu Asp Glu Phe Met Phe Asp Gly Phe Arg Phe
420                 425                 430                 435

GAT GGA GTT ACA TCA ATG CTG TAT CAT CAC CAT GGT ATC AAT GTG GGG        1401
Asp Gly Val Thr Ser Met Leu Tyr His His His Gly Ile Asn Val Gly
                440                 445                 450

TTT ACT GGA AAC TAC CAG GAA TAT TTC AGT TTG GAC ACA GCT GTG GAT        1449
Phe Thr Gly Asn Tyr Gln Glu Tyr Phe Ser Leu Asp Thr Ala Val Asp
            455                 460                 465

GCA GTT GTT TAC ATG ATG CTT GCA AAC CAT TTA ATG CAC AAA CTC TTG        1497
Ala Val Val Tyr Met Met Leu Ala Asn His Leu Met His Lys Leu Leu
        470                 475                 480

CCA GAA GCA ACT GTT GTT GCT GAA GAT GTT TCA GGC ATG CCG GTC CTT        1545
Pro Glu Ala Thr Val Val Ala Glu Asp Val Ser Gly Met Pro Val Leu
    485                 490                 495

TGC CGG CCA GTT GAT GAA GGT GGG GTT GGG TTT GAC TAT CGC CTG GCA        1593
Cys Arg Pro Val Asp Glu Gly Gly Val Gly Phe Asp Tyr Arg Leu Ala
500                 505                 510                 515

ATG GCT ATC CCT GAT AGA TGG ATT GAC TAC CTG AAG AAT AAA GAT GAC        1641
Met Ala Ile Pro Asp Arg Trp Ile Asp Tyr Leu Lys Asn Lys Asp Asp
                520                 525                 530

TCT GAG TGG TCG ATG GGT GAA ATA GCG CAT ACT TTG ACT AAC AGG AGA        1689
Ser Glu Trp Ser Met Gly Glu Ile Ala His Thr Leu Thr Asn Arg Arg
            535                 540                 545

TAT ACT GAA AAA TGC ATC GCA TAT GCT GAG AGC CAT GAT CAG TCT ATT        1737
Tyr Thr Glu Lys Cys Ile Ala Tyr Ala Glu Ser His Asp Gln Ser Ile
        550                 555                 560

GTT GGC GAC AAA ACT ATT GCA TTT CTC CTG ATG GAC AAG GAA ATG TAC        1785
Val Gly Asp Lys Thr Ile Ala Phe Leu Leu Met Asp Lys Glu Met Tyr
    565                 570                 575

ACT GGC ATG TCA GAC TTG CAG CCT GCT TCA CCT ACA ATT GAT CGA GGG        1833
Thr Gly Met Ser Asp Leu Gln Pro Ala Ser Pro Thr Ile Asp Arg Gly
580                 585                 590                 595

ATT GCA CTC CAA AAG ATG ATT CAC TTC ATC ACA ATG GCC CTT GGA GGT        1881
Ile Ala Leu Gln Lys Met Ile His Phe Ile Thr Met Ala Leu Gly Gly
                600                 605                 610

GAT GGC TAC TTG AAT TTT ATG GGA AAT GAG TTT GGT CAC CCA GAA TGG        1929
Asp Gly Tyr Leu Asn Phe Met Gly Asn Glu Phe Gly His Pro Glu Trp
            615                 620                 625

ATT GAC TTT CCA AGA GAA GGG AAC AAC TGG AGC TAT GAT AAA TGC AGA        1977
Ile Asp Phe Pro Arg Glu Gly Asn Asn Trp Ser Tyr Asp Lys Cys Arg
        630                 635                 640
```

```
CGA CAG TGG AGC CTT GTG GAC ACT GAT CAC TTG CGG TAC AAG TAC ATG     2025
Arg Gln Trp Ser Leu Val Asp Thr Asp His Leu Arg Tyr Lys Tyr Met
        645                 650                 655

AAT GCG TTT GAC CAA GCG ATG AAT GCG CTC GAT GAG AGA TTT TCC TTC     2073
Asn Ala Phe Asp Gln Ala Met Asn Ala Leu Asp Glu Arg Phe Ser Phe
660                 665                 670                 675

CTT TCG TCG TCA AAG CAG ATC GTC AGC GAC ATG AAC GAT GAG GAA AAG     2121
Leu Ser Ser Ser Lys Gln Ile Val Ser Asp Met Asn Asp Glu Glu Lys
                680                 685                 690

GTT ATT GTC TTT GAA CGT GGA GAT TTA GTT TTT GTT TTC AAT TTC CAT     2169
Val Ile Val Phe Glu Arg Gly Asp Leu Val Phe Val Phe Asn Phe His
            695                 700                 705

CCC AAG AAA ACT TAC GAG GGC TAC AAA GTG GGA TGC GAT TTG CCT GGG     2217
Pro Lys Lys Thr Tyr Glu Gly Tyr Lys Val Gly Cys Asp Leu Pro Gly
        710                 715                 720

AAA TAC AGA GTA GCC CTG GAC TCT GAT GCT CTG GTC TTC GGT GGA CAT     2265
Lys Tyr Arg Val Ala Leu Asp Ser Asp Ala Leu Val Phe Gly Gly His
725                 730                 735

GGA AGA GTT GGC CAC GAC GTG GAT CAC TTC ACG TCG CCT GAA GGG GTG     2313
Gly Arg Val Gly His Asp Val Asp His Phe Thr Ser Pro Glu Gly Val
740                 745                 750                 755

CCA GGG GTG CCC GAA ACG AAC TTC AAC AAC CGG CCG AAC TCG TTC AAA     2361
Pro Gly Val Pro Glu Thr Asn Phe Asn Asn Arg Pro Asn Ser Phe Lys
                760                 765                 770

GTC CTT TCT CCG CCC CGC ACC TGT GTG GCT TAT TAC CGT GTA GAC GAA     2409
Val Leu Ser Pro Pro Arg Thr Cys Val Ala Tyr Tyr Arg Val Asp Glu
            775                 780                 785

GCA GGG GCT GGA CGA CGT CTT CAC GCG AAA CGA GAG ACA GGA AAG ACG     2457
Ala Gly Ala Gly Arg Arg Leu His Ala Lys Arg Glu Thr Gly Lys Thr
        790                 795                 800

TCT CCA GCA GAG AGC ATC GAC GTC AAA GCT TCC AGA GCT AGT AGC AAA     2505
Ser Pro Ala Glu Ser Ile Asp Val Lys Ala Ser Arg Ala Ser Ser Lys
805                 810                 815

GAA GAC AAG GAG GCA ACG GCT GGT GGC AAG AAG GGA TGG AAG TTT GCG     2553
Glu Asp Lys Glu Ala Thr Ala Gly Gly Lys Lys Gly Trp Lys Phe Ala
820                 825                 830                 835

CGG CAG CCA TCC GAT CAA GAT ACC AAA TGAAGCCAGG AGTCCTTGGT           2600
Arg Gln Pro Ser Asp Gln Asp Thr Lys
                840

GAGGACTGGA CTGGCTGCCG GCGCCCTGTT AGTAGTCCTG CTCTACTGGA CTAGCCGCCG   2660

CTGGCGCCCT TGGAACGGTC CTTTCCTGTA GCTTGCAGGC GACTGGTGTC TCATCACCGA   2720

GCAGGCAGGC ACTGCTTGTA TAGCTTTTCT AGAATAATAA TCAGGGATGG AT           2772

(2) INFORMATION FOR SEQ ID NO:13:

(i) SEQUENCE CHARACTERISTICS:
        (A) LENGTH:  373 base pairs
        (B) TYPE:  nucleic acid
        (C) STRANDEDNESS:  single
        (D) TOPOLOGY:  linear (ii) MOLECULE TYPE:  DNA (genomic)

(iv) ANTI-SENSE:  YES (xi) SEQUENCE DESCRIPTION:  SEQ ID NO:13:

CGGTGATGAG ACACCAGTCG CCTGCAAGCT ACAGGAAAGG ACCGTTCCAA GGGCGCCAGC    60

GGCGGCTAGT CCAGTAGAGC AGGACTACTA ACAGGGCGCC GGCAGCCAGT CCAGTCCTCA   120

CCAAGGACTC CTGGCTTCAT TTGGTATCTT GATCGGATGG CTGCCGCGCA AACTTCCATC   180
```

```
CCTTCTTGCC ACCAGCCGTT GCCTCCTTGT CTTCTTTGCT ACTAGCTCTG GAAGCTTTGA      240

CGTCGATGCT CTCTGCTGGA GACGTCTTTC CTGTCTCTCG TTTCGCGTGA AGACGTCGTC      300

CAGCCCCTGC TTCGTCTACA CGGTAATAAG CCACACAGGT GCGGGCGGA GAAAGGACTT       360

TGAACGAGTT CGG                                                        373

(2) INFORMATION FOR SEQ ID NO:14:

(i) SEQUENCE CHARACTERISTICS:
        (A) LENGTH:  27 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:14:

GAATTCCCGG GCCGAACTCG TTCAAAG                                          27

(2) INFORMATION FOR SEQ ID NO:15:

(i) SEQUENCE CHARACTERISTICS:
        (A) LENGTH: 30 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:15:

GAATTCCATG GCGGTGATGA GACACCAGTC                                       30

(2) INFORMATION FOR SEQ ID NO:16:

(i) SEQUENCE CHARACTERISTICS:
        (A) LENGTH:  571 base pairs
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:16:

CCATCTTATG GTTTGCACCA TTCCAGTCAT TGAAGTCACC AATAAGCTCT GCCTCCTGCG       60

CAGCAGGTGC CCATTCACGA TATACAGTTC CATCCTCATT TGTATTAATC CCAAATTTCA      120

AATAGCCTTT AGAAAAAGAT TCAAGACCTT CCCTCATTTT CTTCAATTGA TCCTTTCTGC      180

TCTAGGAATC TTTTCATCCG GTACCTGAAA TGGTCCTTGA ATATCTCCAG CTTGGGGTCC      240

AGGTCGTATA TGGGGAGATG GTCGACATCG CCTTTGGCAG TTGCCATAGT TTTATCTTCT      300

TGCACAGTAG CTGCAGTGGC GAATTTGCTC TTGACCTTCC GCACCCCTGA CCGGCGAGCC      360

TTGCACTGGA CAGACAACAC ACTCAGGCGC ACATTGCCGC CACCCGCGAT CCCCGGCGGT      420

GCCGCCCGAT CAGCATGCGA GCAAGAGCGA CGATGGCCTT GGAGTCGTCG TCGGCCGGCT      480

TGGCGGGCGA CGGTGGCAAC GGCACGACGG CCTTCTCCTC GGCGATGTCC TTGGCGGCCT      540

CCACCTCCGC CGCCGTCATA TCTATGCTAT G                                    571

(2) INFORMATION FOR SEQ ID NO:17:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear
```

(ii) MOLECULE TYPE: other nucleic acid
            (A) DESCRIPTION: /desc = "PCR primer"

(xi) SEQUENCE DESCRIPTION: SEQ ID NO:17:

GAATTCCATG GCCATCTTAT GGTTTGCACC                                    30

(2) INFORMATION FOR SEQ ID NO:18:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(xi) SEQUENCE DESCRIPTION: SEQ ID NO:18:

GAATTCCCGG GCATAGCATA GATATGACGG C                                  31

(2) INFORMATION FOR SEQ ID NO:19:

(i) SEQUENCE CHARACTERISTICS:
            (A) LENGTH: 2487 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:19:

AGCTTTGACG TCGATGCTCT CTGCTGGAGA CGTCTTTCCT GTCTCTCGTT TCGCGTGAAG    60

ACGTCGTCCA GCCCCTGCTT CGTCTACACG GTAATAAGCC ACACAGGTGC GGGGCGGAGA   120

AAGGACTTTG AACGAGTTCG GCCGGTTGTT GAAGTTCGTT TCGGGCACCC CTGGCACCCC   180

TTCAGGCGAC GTGAAGTGAT CCACGTCGTG GCCAACTCTT CCATGTCCAC CGAAGACCAG   240

AGCATCGAGA TCCAGGGCTA CTCTGTATTT CCCAGGCAAA TCGCATCCCA CTTTGTAGCC   300

CTCGTAAGTT TTCTTGGGAT GGAAATTGAA ACAAAAACT AAATCTCCAC GTTCAAAGAC    360

AATAACCTTT TCCTCATCGT TCATGTCGCT GACGATCTGC TTTGACGACG AAAGGAAGGA   420

AAATCTCTCA TCGAGCGCAT TCATCGCTTG GTCAAACGCA TTCATGTACT TGTACCGCAA   480

GTGATCAGTG TCCACAAGGC TCCACTGTCG TCTGCATTTA TCATAGCTCC AGTTGTTCCC   540

TTCTCTTGGA AAGTCAATCC ATTCTGGGTG ACCAAACTCA TTTCCCATAA AATTCAAGTA   600

GCCATCACCT CCAAGGGCCA TTGTGATGAA GTGAATCATC TTTTGGAGTG CAATCCCTCG   660

ATCAATTGTA GGTGAAGCAG GCTGCAAGTC TGACATGCCA GTGTACATTT CCTTGTCCAT   720

CAGGAGAAAT GCAATAGTTT TGTCGCCAAC AATAGACTGA TCATGGCTCT CAGCATATGC   780

GATGCATTTT TCAGTATATC TCCTGTTAGT CAAAGTATGC GCTATTTCAC CCATCGACCA   840

CTCAGAGTCA TCTTTATTCT TCAGGTAGTC AATCCATCTA TCAGGGATAG CCATTGCCAG   900

GCGATAGTCA AACCCAACCC CACCTTCATC AACTGGCCGG CAAAGGACCG GCATGCCTGA   960

AACATCTTCA GCAACAACAG TTGCTTCTGG CAAGAGTTTG TGCATTAAAT GGTTTGCAAG  1020

CATCATGTAA ACAACTGCAT CCACAGCTGT GTCCAAACTG AAATATTCCT GGTAGTTTCC  1080

AGTAAACCCC ACATTGATAC CATGGTGATG ATACAGCATT GATGTAACTC CATCAAATCG  1140

GAAGCCATCA AACATGAATT CATCCAACCA ATATCTCAGG TTAGAAAGAA GAAACCTTAA  1200

TACCTCCCAG TTAGCATAGT TGAACAGCCG ACTATCCCAA AGTTTATGAT AACCTCTATC  1260

```
TCCCGCATGA AAATAGGACT CTTGGGTGCT TTGTCCAACA TCATAGCCAT TTAAACCATC    1320

TGTGACATTA TTACTTGCAT GGCTATGGAC AACATCCATC AGAACTCGCA AACCCAAACT    1380

GTGTGCCTTA TCAACAAGAT ATTTGAGGTC CTCTGGTGTG CCTGATCTGC TGCTAACCGC    1440

AAAGAAATTT GTCACATGGT ACCCGAAAGA AGCATAGTAC GAATGCTCCA TAACTGCCAT    1500

CAACTGAACT GTGTTGTAGT TATTTGCTCG TATGCGTGGC AACACATTGT CTGCAAATTC    1560

CCTATATGTG CTTACTGCTG GCTTTTCACC ACTCATACCT ACATGGGCTT CATAGATACG    1620

TGGAGCAGCA GGCTTTGAAG GCCGAGGATG CTTAAATGTG TACCTTTCAG AAGCAGGAGG    1680

ATCCCAATGA ACACCATCAT AGGGAGCTCC AAATTTAGAG GCATCAACAG TCGCATAACG    1740

AATCAATGCT GGAATACGAT CAACCCATAC TCCACCATGT AGAAAGCGAA ATTTAACCTT    1800

GGAATTGTGA GGGATGGCAG GTTTCCCTTT GACATGGTCA ATTTTGATCG ACCAAACACC    1860

AAATTTATCC TTCTCCATCT TATGGTTTGC ACCATTCCAG TCATTGAAGT CACCAATAAG    1920

CTCTGCCTCC TGCGCAGCAG GTGCCCATTC ACGATATACA GTTCCATCCT CATTTGTATT    1980

AATCCCAAAT TTCAAATAGC CTTTAGAAAA AGATTCAAGA CTTCCCTCAT TTTCTTCAAT    2040

TGATCCTTTC TGCTCTAGGA ATCTTTTCAT CCGGTACCTG AAATGGTCCT TGAATATCTC    2100

CAGCTTGGGG TCCAGGTCGT ATATGGGGAG ATGGTCGACA TCGCCTTTGG CAGTTGCCAT    2160

AGTTTTATCT TCTTGCACAG TAGCTGCAGT GGCGAATTTG CTCTTGACCT TCCGCACCCC    2220

TGACCGGCGA GCCTTGCACT GGACAGACAA CACACTCAGG CGCACATTGC CGCCACCCGC    2280

GATCCCCGGC GGTGCCGCCC GATCAGCATG CGAGCAAGAG CGACGATGGC CTTGGAGTCG    2340

TCGTCGGCCG GCTTGGCGGG CGACGGTGGC AACGGCACGA CGGCCTTCTC CTCGGCGATG    2400

TCCTTGGCGG CCTCCACCTC CGCCGCCGTC ATATCTATGC TATGCTACCT GCTGCTGCTG    2460

CTGCTGAATT CCCTCACTCG ATCAGCA                                      2487

(2) INFORMATION FOR SEQ ID NO:20:

(i) SEQUENCE CHARACTERISTICS:
        (A) LENGTH: 1865 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

ATGGCGGCGG CGGAGGTGGA GGCCGCCAAG GACATCGCCG AGGAGAAGGC CGTCGTGCCG      60

TTGCCACCGT CGCCCGCCAA GCCGGCCGAC GACGACTCCA AGGCCATCGT CGCTCTTGCT     120

CGCATGCTGA TCGGGCGGCA CCGCCGGGGA TCGCGGGTGG CGGCAATGTG CGCCTGAGTG     180

TGTTGTCTGT CCAGTGCAAG GCTCGCCGGT CAGGGGTGCG GAAGGTCAAG AGCAAATTCG     240

CCACTGCAGC TACTGTGCAA GAAGATAAAA CTATGGCAAC TGCCAAAGGC GATGTCGACC     300

ATCTCCCCAT ATACGACCTG GACCCCAAGC TGGAGATATT CAAGGACCAT TTCAGGTACC     360

GGATGAAAAG ATTCCTAGAG CAGAAAGGAT CAATTGAAGA AAATGAGGGA AGTCTTGAAT     420

CTTTTTCTAA AGGCTATTTG AAATTTGGGA TTAATACAAA TGAGGATGGA ACTGTATATC     480

GTGAATGGGC ACCTGCTGCG CAGGAGGCAG AGCTTATTGG TGACTTCAAT GACTGGAATG     540

GTGCAAACCA TAAGATGGAG AAGGATAAAT TTGGTGTTTG GTCGATCAAA ATTGACCATG     600

TCAAAGGGAA ACCTGCCATC CCTCACAATT CCAAGGTTAA ATTTCGCTTT CTACATGGTG     660

GAGTATGGGT TGATCGTATT CCAGCATTGA TTCGTTATGC GACTGTTGAT GCCTCTAAAT     720
```

```
TTGGAGCTCC CTATGATGGT GTTCATTGGG ATCCTCCTGC TTCTGAAAGG TACACATTTA      780

AGCATCCTCG GCCTTCAAAG CCTGCTGCTC CACGTATCTA TGAAGCCCAT GTAGGTATGA      840

GTGGTGAAAA GCCAGCAGTA AGCACATATA GGGAATTTGC AGACAATGTG TTGCCACGCA      900

TACGAGCAAA TAACTACAAC ACAGTTCAGT TGATGGCAGT TATGGAGCAT TCGTACTATG      960

CTTCTTTCGG GTACCATGTG ACAAATTTCT TTGCGGTTAG CAGCAGATCA GGCACACCAG     1020

AGGACCTCAA ATATCTTGTT GATAAGGCAC ACAGTTTGGG TTTGCGAGTT CTGATGGATG     1080

TTGTCCATAG CCATGCAAGT AATAATGTCA CAGATGGTTT AAATGGCTAT GATGTTGGAC     1140

AAAGCACCCA AGAGTCCTAT TTTCATGCGG GAGATAGAGG TTATCATAAA CTTTGGGATA     1200

GTCGGCTGTT CAACTATGCT AACTGGGAGG TATTAAGGTT TCTTCTTTCT AACCTGAGAT     1260

ATTGGTTGGA TGAATTCATG TTTGATGGCT TCCGATTTGA TGGAGTTACA TCAATGCTGT     1320

ATCATCACCA TGGTATCAAT GTGGGGTTTA CTGGAAACTA CCAGGAATAT TTCAGTTTGG     1380

ACACAGCTGT GGATGCAGTT GTTTACATGA TGCTTGCAAA CCATTTAATG CACAAACTCT     1440

TGCCAGAAGC AACTGTTGTT GCTGAAGATG TTTCAGGCAT GCCGGTCCTT TGCCGGCCAG     1500

TTGATGAAGG TGGGGTTGGG TTTGACTATC GCCTGGCAAT GGCTATCCCT GATAGATGGA     1560

TTGACTACCT GAAGAATAAA GATGACTCTG AGTGGTCGAT GGGTGAAATA GCGCATACTT     1620

TGACTAACAG GAGATATACT GAAAAATGCA TCGCATATGC TGAGAGCCAT GATCAGTCTA     1680

TTGTTGGCGA CAAAACTATT GCATTTCTCC TGATGGACAA GGAAATGTAC ACTGGCATGT     1740

CAGACTTGCA GCCTGCTTCA CCTACAATTG ATCGAGGGAT TGCACTCCAA AAGATGATTC     1800

ACTTCATCAC AATGGCCCTT GGAGGTGATG GCTACTTGAA TTTTATGGGA AATGAGTTTG     1860

GTCAC                                                                 1865

(2) INFORMATION FOR SEQ ID NO:21:

(i) SEQUENCE CHARACTERISTICS:
        (A) LENGTH:   31 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "PCR primer"

(xi) SEQUENCE DESCRIPTION: SEQ ID NO:21:

CGCGGATCCC GGGTTCCAAG GGCGCCAGCG G                                      31

(2) INFORMATION FOR SEQ ID NO:22:

(i) SEQUENCE CHARACTERISTICS:
        (A) LENGTH:   38 base pairs
        (B) TYPE:  nucleic acid
        (C) STRANDEDNESS:  single
        (D) TOPOLOGY:  linear (ii) MOLECULE TYPE:  other nucleic acid
        (A) DESCRIPTION:  /desc = "PCR primer"

(xi) SEQUENCE DESCRIPTION:  SEQ ID NO:22:

AACTGCAGAA GGATCCCATG GTGTGCCTCG TGTCGCCC                               38

(2) INFORMATION FOR SEQ ID NO:23:

(i) SEQUENCE CHARACTERISTICS:
        (A) LENGTH:   19 base pairs
        (B) TYPE:  nucleic acid
        (C) STRANDEDNESS:  single
        (D) TOPOLOGY:  linear
```

(ii) MOLECULE TYPE: other nucleic acid
            (A) DESCRIPTION: /desc = "PCR primer"

(xi) SEQUENCE DESCRIPTION: SEQ ID NO:23:

GGATGCTTAA ATGTGTACC                                                19

(2) INFORMATION FOR SEQ ID NO:24:

(i) SEQUENCE CHARACTERISTICS:
        (A) LENGTH: 2565 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

ATGGTGTGCC TCGTGTCGCC CTCTTCCTCG CCGACTCCGC TTCCGCCGCC GCGGCGCTCT      60

CGCTCGCATG CTGATCGGGC GGCACCGCCG GGGATCGCGG GTGGCGGCAA TGTGCGCCTG     120

AGTGTGTTGT CTGTCCAGTG CAAGGCTCGC CGGTCAGGGG TGCGGAAGGT CAAGAGCAAA     180

TTCGCCACTG CAGCTACTGT GCAAGAAGAT AAAACTATGG CAACTGCCAA AGGCGATGTC     240

GACCATCTCC CCATATACGA CCTGGACCCC AAGCTGGAGA TATTCAAGGA CCATTTCAGG     300

TACCGGATGA AAAGATTCCT AGAGCAGAAA GGATCAATTG AAGAAAATGA GGGAAGTCTT     360

GAATCTTTTT CTAAAGGCTA TTTGAAATTT GGGATTAATA CAAATGAGGA TGGAACTGTA     420

TATCGTGAAT GGGCACCTGC TGCGCAGGAG GCAGAGCTTA TTGGTGACTT CAATGACTGG     480

AATGGTGCAA ACCATAAGAT GGAGAAGGAT AAATTTGGTG TTTGGTCGAT CAAAATTGAC     540

CATGTCAAAG GGAAACCTGC CATCCCTCAC AATTCCAAGG TTAAATTTCG CTTTCTACAT     600

GGTGGAGTAT GGGTTGATCG TATTCCAGCA TTGATTCGTT ATGCGACTGT TGATGCCTCT     660

AAATTTGGAG CTCCCTATGA TGGTGTTCAT TGGGATCCTC CTGCTTCTGA AAGGTACACA     720

TTTAAGCATC CTCGGCCTTC AAAGCCTGCT GCTCCACGTA TCTATGAAGC CCATGTAGGT     780

ATGAGTGGTG AAAAGCCAGC AGTAAGCACA TATAGGGAAT TTGCAGACAA TGTGTTGCCA     840

CGCATACGAG CAAATAACTA CAACACAGTT CAGTTGATGG CAGTTATGGA GCATTCGTAC     900

TATGCTTCTT TCGGGTACCA TGTGACAAAT TTCTTTGCGG TTAGCAGCAG ATCAGGCACA     960

CCAGAGGACC TCAAATATCT TGTTGATAAG GCACACAGTT TGGGTTTGCG AGTTCTGATG    1020

GATGTTGTCC ATAGCCATGC AAGTAATAAT GTCACAGATG GTTTAAATGG CTATGATGTT    1080

GGACAAAGCA CCCAAGAGTC CTATTTTCAT GCGGGAGATA GAGGTTATCA TAAACTTTGG    1140

GATAGTCGGC TGTTCAACTA TGCTAACTGG GAGGTATTAA GGTTTCTTCT TTCTAACCTG    1200

AGATATTGGT TGGATGAATT CATGTTTGAT GGCTTCCGAT TTGATGGAGT TACATCAATG    1260

CTGTATCATC ACCATGGTAT CAATGTGGGG TTTACTGGAA ACTACCAGGA ATATTTCAGT    1320

TTGGACACAG CTGTGGATGC AGTTGTTTAC ATGATGCTTG CAAACCATTT AATGCACAAA    1380

CTCTTGCCAG AAGCAACTGT TGTTGCTGAA GATGTTTCAG GCATGCCGGT CCTTTGCCGG    1440

CCAGTTGATG AAGGTGGGGT TGGGTTTGAC TATCGCCTGG CAATGGCTAT CCCTGATAGA    1500

TGGATTGACT ACCTGAAGAA TAAAGATGAC TCTGAGTGGT CGATGGGTGA AATAGCGCAT    1560

ACTTTGACTA ACAGGAGATA TACTGAAAAA TGCATCGCAT ATGCTGAGAG CCATGATCAG    1620

TCTATTGTTG GCGACAAAAC TATTGCATTT CTCCTGATGG ACAAGGAAAT GTACACTGGC    1680

ATGTCAGACT TGCAGCCTGC TTCACCTACA ATTGATCGAG GGATTGCACT CCAAAAGATG    1740

-continued

```
ATTCACTTCA TCACAATGGC CCTTGGAGGT GATGGCTACT TGAATTTTAT GGGAAATGAG    1800

TTTGGTCACC CAGAATGGAT TGACTTTCCA AGAGAAGGGA ACAACTGGAG CTATGATAAA    1860

TGCAGACGAC AGTGGAGCCT TGTGGACACT GATCACTTGC GGTACAAGTA CATGAATGCG    1920

TTTGACCAAG CGATGAATGC GCTCGATGAG AGATTTTCCT TCCTTTCGTC GTCAAAGCAG    1980

ATCGTCAGCG ACATGAACGA TGAGGAAAAG GTTATTGTCT TTGAACGTGG AGATTTAGTT    2040

TTTGTTTTCA ATTTCCATCC CAAGAAAACT TACGAGGGCT ACAAAGTGGG ATGCGATTTG    2100

CCTGGGAAAT ACAGAGTAGC CCTGGACTCT GATGCTCTGG TCTTCGGTGG ACATGGAAGA    2160

GTTGGCCACG ACGTGGATCA CTTCACGTCG CCTGAAGGGG TGCCAGGGGT GCCCGAAACG    2220

AACTTCAACA ACCGGCCGAA CTCGTTCAAA GTCCTTTCTC CGCCCCGCAC CTGTGTGGCT    2280

TATTACCGTG TAGACGAAGC AGGGGCTGGA CGACGTCTTC ACGCGAAACG AGAGACAGGA    2340

AAGACGTCTC CAGCAGAGAG CATCGACGTC AAAGCTTCCA GAGCTAGTAG CAAAGAAGAC    2400

AAGGAGGCAA CGGCTGGTGG CAAGAAGGGA TGGAAGTTTG CGCGGCAGCC ATCCGATCAA    2460

GATACCAAAT GAAGCCAGGA GTCCTTGGTG AGGACTGGAC TGGCTGCCGG CGCCCTGTTA    2520

GTAGTCCTGC TCTACTGGAC TAGCCGCCGC TGGCGCCCTT GGAAC                    2565
```

(2) INFORMATION FOR SEQ ID NO:25:

(i) SEQUENCE CHARACTERISTICS:
        (A) LENGTH: 1809 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
ATGGTGTGCC TCGTGTCGCC CTCTTCCTCG CCGACTCCGC TTCCGCCGCC GCGGCGCTCT      60

CGCTCGCATG CTGATCGGGC GGCACCGCCG GGGATCGCGG GTGGCGGCAA TGTGCGCCTG     120

AGTGTGTTGT CTGTCCAGTG CAAGGCTCGC CGGTCAGGGG TGCGGAAGGT CAAGAGCAAA     180

TTCGCCACTG CAGCTACTGT GCAAGAAGAT AAAACTATGG CAACTGCCAA AGGCGATGTC     240

GACCATCTCC CCATATACGA CCTGGACCCC AAGCTGGAGA TATTCAAGGA CCATTTCAGG     300

TACCGGATGA AAAGATTCCT AGAGCAGAAA GGATCAATTG AAGAAAATGA GGGAAGTCTT     360

GAATCTTTTT CTAAAGGCTA TTTGAAATTT GGGATTAATA CAAATGAGGA TGGAACTGTA     420

TATCGTGAAT GGGCACCTGC TGCGCAGGAG GCAGAGCTTA TTGGTGACTT CAATGACTGG     480

AATGGTGCAA ACCATAAGAT GGAGAAGGAT AAATTTGGTG TTTGGTCGAT CAAAATTGAC     540

CATGTCAAAG GGAAACCTGC CATCCCTCAC AATTCCAAGG TTAAATTTCG CTTTCTACAT     600

GGTGGAGTAT GGGTTGATCG TATTCCAGCA TTGATTCGTT ATGCGACTGT TGATGCCTCT     660

AAATTTGGAG CTCCCTATGA TGGTGTTCAT TGGGATCCTC CTGCTTCTGA AAGGTACACA     720

TTTAAGCATC CTCGGCCTTC AAAGCCTGCT GCTCCACGTA TCTATGAAGC CCATGTAGGT     780

ATGAGTGGTG AAAAGCCAGC AGTAAGCACA TATAGGGAAT TTGCAGACAA TGTGTTGCCA     840

CGCATACGAG CAAATAACTA CAACACAGTT CAGTTGATGG CAGTTATGGA GCATTCGTAC     900

TATGCTTCTT TCGGGTACCA TGTGACAAAT TTCTTTGCGG TTAGCAGCAG ATCAGGCACA     960

CCAGAGGACC TCAAATATCT TGTTGATAAG GCACACAGTT TGGGTTTGCG AGTTCTGATG    1020

GATGTTGTCC ATAGCCATGC AAGTAATAAT GTCACAGATG GTTTAAATGG CTATGATGTT    1080

GGACAAAGCA CCCAAGAGTC CTATTTTCAT GCGGGAGATA GAGGTTATCA TAAACTTTGG    1140
```

-continued

| | | | | | |
|---|---|---|---|---|---|
| GATAGTCGGC | TGTTCAACTA | TGCTAACTGG | GAGGTATTAA | GGTTTCTTCT | TTCTAACCTG | 1200 |
| AGATATTGGT | TGGATGAATT | CATGTTTGAT | GGCTTCCGAT | TTGATGGAGT | TACATCAATG | 1260 |
| CTGTATCATC | ACCATGGTAT | CAATGTGGGG | TTTACTGGAA | ACTACCAGGA | ATATTTCAGT | 1320 |
| TTGGACACAG | CTGTGGATGC | AGTTGTTTAC | ATGATGCTTG | CAAACCATTT | AATGCACAAA | 1380 |
| CTCTTGCCAG | AAGCAACTGT | TGTTGCTGAA | GATGTTTCAG | GCATGCCGGT | CCTTTGCCGG | 1440 |
| CCAGTTGATG | AAGGTGGGGT | TGGGTTTGAC | TATCGCCTGG | CAATGGCTAT | CCCTGATAGA | 1500 |
| TGGATTGACT | ACCTGAAGAA | TAAAGATGAC | TCTGAGTGGT | CGATGGGTGA | AATAGCGCAT | 1560 |
| ACTTTGACTA | ACAGGAGATA | TACTGAAAAA | TGCATCGCAT | ATGCTGAGAG | CCATGATCAG | 1620 |
| TCTATTGTTG | GCGACAAAAC | TATTGCATTT | CTCCTGATGG | ACAAGGAAAT | GTACACTGGC | 1680 |
| ATGTCAGACT | TGCAGCCTGC | TTCACCTACA | ATTGATCGAG | GGATTGCACT | CCAAAAGATG | 1740 |
| ATTCACTTCA | TCACAATGGC | CCTTGGAGGT | GATGGCTACT | TGAATTTTAT | GGGAAATGAG | 1800 |
| TTTGGTCAC | | | | | | 1809 |

What is claimed is:

1. A method of controlling the starch fine structure of starch derived from a grain of corn comprising:
   (a) preparing a chimeric gene comprising a nucleic acid fragment sufficient to suppress the endogenous expression of a corn starch branching enzyme I or II, wherein said nucleic acid fragment comprises at least a portion of corn starch branching enzyme I or II, operably linked in sense or antisense orientation on the upstream side to a promoter that directs gene expression in corn endosperm tissue, and operably linked on the downstream side to a regulatory sequence for transcriptional termination, and
   (b) transforming corn with the chimeric gene of step (a), wherein expression of said chimeric gene results in alteration of the fine structure of starch derived from the grain of said transformed corn compared to the fine structure of starch derived from corn not possessing said chimeric gene.

2. The method of claim 1 wherein said alteration of starch fine structure comprises increase in the average size of the branch chains of the amylopectin molecular component of said starch.

3. The method of claim 1 wherein said alteration of starch fine structure comprises increase in the ratio of the amylose molecular component to the amylopectin molecular component of said starch.

4. The method of claim 1 wherein said alteration of starch fine structure comprises increase in the average size of the branch chains of the amylopectin molecular component and increase in the ratio of the amylose molecular component to the amylopectin molecular component of said starch.

5. The method of claim 1 wherein the nucleic acid fragment encodes at least a portion of the corn SBEIIb enzyme.

6. The method of claim 1 wherein the nucleic acid fragment encodes at least a portion of the corn SBEI enzyme.

7. A corn variety prepared by the method of claim 1, said corn variety having a chimeric gene comprising a nucleic acid fragment sufficient to suppress the endogenous expression of a corn starch branching enzyme I or II, wherein said nucleic acid fragment comprises at least a portion of corn starch branching enzyme I or II, or any progeny thereof; wherein said progeny comprise said chimeric gene.

8. The corn variety of claim 7 wherein the ratio of the amylose molecular component to the amylopectin molecular component of the starch isolated from the grain of said corn variety is increased compared to the ratio of the amylose molecular component to the amylopectin molecular component of starch isolated from the grain of untransformed corn.

9. The corn variety of claim 7 wherein the amylopectin molecular component of the starch isolated from the grain of said corn variety comprises a greater proportion of longer $\alpha$-1,4-linked glucan chains and a lesser proportion of shorter $\alpha$-1,4-linked glucan chains compared to the amylopectin molecular component of starch isolated from the grain of untransformed corn.

10. The corn variety of claim 9 wherein the amylopectin component of the starch isolated from the grain of said corn variety has a greater proportion of B3 and B4+ chains compared to the branch chain distribution of the amylopectin molecular component of starch isolated from the grain of untransformed corn.

11. The method of claim 1 wherein the corn is a corn starch mutant selected from the group consisting of waxy and amylose extender.

12. A corn variety containing a transgene sufficient to suppress the endogenous expression of a corn starch branching enzyme I or II and prepared by the method of claim 11 or any progeny thereof, wherein said progeny comprises said transgene.

13. The corn variety of claim 12 that bears the designation XAY00096.

* * * * *